(12) United States Patent
Ren et al.

(10) Patent No.: US 9,393,232 B2
(45) Date of Patent: Jul. 19, 2016

(54) SUBSTITUTED 5-(3,5-DIMETHYLISOXAZOL-4-YL) INDOLINE-2-ONES

(71) Applicant: BeiGene, Ltd., Camana Bay, Grand Cayman, Cayman Islands (KY)

(72) Inventors: Bo Ren, Beijing (CN); Changyou Zhou, Beijing (CN); Hexiang Wang, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 0 days.

(21) Appl. No.: 14/404,798

(22) PCT Filed: Apr. 14, 2014

(86) PCT No.: PCT/CN2014/075257
§ 371 (c)(1),
(2) Date: Dec. 1, 2014

(87) PCT Pub. No.: WO2014/173241
PCT Pub. Date: Oct. 30, 2014

(65) Prior Publication Data
US 2016/0030395 A1    Feb. 4, 2016

(30) Foreign Application Priority Data

Apr. 26, 2013    (WO) ............... PCT/CN2013/074780

(51) Int. Cl.
| | | |
|---|---|---|
| *A61K 31/454* | (2006.01) |
| *A61K 31/496* | (2006.01) |
| *C07D 413/04* | (2006.01) |
| *C07D 413/14* | (2006.01) |
| *A61K 31/422* | (2006.01) |
| *A61K 45/06* | (2006.01) |
| *A61K 31/5377* | (2006.01) |

(52) U.S. Cl.
CPC .............. *A61K 31/422* (2013.01); *A61K 31/454* (2013.01); *A61K 31/496* (2013.01); *A61K 31/5377* (2013.01); *A61K 45/06* (2013.01); *C07D 413/04* (2013.01); *C07D 413/14* (2013.01)

(58) Field of Classification Search
None
See application file for complete search history.

(56) References Cited

U.S. PATENT DOCUMENTS 8,344,018 B2 *    1/2013    Graupe ................ C07D 209/34
514/411

FOREIGN PATENT DOCUMENTS

| CN | 101910182 | 12/2010 |
| CN | 102656147 | 9/2012 |
| WO | WO 2009/084693 A1 | 7/2009 |
| WO | WO 2010/009166 | 1/2010 |
| WO | WO 2011/070039 A1 | 6/2011 |
| WO | WO 2014/154760 A1 | 10/2014 |

OTHER PUBLICATIONS

International Search Report and Written Opinion for International Application No. PCT/CN2014/075257, mailed Jul. 9, 2014, 9 pages.

* cited by examiner

*Primary Examiner* — Kamal Saeed
(74) *Attorney, Agent, or Firm* — Cooley LLP

(57) ABSTRACT

Disclosed are substituted 5-(3,5-dimethylisoxazol-4-yl)indoline-2-one compounds, pharmaceutical compositions comprising at least one such 4 substituted 5-(3,5-dimethylisoxazol-4-yl)indoline-2-one compound processes for the preparation thereof, and the use thereof for inhibiting BET family of bromodomains and for treating disorders mediated thereby, such as certain cancers.

12 Claims, No Drawings

SUBSTITUTED 5-(3,5-DIMETHYLISOXAZOL-4-YL) INDOLINE-2-ONES

CROSS REFERENCE TO RELATED APPLICATIONS

This application is a national phase application based on PCT/CN2014/075257, filed Apr. 14, 2014, which claims the priority of International Patent Application No, PCT/CN2013/074780, filed Apr. 26, 2013; the content of both applications being incorporated herein by reference.

TECHNICAL FIELD

The invention is directed to methods and compounds for inhibiting BRD4 and treating disease associated with undesirable BRD4 activity.

BACKGROUND ART

ε-N-acetylation of lysine residues is one of the most frequently occurring posttranslational modifications in proteins (Choudhary et al., 2009) and has broad relevance to cellular signalling and disease biology. Lysine acetylation in histones is abundant in large macromolecular complexes that are involved in chromatin remodeling, DNA damage repair, and cell-cycle control (Choudhary et al., 2009). Targeting chromatin modifying enzymes that control cellular acetylation levels, the so-called epigenetic 'writers' (histone acetyltransferases, HATs) and 'erasers' (histone deacetylases, HDACs) has been an area of extensive research in drug development, but modulating the 'readers' (bromodomains) that recognize acetylation sites has not been widely reported until recently (Nicodeme et al 2010, Filippakopoulos et al 2010). Bromodomains (BRDs) are a diverse family of evolutionary conserved protein-interaction modules that specifically recognize protein motifs that contain acetyl-lysine modification. The extra-terminal (BET) bromodomain subfamily consists of BRD2, BRD3, BRD4 and BRDT, shares a common domain architecture featuring two amino-terminal bromodomains with high levels of sequence homology, and a carboxy-terminal domain. Recent research has validated targeting BET bromodomains to treat a number of cancers [Filippakopoulos 2010, Delmore 2011, Zuber 2011], atherosclerosis [Chung 2011, Mirguet 2012, inflammation [Nicodeme 2010] and HIV infection [Banerjee 2012].

The MYC transcription factor is a master regulator of diverse cellular functions and has long been validated as a compelling therapeutic target for a range of human cancers, yet strategies to modulate the function of the Myc oncoprotein have not been discovered. Recently, two selective inhibitors of the BET family members (with little activity against bromodomains outside of the BET family), JQ1 and IBET-151, have been shown to potently downregulate MYC protein and MYC target gene transcription. In a MYC-dependent manner, JQ1 and IBET-151 potently inhibit in vitro and in vivo tumor growth of multiple myeloma, a variety of leukemia and lymphoma cell lines as well as primary leukemia patient samples (Delmore 2011, Mertz, 2011, Zuber 2011, Herrmann 2010, Dawson, 2011). BET bromodomain inhibitors could also be useful in treating other cancers that depend on MYC function, such as neuroblastoma with MYCN amplification and other solid tumors with c-MYC overexpression, in addition, JQ1 has also be shown to have antiproliferative effects in an incurable subtype of human squamous carcinoma, known as NUT midline carcinoma (NMC). NMC is a genetically defined cancer with a chromosomal rearrangement involving t(15,19) that leads to expression of the tandem N-terminal bromodomains of BRD4 or BRD3 as an in-frame chimaera with the NUT (nuclear protein in testis) protein. JQ1 treatment leads to terminal differentiation, cell cycle arrest and apoptosis in NMC cell lines, and significant reduction of tumour growth in patient-derived xenograft models [Filippakopoulos 2010]. In summary, BET bromodomain inhibitors can be useful in the treatment of a variety of human cancers.

A BET bromodomain inhibitor, IBET, has been reported to suppress several crucial pro-inflammatory cytokines and chemokines by displacing BET proteins from the promoter of its inflammatory genses. IBET demonstrates anti-inflammatory effect and protects animals from endotoxin-induced death in a mouse sepsis model (Nicodeme 2010). These studies suggest that BET bromodomain inhibitors could be useful as immomodulating drugs.

Apolipoprotein A1 (ApoA1) upregulation is associated with protection from atherosclerosis progression and with anti-inflammatory effects (Nicholls 2012). BET bromodomain inhibitors have been discovered to increase ApoA1 expression. BET inhibitors are promising approaches for the development of new therapies for atherosclerosis.

The persistence of latent HIV-1 is a major challenge in efforts to eradicate infection. JQ1 has been reported to reactivate HIV virus in models of latent T cell infection and latent monocyte infection (Banerjee 2012, Li 2003). Combination therapies using BET bromodomain inhibitors to reactive latent HIV-1 virus can provide an opportunity to cure HIV-1 infection. Other BET bromodomain inhibitors are also known. See, for example, WO2012151512, WO2012143436, WO2012075383, WO2011161031, WO2011143669, WO2011143657, WO2011054848, WO2011054846, WO2011054845, WO2011054844, WO2011054843, WO WO2011054841, WO2011054553, WO2009084693, and WO2006032470. Certain 3,5-dimethylisoxazoles have been identified as BRD4 inhibitors (David S. Hewings 2011).

RELEVENT LITERATURE

Filippakopoulos, Panagis, Jun Qi, Sarah Picaud, Yao Shen, William B. Smith, Oleg Fedorov, Elizabeth M. Morse et al. "Selective inhibition of BET bromodomains." *Nature* 468, no. 7327 (2010): 1067-1073

Delmore, Jake E., Ghayas C. Issa, Madeleine E. Lemieux, Peter B. Rahl, Junwei Shi, Hannah M. Jacobs, Efstathios Kastritis et al. "BET bromodomain inhibition as a therapeutic strategy to target c-Myc." *Cell* 146, no. 6 (2011): 904-917.

Zuber, Johannes, Junwei Shi, Eric Wang, Amy R. Rappaport, Harald Herrmann, Edward A. Sison, Daniel Magoon et al. "RNAi screen identifies Brd4 as a therapeutic target in acute myeloid leukaemia." *Nature* 478, no. 7370 (2011): 524-528.

Chung, Chun-wa, Hervé Coste, Julia H. White, Olivier Mirguet, Jonathan Wilde, Romain L. Gosmini, Chris Delves et al. "Discovery and characterization of small molecule inhibitors of the BET family bromodomains." *Journal of medicinal chemistry* 54, no. 11 (2011): 3827-3838.

Dawson, Mark A., Rab K. Prinjha, Antje Dittmann, George Giotopoulos, Marcus Bantscheff, Wai-In Chan, Samuel C. Robson et al. "Inhibition of BET recruitment to chromatin as an effective treatment for MLL-fusion leukaemia." *Nature* 478, no. 7370 (2011): 529-533. Nicodeme, Edwige, Kate L. Jeffrey, Uwe Schaefer, Soren Beinke, Scott Dewell, Chun-wa Chung, Rohit Chandwani et al. "Suppression of inflammation by a synthetic histone mimic." Nature 468, no. 7327 (2010): 1119-1123.

Hewings, David S., Minghua Wang, Martin Philpott, Oleg Fedorov, Sagar Uttarkar, Panagis Filippakopoulos, Sarah Picaud et al. "3,5-Dimethylisoxazoles act as acetyl-lysine-mimetic bromodomain ligands." Journal of medicinal chemistry 54, no. 19 (2011): 6761-6770.

Choudhary, C., Kumar, C., Gnad, F., Nielsen, M. L., Rehman, M., Walther, T. C., Olsen, J. V., and Mann, M. (2009). Lysine acetylation targets protein complexes and co-regulates major cellular functions. Science 325, 834-840

Herrmann H, Blatt K, Shi J, Gleixner K V, Cerny-Reiterer S, Müllauer L, Vakoc C R, Sperr W R, Horny H P, Bradner J E, Zuber J, Valent P Small-molecule inhibition of BRD4 as a new potent approach to eliminate leukemic stem- and progenitor cells in acute myeloid leukemia AML Oncotarget. 2012 Nov. 27. [Epub ahead of print]

Mertz, Jennifer A., Andrew R. Conery, Barbara M. Bryant, Peter Sandy, Srividya Balasubramanian, Deanna A. Mele, Louise Bergeron, and Robert J. Sims III. "Targeting MYC dependence in cancer by inhibiting BET bromodomains." Proceedings of the National Academy of Sciences 108, no. 40 (2011): 16669-16674.

Banerjee C, Archin N, Michaels D, Belkina A C, Denis G V, Bradner J, Sebastiani P, Margolis D M, Montano M. BET bromodomain inhibition as a novel strategy for reactivation of HIV-1. J Leukoc Biol. 2012 December; 92(6): 1147-54.

Li, Zichong, Jia Guo, Yuntao Wu, and Qiang Zhou. "The BET bromodomain inhibitor JQ1 activates HIV latency through antagonizing Brd4 inhibition of Tat-transactivation." Nucleic Acids Research 41, no. 1 (2013): 277-287.

Chung, Chun-wa, Hervé Coste, Julia H. White, Olivier Mirguet, Jonathan Wilde, Romain L. Gosmini, Chris Delves et al. "Discovery and characterization of small molecule inhibitors of the BET family bromodomains." Journal of medicinal chemistry 54, no. 11 (2011): 3827-3838.

Mirguet, Olivier, Yann Lamotte, Frédéric Donche, Jérôme Toum, Françoise Gellibert, Anne Bouillot, Romain Gosmini et al. "From ApoA1 upregulation to BET family bromodomain inhibition: Discovery of I-BET151." Bioorganic & medicinal chemistry letters (2012).

Nicholls, Stephen J., Allan Gordon, Jan Johannson, Christie M. Ballantyne, Philip J. Barter, H. Bryan Brewer, John J P Kastelein, Norman C. Wong, Marilyn R N Borgman, and Steven E. Nissen. "ApoA-I Induction as a Potential Cardioprotective Strategy: Rationale for the SUSTAIN and ASSURE Studies." Cardiovascular drugs and therapy (2012): 1-7.

David S. Hewings, Minghua Wang, Martin Philpott, Oleg Fedorov, Sagar Uttarkar, Panagis Filippakopoulos, Sarah Picaud, Chaitanya Vuppusetty, Brian Marsden, Stefan Knapp, Stuart J. Conway and Tom D. Heightman. 3,5 Dimethylisoxazoles Act As Acetyl-lysine-mimetic Bromodomain Ligands. J. Med. Chem. 2011, 54, 6761-6770.

SUMMARY OF THE INVENTION

The invention provides methods and compositions for inhibiting $BRD_4$ and treating disease associated with undesirable $BRD_4$ activity.

In one embodiment the invention provides $BRD_4$ inhibitors or compounds of formula:

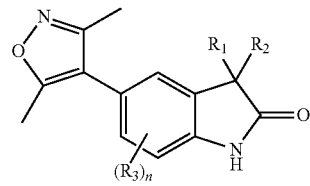

stereoisomers thereof, and pharmaceutically acceptable salts thereof, wherein:

$R^1$ is a hydrogen, halide, heteroatom functional group or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms;

$R^2$ is a heteroatom functional group or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms;

$R^3$ is halogen, lower alkyl, hydroxyl, lower alkyloxy, or lower acyl and n is 0, 1, 2 or 3.

The invention includes all combinations of the recited particular embodiments, as if each combination had been laboriously separately recited.

In exemplary particular embodiments:

$R^1$ is a halide, —$OR^4$ or —$NR^5R^6$, or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring; or $R^1$ is a —$OR^4$ or —$NR^5R^6$, or hydrocarbon selected from C3-C8 cycloalkyl, C5-C8 cycloalkenyl, and C6-C14 aryl, wherein each hydrocarbon is optionally-substituted and optionally comprises 1-3 heteroatoms, wherein $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring; or $R^1$ is —$OR^4$ or —$NR^5R^6$, or C6-C14 aryl, wherein the aryl is optionally-substituted and optionally comprises 1-3 heteroatoms, and $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring.

In exemplary particular embodiments:

$R^2$ is —$OR^4$ or —$NR^5R^6$, or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring; or $R^2$ is —$NR^5R^6$ or hydrocarbon selected from C3-C8 cycloalkyl, C5-C8 cycloalkenyl, and C6-C14 aryl, wherein each hydrocarbon is optionally-substituted and optionally comprises 1-3 heteroatoms, wherein $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring; or $R^2$ is —$NR^5R^6$ or C6-C14 aryl, wherein the aryl is optionally-substituted and optionally comprises 1-3 heteroatoms, and $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring.

In exemplary particular embodiments the invention provides compounds of Table 1, Table 2 or the Examples herein, and pharmaceutically acceptable salts thereof.

In another aspect the invention provides a substituted 5-(3,5-dimethylisoxazol-4-yl)indoline-2-one $BRD_4$-inhibitor, and in exemplary particular embodiments the inhibitor comprises one or two substitutions at C3 of the indoline, wherein the substitutions are independently halide, heteroatom functional group or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms.

The invention also provides subject compounds having a $BRD_4$-inhibiting activity corresponding to an IC50 of 10 μM or less in a $BRD_4$ time-resolved fluorescence resonance energy transfer (TR-FRET) enzyme assay using recombinant human BRD4(1-477) bromodomain expressed and purified from *E. coli* with an N-terminal His tag, in binding mixtures of the bromodomain, the compound and a tetra-acetylated histone peptide.

The invention also provides pharmaceutical compositions comprising a therapeutically effective amount of a subject compound in unit dosage form and one or more pharmaceutically acceptable carriers.

The invention also provides combinations comprising a therapeutically effective amount of a subject compound and a different agent therapeutically active against cancer.

The invention also provides methods of treating a disease associated with undesirable $BRD_4$ activity, which comprises administering to a person in need thereof an effective amount of a subject compound, an N-oxide thereof or a prodrug thereof, particularly wherein the disease is cancer.

The invention also provides pharmaceutical compositions comprising a subject compound in unit dosage, administrable form, and methods of inducing autophagy, comprising administering to a person in need thereof an effective amount of a subject compound or composition.

The invention also provides the subject compounds for use as a medicament, and use of the subject compounds in the manufacture of a medicament for the treatment of a disease associated with undesirable $BRD_4$ activity.

DESCRIPTION OF PARTICULAR EMBODIMENTS OF THE INVENTION

Disclosed herein are novel compounds that inhibit BET domains, such as BRD4.

The following words, phrases and symbols are generally intended to have the meanings as set forth below, except to the extent that the context in which they are used indicates otherwise. The following abbreviations and terms have the indicated meanings throughout.

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C═C double bond and of 2-18, or 2-12, or 2-6 carbon atoms. Examples of the alkenyl group may be selected from ethenyl or vinyl, prop-1-enyl, prop-2-enyl, 2-methyl-prop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

Substituents are selected from: halogen, —R', —OR', =O, =NR', =N—OR', —NR'R", —SR', halogen, —SiR'R"R''', —OC(O)R', —C(O)R', —CO$_2$R', —CONR'R", —OC(O) NR'R", —NR"C(O)R', —NR'—C(O)NR"R''', —NR'— SO$_2$NR''', —NR"CO$_2$R', —NH—C(NH$_2$)=NH, —NR'C (NH$_2$)=NH, —NH—C(NH$_2$)=NR', —S(O)R', —SO$_2$R', —SO$_2$NR'R", —NR"SO$_2$R, —CN and —NO$_2$, —N$_3$, —CH(Ph)$_2$, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4) alkyl groups. When R' and R" are attached to the same nitrogen atom, they can be combined with the nitrogen atom to form a 5-, 6- or 7-membered ring. Hence, —NR'R" includes l-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, perfluoro(C1-C4)alkoxy and perfluoro(C1-C4)alkyl, where R' and R" are as defined above.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof that has, for example, cancer.

An "effective amount" refers to an amount of at least one compound and/or at least one stereoisomer thereof, and/or at least one pharmaceutically acceptable salt thereof effective to "treat" a disease or disorder in a subject, and will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The invention provides methods and compositions for inhibiting $BRD_4$ and treating disease associated with undesirable $BRD_4$ activity ($BRD_4$ related diseases).

The invention provides compounds of formula:

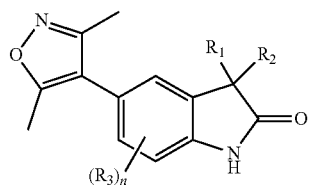

I stereoisomers thereof, and pharmaceutically acceptable salts thereof.

The invention includes all combinations of the recited particular embodiments, as if each combination had been laboriously separately recited.

$R^1$ is a hydrogen, halide, heteroatom functional group or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms.

In particular embodiments $R^1$ is halide, particularly F, Cl, Br or I.

In particular embodiments $R^1$ is a heteroatom functional group, a functional group linked though a heteroatom such as O, N, P, or S, and includes hydroxyl, alkoxy, aryloxy, amine, azo, cyanyl, thiocyanyl, hydroperoxyl, imine, aldimine, isocyanide, iscyante, nitrate, nitrile, nitrite, nitro, nitroso, phosphate, phosphono, sulfide, sulfonyl, sulfo, or sulfhydryl, particularly —$OR^4$ or —$NR^5R_6$, wherein $R^4$, $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms, wherein $R^5$ and $R^6$ together with the atom(s) to which they are attached, each can form an optionally substituted, cyclohydrocarbon ring. Exemplary such rings include optionally substituted 3, 4, 5, 6, 7 and 8-membered rings containing 1, 2, or 3 N heteroatoms and 0, 1, 2 or 3 non-N heteroatoms, and include imidazolidine (imidazole), pyrazolidine (pyrazole), oxazolidine (oxazole), thiazolidine (thiazole), piperidinyl, pyrrolidinyl, piperazine, morpholine, thiomorpholine, triazole, oxadiazole, thiadiazole, dithiazole, etc.

In particular embodiments $R^1$ is C1-C14 hydrocarbon, particularly C1-C8 alkyl, C2-C8 alkenyl, C2-C8 alkynyl, or C6-C14 aryl, wherein each alkyl, alkenyl and alkynyl is optionally cyclized, and each hydrocarbon is optionally-substituted and optionally comprises 1-3 heteroatoms. In particular embodiments $R^1$ is C3-C8 cycloalkyl, C5-C8 cycloalkenyl, or C6-C14 aryl, wherein each hydrocarbon is optionally-substituted and optionally comprises 1-3 heteroatoms.

Exemplary $R^1$ moieties include hydroxyl, amine, phenyl, 3-amine piperidinyl, 3-hydroxypiperidinyl, hydroxylmethyl-, isopropyl-methylamine, etc.

$R^2$ is a heteroatom functional group or hydrocarbon, as described for $R^1$.

Exemplary $R^2$ moieties include cyclohexyl, phenyl, thiophene, phenyl-, hydroxymethyl-methylamine, cyclohexyl-2-one, methyl-, hydroxymethylmethylamine, 2-hydroxymethyl-, 4-hydroxy pyrrolidine, 2-carboxyl, 4-hydroxypyrrolidine, hydroxymethyl-, 5-imidazolmethylmethylamine, 2-hydroxylpropylamine, etc.

$R^3$ is halogen, optionally substituted, particularly halide, particularly F, Cl or Br substituted, lower alkyl, hydroxyl, lower alkyloxy, or lower acyl; examples include F, Cl, Br, $CH_3$, $CF_3$, $OCH_3$ and $OCOCH_3$. In particular embodiments n is 0, 1, 2 or 3.

The invention provides all the compounds of the tables and examples herein, and stereoisomers and pharmaceutically acceptable salts thereof.

In another aspect the invention provides a substituted 5-(3, 5-dimethylisoxazol-4-yl)indoline-2-one $BRD_4$-inhibitor, and in exemplary particular embodiments the inhibitor comprises one or two substitutions at C3 of the indoline, wherein the substitutions are independently heteroatom, heteroatom functional group or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms. In particular embodiments the substitutions are selected from those of $R^1$, $R^2$ and $R^3$ of formula I.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The at least one additional therapeutic agent can be, for example, selected from anti-hyperproliferative, anti-cancer, and chemotherapeutic agents. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CBI-TMI; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gamma1I and calicheamicin omega1I (Angew Chem. Intl. Ed. Engl. (1994) 33:183-186); dynemicin, such as dynemicin A; bis-phosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chlorambucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, such as those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors, (viii) vaccines such as gene therapy vaccines, for example, ALLOVECTIN®, LEUVECTIN®, and VAXID®; PROLEUKIN® rIL-2; a topoisomerase 1 inhibitor such as LURTOTE- CAN®; ABARELIX® rmRH, (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with a subject compound and stereoisomers thereof, and pharmaceutically acceptable salt thereof may, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Also provided is a composition comprising a subject compound, stereoisomer thereof, or pharmaceutically acceptable salt thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

The subject compounds and stereoisomers thereof, and pharmaceutically acceptable salts thereof disclosed herein can further be examined for efficacy in treating $BRD_4$ related diseases by in vivo assays. For example, the compound and/or the at least one pharmaceutically acceptable salts thereof disclosed herein can be administered to an animal (e.g., a mouse model) having BRD4 related diseases and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the subjet compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient, selected, for example, from other active ingredients known to be useful for treating $BRD_4$ related diseases in a patient.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

General Reaction Scheme for Compound Preparation

The subject compounds, stereoisomers and pharmaceutically acceptable salts thereof, can be prepared from (a) commercially available starting materials (b) known starting materials which may be prepared as described in literature procedures (c) new intermediates described in the schemes and experimental procedures herein. In making the compounds of the invention, the order of synthetic steps may be varied to increase the yield of desired product. The compounds and/or the pharmaceutically acceptable salts thereof, can be synthesized from commercially available starting materials taken together with the disclosure herein. The following scheme illustrates methods for preparation of some of the compounds disclosed herein.

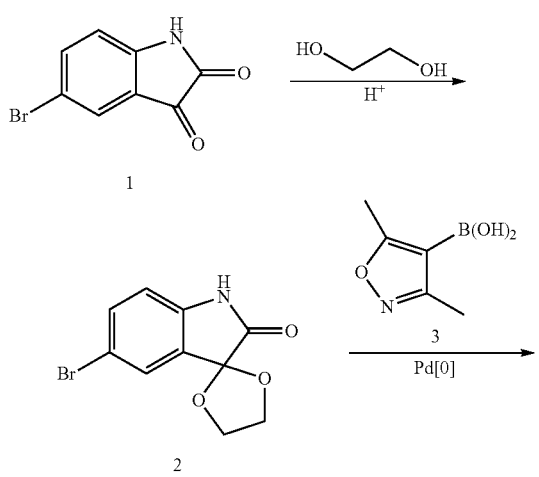

-continued

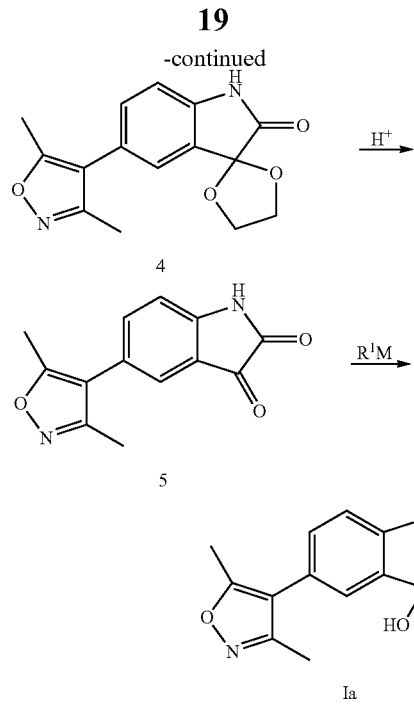

In this scheme, the commercially available 5-bromoindoline-2,3-dione 1 is converted into the ketal 2 which undergoes Suzuki coupling with boronic acid 3. The resulting ketal 4 is de-protected to give 5-(3,5-dimethyl isoxazol-4-yl)indoline-2,3-dione. This key intermediate 5 undergoes addition reactions with organometallic agents such as Grinard reagents to provide compounds of formula Ia under standard conditions known in the art.

The scheme II illustrates methods for preparation of some of the compounds (Ib) and (Ic) disclosed herein.

Scheme II

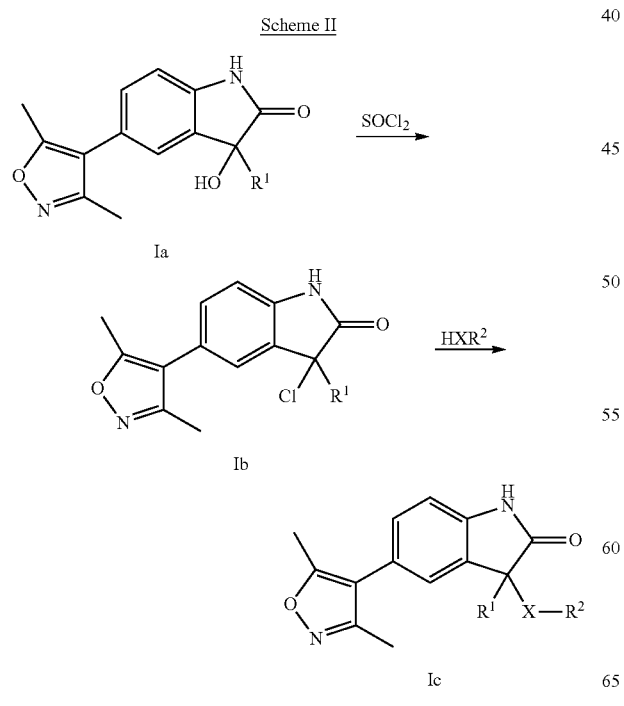

In this scheme, the compound Ia is treated with thionyl chloride to give the compound of formula Ib. The following replacement of chloro group with an amino or hydroxyl group gives a compound of formula Ic under standard conditions known in the art.

The scheme III illustrates methods for preparation of some of the compounds (Id) and (Ie) disclosed herein.

Scheme III

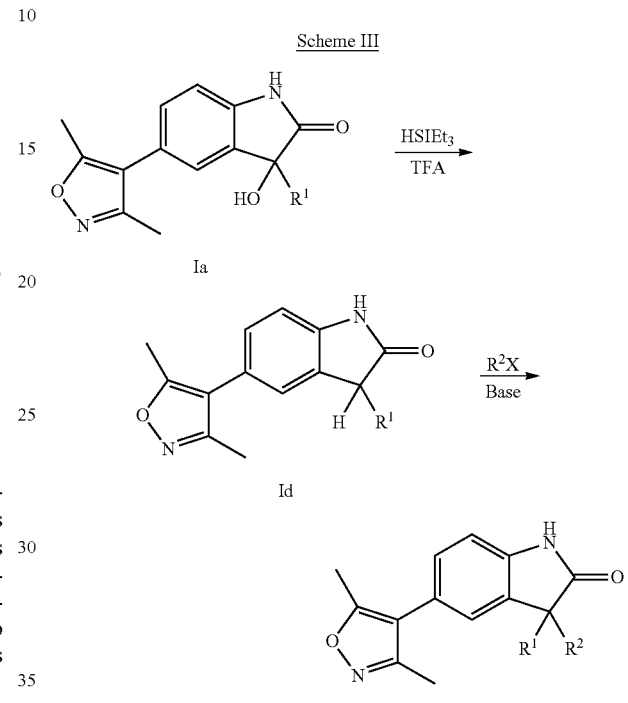

In this scheme, the hydroxyl group of the compound of formula Ia is reduced to the compound of formula Id by triethylsilane under acidic conditions such as trifluoroacetic acid. The compound Id undergoes alkylation reaction to give the compound of formula Ie under standard basic conditions known in the art.

The scheme IV illustrates methods for preparation of some of the compounds (If) disclosed herein.

Scheme IV

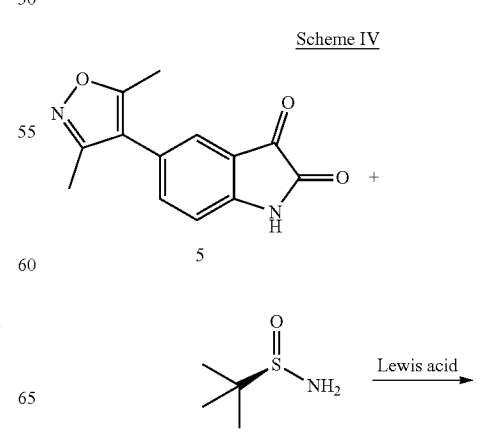

21
-continued

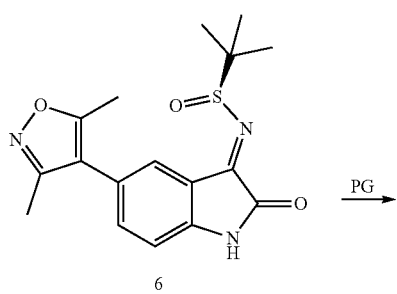

6

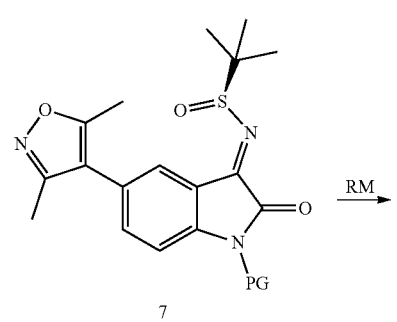

7

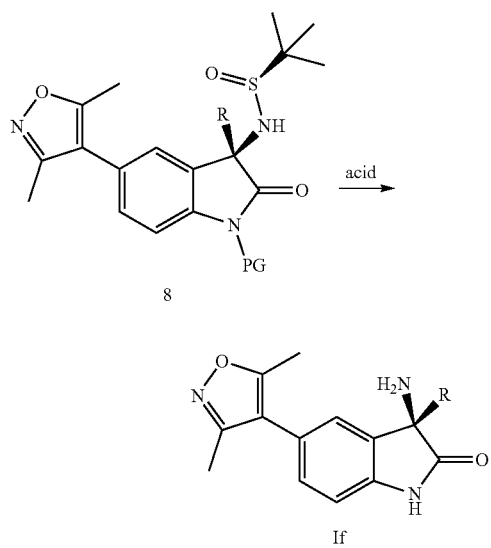

8

If

PG = Protection Group

In this scheme, (R)-2-methylpropane-2-sulfinamide is introduced to 5-(3,5-dimethylisoxazol-4-yl)indoline-2,3-dione under the Lewis acid conditions to give the compound of formula 6, followed by protection to amino group under the condition known in the art. This key intermediate 7 undergoes addition reaction with organometallic agent such as Grignard reagent to provide the compound of formula 8 under standard conditions known in the art, which is de-protected to give the compound of formula If under the acidic conditions known in the art.

The scheme V illustrates methods for preparation of some of the compounds (Ig) disclosed herein.

22

Scheme V

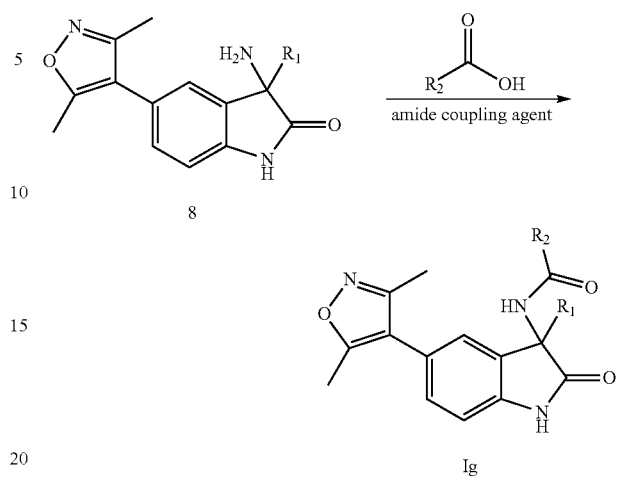

Ig

In this scheme, the resulted amine 8 is coupled with acid to give the compound Ig under the standard amide coupling condition known in the art.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1$H NMR spectra were recorded on a Varian instrument operating at 400 MHz. $^1$H-NMR spectra were obtained using $CDCl_3$, $CD_2Cl_2$, $CD_3OD$, $D_2P$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). Compound names except the reagents were generated by ChemDraw version 12.0.

Abbreviations:
AcOH Acetic acid
Aq Aqueous
Brine Saturated aqueous sodium chloride solution
Bn Benzyl
BnBr Benzyl Bromide
(Boc)$_2$O di-tert-butyl dicarbonate
DMF N,N-Dimethylformamide
Dppf 1,1''-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
Et$_2$O or ether Diethyl ether
Et$_3$N Triethyl amine
HATU O-(7-Azabenzotriazol-1-yl)-N,N,N',N'-tetramethyluronium hexafluorophosphate
HPLC High-performance liquid chromatography
IPA 2-propanol
i-PrOH Isopropyl alcohol
ms or MS Mass spectrum
PE petroleum ether
PPA Polyphosphoric acid
p-TSA p-Tolunesulfonic acid
Rt Retention time
Rt or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography Example 1

Synthesis of Compound 1.1-1.34

Compound 1.1

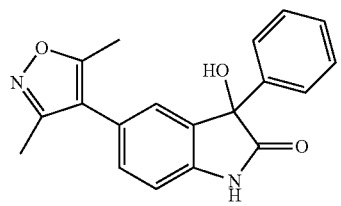 [SMILES: Cc1noc(C)c1-c1ccc2c(c1)C(O)(c1ccccc1)C(=O)N2]

Step 1: 5'-Bromospiro[[1,3]dioxolane-2,3'-indolin]-2'-one

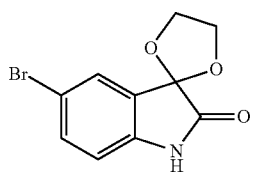 [SMILES: O=C1Nc2ccc(Br)cc2C12OCCO2]

A magnetically stirred solution of 5-bromoindoline-2,3-dione (226 g, 1.0 mol, 1 eq.), ethylene glycol (186 g, 3.0 mol, 3 eq.), p-TSA (30 g, 0.16 mol, 16 mol %) and toluene (1500 mL) was refluxed overnight using a Dean-Stark apparatus. After total consumption of 5-bromoindoline-2,3-dione, EtOAc (1500 mL) and water (1000 mL) were added to remove excess of diol. The aqueous layer was extracted twice with EtOAc (500 mL). The collected organic layers were collected, dried over Na$_2$SO$_4$, filtered and concentrated under reduced pressure. The yellowish solid was washed with diethyl ether to give the desired compound as a pale yellow solid (236 g, 87%). $^1$H NMR (400 MHz, DMSO-d$_6$): $\delta_H$ 10.56 (s, 1H), 7.31-7.33 (m, 2H), 6.93 (d, J=8.0 Hz, 1H), 4.27-4.35 (m, 4H), 2.35 (s, 3H), 2.18 (s, 3H). MS (ESI) m/e [M+1]$^+$ 270, 272.

Step 2: 5'-(3,5-Dimethylisoxazol-4-yl)spiro[[1,3]dioxolane-2,3'-indolin]-2'-one

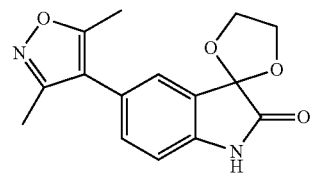

A mixture of 3,5-dimethylisoxazol-4-ylboronic acid (159 g, 1.13 mol), dichloro[1,1'-bis(di-tert-butylphosphino)ferrocene]palladium(II) (23.6 g, 29 mmol), 5'-bromospiro[[1,3]dioxolane-2,3'-indolin]-2'-one (236 g, 0.87 mol) and Na$_2$CO$_3$ (184 g, 1.7 mol) in dioxane/H$_2$O (1200 mL/300 mL) was heated to 110° C. for 12 h. The mixture was filtered through a pad of celite and concentrated in vacuo. The crude product was dissolved in CH$_2$Cl$_2$ (2 L), then hexane 2 L was added and the mixture was filtered again, the organic phase was concentrated in vacuo to give target product (150 g, 60%). $^1$H NMR (400 MHz, DMSO-d$_6$): $\delta_H$ 10.56 (s, 1H), 7.31-7.33 (m, 2H), 6.93 (d, J=8.0 Hz, 1H), 4.27-4.35 (m, 4H), 2.35 (s, 3H), 2.18 (s, 3H). MS (ESI) m/e [M+1]$^+$ 287.

Step 3: 5-(3,5-Dimethylisoxazol-4-yl)indoline-2,3-dione

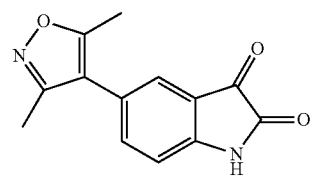 [SMILES: Cc1noc(C)c1-c1ccc2c(c1)C(=O)C(=O)N2]

A solution of compound 5'-(3,5-dimethylisoxazol-4-yl)spiro[[1,3]dioxolane-2,3'-indolin]-2'-one (150 g, 0.52 mol), acetic acid (10 mL), and concentrated HCl solution (300 mL) was heated to 90° C. After 1 h, the mixture was poured into ice-water, and the expected compound 5-(3,5-Dimethylisoxazol-4-yl)indoline-2,3-dione was collected by filtration and washed with water, EtOH, and EtOAc, and afforded target compound (115 g, 92%). $^1$H NMR (DMSO-d$_6$) $\delta_H$ 11.14 (s, 1H), 7.59 (d, J=8.0 Hz, 1H), 7.51 (s, 1H), 7.00 (d, J=8.0 Hz, 1H), 2.37 (s, 3H), 2.20 (s, 3H). MS (ESI) m/e [M+1]⁺ 243.

Step 4: 5-(3,5-dimethylisoxazol-4-yl)-3-hydroxy-3-phenylindolin-2-one

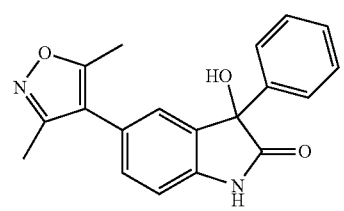

5-(3,5-Dimethylisoxazol-4-yl)indoline-2,3-dione (24.2 g, 0.1 mol) was dissolved in anhydrous THF (400 mL) and cooled to 0° C. followed by dropwise addition of a 2.0 M solution of PhMgBr in THF (110 mL, 220.0 mmol). The ice-bath was removed, and the reaction was stirred under N₂ for 30 min at which point TLC analysis indicated complete consumption of the starting material. The reaction mixture was quenched with saturated aqueous NH₄Cl (100 mL), and extracted with EtOAc (3×100 ml). The combined organic layers were washed with saturated aqueous NaHCO₃ (100 ml), brine (100 ml), dried over anhydrous MgSO₄, filtered, and concentrated in vacuo. The residue was evacuated under high vacuum to give the crude alcohol (30 g, 94%). ¹H NMR (400 MHz, DMSO-d₆): δ 10.50 (s, 1H), 7.22-7.32 (m, 6H), 7.09 (d, J=1.2 Hz, 1H), 6.99 (d, J=8.0 Hz, 1H), 6.71 (brs, 1H), 2.32 (s, 3H), 2.15 (s, 3H) MS (ESI) m/e [M+1]⁺ 321.

Compound 1.1a and 1.1b

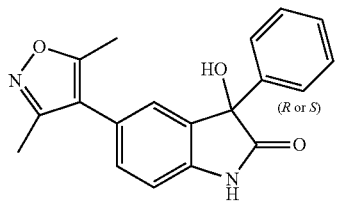

1.1a

Fast isomer in chiral AD HPLC
Eluting reagent: Hexane/EtOH = 4/1

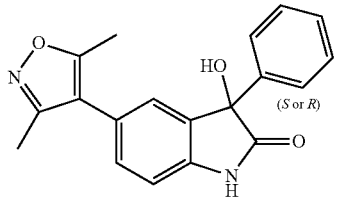

1.1b

Slow isomer in chiral AD HPLC
Eluting reagent: Hexane/EtOH = 4/1

Each enantiomer of racemic 1.1a and 1.1b was separated using preparative HPLC on a Chiralpak AD with 25% 2-propanol/hexane as an eluent. The enantiomeric excesses were determined by using HPLC on a Chiralpak AD with 25% 2-propanol/hexane as an eluent at a flow rate of 1.0 mL/min. The first one enantiomer eluted at the retention time of 5.8 min, and the other enantiomer eluted at the retention time of 7.4 min. The spectral properties of the title compounds were identical with those of 1.

The following compounds, compound 1.2 through 1.29 were synthesized starting from the corresponding Grignard reagent to the similar procedures described as those of compound 1.1.

| # | Name | ¹H NMR data LC/MS m/z (M + 1) | Structure |
|---|------|-------------------------------|-----------|
| 1.2 | 3-(4-chlorophenyl)-5-(3,5-dimethylisoxazol-4-yl)-3-hydroxyindolin-2-one | (DMSO-d₆) δ 10.53 (s, 1H), 7.23-7.53 (m, 5H), 7.07 (s, 1H) 6.96 (d, J = 8.0 Hz, 1H), 6.80 (s, 1H), 2.30 (s, 3H), 2.12 (s, 3H). MS (ESI) m/e [M + 1]⁺ 355. | 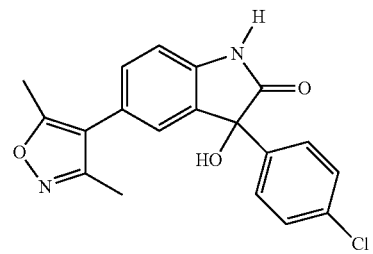 [SMILES: Cc1noc(C)c1-c1ccc2c(c1)C(O)(c1ccc(Cl)cc1)C(=O)N2] |
| 1.3 | 3-(3-chlorophenyl)-5-(3,5-dimethylisoxazol-4-yl)-3-hydroxyindolin-2-one | (DMSO-d₆) δ 10.61 (s, 1H), 7.11-7.44 (m, 5H), 7.02 (d, J = 8.0 Hz, 1H), 6.91 (s, 1H), 2.34 (s, 3H), 2.16 (s, 3H). MS (ESI) m/e [M + 1]⁺ 355. | 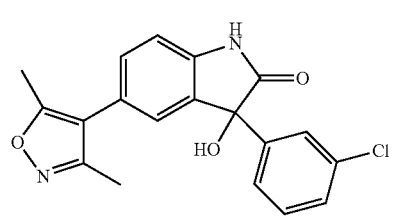 [SMILES: Cc1noc(C)c1-c1ccc2c(c1)C(O)(c1cccc(Cl)c1)C(=O)N2] |

-continued

| # | Name | ¹H NMR data LC/MS m/z (M + 1) | Structure |
|---|------|-------------------------------|-----------|
| 1.4 | 5-(3,5-dimethylisoxazol-4-yl)-3-(4-fluorophenyl)-3-hydroxyindolin-2-one | (DMSO-d₆) δ 10.05 (s, 1H), 7.12-7.35 (m, 6H), 7.00 (d, J = 8.0 Hz, 1H), 6.78 (s, 1H), 2.34 (s, 3H), 2.16 (s, 3H). MS (ESI) m/e [M + 1]⁺ 339. | 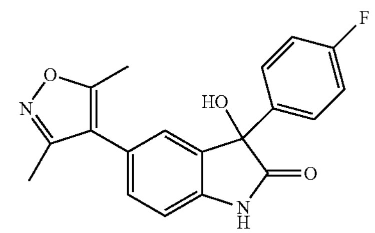 [SMILES: Cc1noc(C)c1-c1ccc2c(c1)C(O)(c1ccc(F)cc1)C(=O)N2] |
| 1.5 | 5-(3,5-dimethylisoxazol-4-yl)-3-hydroxy-3-p-tolylindolin-2-one | (DMSO-d₆) δ 10.53 (s, 1H), 7.14-7.32 (m, 6H), 7.04 (d, J = 8.0 Hz, 1H), 6.70 (s, 1H), 2.39 (s, 3H), 2.31 (s, 3H), 2.22 (s, 3H). MS (ESI) m/e [M + 1]⁺ 335. | 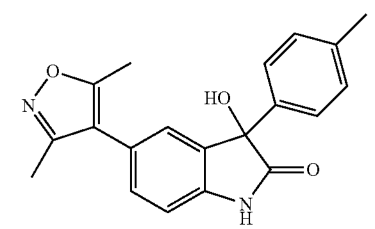 [SMILES: Cc1ccc(C2(O)C(=O)Nc3ccc(-c4c(C)noc4C)cc32)cc1] |
| 1.6 | 5-(3,5-dimethylisoxazol-4-yl)-3-(4-fluoro-3-methylphenyl)-3-hydroxyindolin-2-one | (DMSO-d₆) δ 10.51 (s, 1H), 7.00-7.28 (m, 6H), 6.73 (s, 1H), 2.34 (s, 3H), 2.20 (s, 3H), 2.16 (s, 3H). MS (ESI) m/e [M + 1]⁺ 353. | 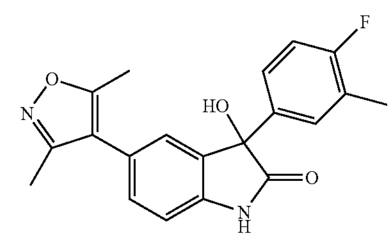 [SMILES: Cc1cc(C2(O)C(=O)Nc3ccc(-c4c(C)noc4C)cc32)ccc1F] |
| 1.7 | 5-(3,5-dimethylisoxazol-4-yl)-3-hydroxy-3-o-tolylindolin-2-one | (DMSO-d₆) δ 10.66 (s, 1H), 7.84 (d, J = 7.6 Hz, 1H), 6.72-7.26 (m, 7H), 2.27 (s, 3H), 2.09 (s, 3H), 1.85 (s, 3H). MS (ESI) m/e [M + 1]⁺ 335. | 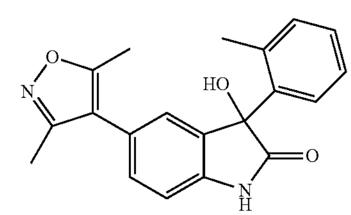 [SMILES: Cc1ccccc1C1(O)C(=O)Nc2ccc(-c3c(C)noc3C)cc21] |
| 1.8 | 3-(3,4-difluorophenyl)-5-(3,5-dimethylisoxazol-4-yl)-3-hydroxyindolin-2-one | (DMSO-d₆) δ 10.60 (s, 1H), 7.28-7.43 (m, 3H), 7.15 (s, 1H), 6.93-7.02 (m, 3H), 2.34 (s, 3H), 2.17 (s, 3H). MS (ESI) m/e [M + 1]⁺ 357. | 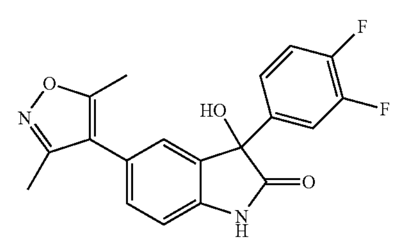 [SMILES: Cc1noc(C)c1-c1ccc2c(c1)C(O)(c1ccc(F)c(F)c1)C(=O)N2] |
| 1.9 | 5-(3,5-dimethylisoxazol-4-yl)-3-hydroxy-3-(4-methoxyphenyl)indolin-2-one | (DMSO-d₆) δ 10.45 (s, 1H), 7.20-7.27 (m, 3H), 7.11 (s, 1H), 6.98 (d, J = 8.0 Hz, 1H), 6.88 (d, J = 8.0 Hz, 2H), 6.62 (s, 1H), 3.71 (s, 3H), 2.34 (s, 3H), 2.17 (s, 3H). MS (ESI) m/e [M + 1]⁺ 351. | 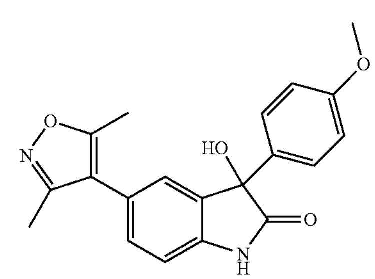 [SMILES: COc1ccc(C2(O)C(=O)Nc3ccc(-c4c(C)noc4C)cc32)cc1] |

| # | Name | ¹H NMR data LC/MS m/z (M + 1) | Structure |
|---|---|---|---|
| 1.10 | 3-(3,4-dimethoxyphenyl)-5-(3,5-dimethylisoxazol-4-yl)-3-hydroxyindolin-2-one | (DMSO-d₆) δ 10.45 (s, 1H), 7.27 (dd, J = 8.0, 1.2 Hz, 1H), 7.12-7.15 (m, 2H), 6.98 (d, J = 8.0 Hz, 1H), 6.85 (d, J = 8.0 Hz, 1H), 6.65 (s, 1H), 6.60 (d, J = 1.2 Hz, 1H), 3.73 (s, 3H), 3.70 (s, 3H), 2.34 (s, 3H), 2.17 (s, 3H). MS (ESI) m/e [M + 1]⁺ 381. | 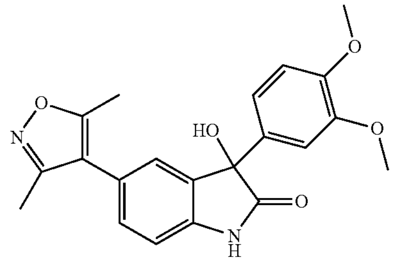 [SMILES: COc1ccc(C2(O)C(=O)Nc3ccc(-c4c(C)noc4C)cc32)cc1OC] |
| 1.11 | 5-(3,5-dimethylisoxazol-4-yl)-3-hydroxy-3-(naphthalen-1-yl)indolin-2-one | (DMSO-d₆) δ 10.81 (s, 1H), 7.95-7.93 (m, 4H), 7.25-7.44 (m, 4H), 6.93-7.10 (m, 3H), 2.24 (s, 3H), 2.03 (s, 3H). MS (ESI) m/e [M + 1]⁺ 371. | 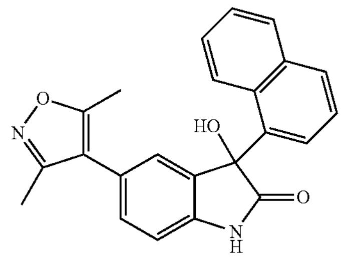 [SMILES: Cc1noc(C)c1-c1ccc2c(c1)C(O)(c1cccc3ccccc13)C(=O)N2] |
| 1.12 | 5-(3,5-dimethylisoxazol-4-yl)-3-hydroxy-3-(phenylethynyl)indolin-2-one | (DMSO-d₆) δ 10.69 (s, 1H), 7.28-7.46 (m, 6H), 7.18 (s, 1H) 6.96 (d, J = 8.0 Hz, 1H), 2.40 (s, 3H), 2.23 (s, 3H). MS (ESI) m/e [M + 1]⁺ 345. | 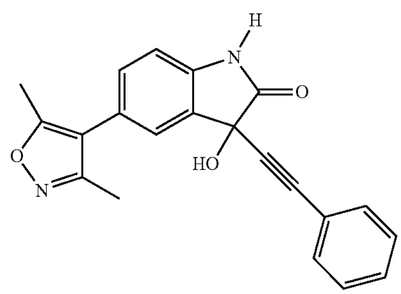 [SMILES: Cc1noc(C)c1-c1ccc2c(c1)C(O)(C#Cc1ccccc1)C(=O)N2] |
| 1.13 | 5-(3,5-dimethylisoxazol-4-yl)-3-hydroxy-3-(3-methylthiophen-2-yl)indolin-2-one | (DMSO-d₆) δ 10.60 (s, 1H), 7.28 (d, J = 5.6 Hz, 2H), 7.12 (s, 1H), 6.96-6.97 (m, 2H), 6.80 (d, J = 5.6 Hz, 1H), 2.34 (s, 3H), 2.16 (s, 3H), 1.88 (s, 3H). MS (ESI) m/e [M + 1]⁺ 341. | 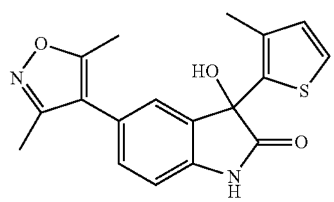 [SMILES: Cc1ccsc1C1(O)C(=O)Nc2ccc(-c3c(C)noc3C)cc21] |
| 1.14 | 3-cycloheptyl-5-(3,5-dimethylisoxazol-4-yl)-3-hydroxyindolin-2-one | (DMSO-d₆) δ 10.34 (s, 1H), 7.19 (d, J = 8.0 Hz, 1H), 6.87 (d, J = 8.0 Hz, 1H), 5.88 (s, 1H), 2.37 (s, 3H), 2.17 (s, 3H), 1.91-2.10 (m, 2H), 1.71-1.73 (m, 1H), 1.23-1.53 (m, 9H), 0.80-0.85 (m, 1H). MS (ESI) m/e [M + 1]⁺ 327. | 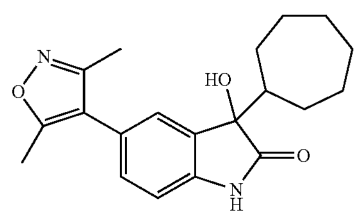 [SMILES: Cc1noc(C)c1-c1ccc2c(c1)C(O)(C1CCCCCC1)C(=O)N2] |
| 1.15 | 3-cyclohexyl-5-(3,5-dimethylisoxazol-4-yl)-3-hydroxyindolin-2-one | (DMSO-d₆) δ 10.26 (s, 1H), 7.14-7.17 (m, 2H), 6.83 (d, J = 7.6 Hz, 1H), 2.35 (s, 3H), 2.34 (m, 1H), 2.17 (s, 3H), 1.48-1.83 (m, 6H), 1.02-1.09 (m, 4H). MS (ESI) m/e [M + 1]⁺ 327. | 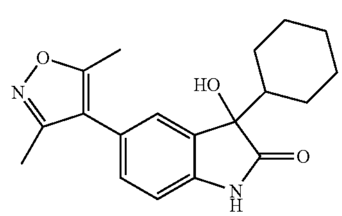 [SMILES: Cc1noc(C)c1-c1ccc2c(c1)C(O)(C1CCCCC1)C(=O)N2] |

-continued

| # | Name | ¹H NMR data LC/MS m/z (M + 1) | Structure |
|---|------|-------------------------------|-----------|
| 1.16 | 5-(3,5-dimethylisoxazol-4-yl)-3-hydroxy-3-(tetrahydro-2H-pyran-4-yl)indolin-2-one | (DMSO-d₆) δ 10.37 (s, 1H), 7.20-7.22 (m, 2H), 6.89 (d, J = 8.4 Hz, 1H), 5.96 (s, 1H), 3.78-3.87 (m, H), 3.19-3.21 (m, 2H), 2.38 (s, 3H), 2.21 (s, 3H), 2.02-2.04 (m, 1H), 1.60-1.63 (m, 1H), 1.36-1.40 (m, 2H), 1.05-1.09 (m, 1H). MS (ESI) m/e [M + 1]⁺ 329. | 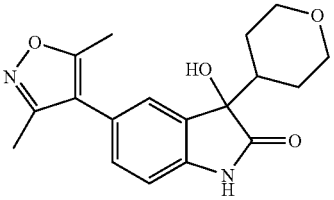 [SMILES: Cc1noc(C)c1-c1ccc2c(c1)C(O)(C1CCOCC1)C(=O)N2] |
| 1.17 | 3-cyclopentyl-5-(3,5-dimethylisoxazol-4-yl)-3-hydroxyindolin-2-one | (DMSO-d₆) δ 10.28 (s, 1H), 7.18-7.24 (m, 2H), 6.88 (d, J = 8.0 Hz, 1H), 2.37 (s, 3H), 2.35-2.36 (m, 1H), 2.19 (s, 3H), 1.21-1.64 (m, 8H). MS (ESI) m/e [M + 1]⁺ 313. | 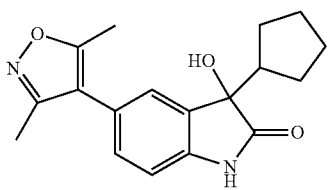 [SMILES: Cc1noc(C)c1-c1ccc2c(c1)C(O)(C1CCCC1)C(=O)N2] |
| 1.18 | 3-cyclobutyl-5-(3,5-dimethylisoxazol-4-yl)-3-hydroxyindolin-2-one | (DMSO-d₆) δ 10.27 (s, 1H), 7.20-7.21 (m, 2H), 6.89 (d, J = 8.0 Hz, 1H), 5.87 (s, 1H), 2.60-2.61 (m, 1H), 2.38 (s, 3H), 2.21 (s, 3H), 2.03-2.27 (m, 2H), 1.59-1.77 (m, 4H). MS (ESI) m/e [M + 1]⁺ 299. | 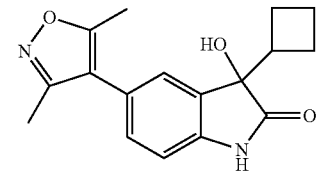 [SMILES: Cc1noc(C)c1-c1ccc2c(c1)C(O)(C1CCC1)C(=O)N2] |
| 1.19 | 3-cyclopropyl-5-(3,5-dimethylisoxazol-4-yl)-3-hydroxyindolin-2-one | (DMSO-d₆) δ 10.28 (s, 1H), 7.18-7.21 (m, 2H), 6.87 (d, J = 8.0 Hz, 1H), 5.92 (s, 1H), 2.37 (s, 3H), 2.20 (s, 3H), 1.10-1.19 (m, 1H), 0.13-00.57 (m, 4H). MS (ESI) m/e [M + 1]⁺ 285. | 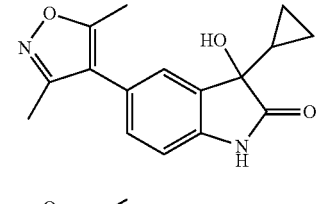 |
| 1.20 | 5-(3,5-dimethylisoxazol-4-yl)-3-ethyl-3-hydroxyindolin-2-one | (DMSO-d₆) δ 10.33 (s, 1H), 7.19-7.23 (m, 2H), 6.89 (d, J = 8.0 Hz, 1H), 5.91 (s, 1H), 2.38 (s, 3H), 2.20 (s, 3H), 1.77-1.84 (m, 2H), 0.66 (t, J = 7.6 Hz, 3H). MS (ESI) m/e [M + 1]⁺ 273. | 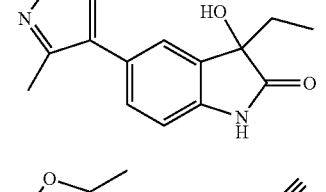 |
| 1.21 | 5-(3,5-dimethylisoxazol-4-yl)-3-ethynyl-3-hydroxyindolin-2-one | (DMSO-d₆) δ 10.64 (s, 1H), 7.35 (s, 1H), 7.27 (dd, J = 8.0, 1.2 Hz, 1H), 7.04 (s, 1H), 6.93 (d, J = 8.0vHz, 1H), 3.62 (s, 1H), 2.38 (s, 3H), 2.21 (s, 3H). MS (ESI) m/e [M + 1]⁺ 269. | 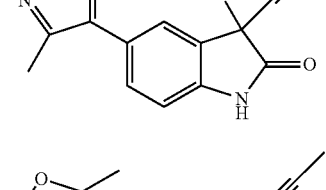 |
| 1.22 | 5-(3,5-dimethylisoxazol-4-yl)-3-hydroxy-3-(prop-1-ynyl)indolin-2-one | (DMSO-d₆) δ 10.56 (s, 1H), 7.32 (s, 1H), 7.24 (d, J = 8.0 Hz, 1H), 6.91 (d, J = 8.0 Hz, 1H), 6.84 (s, 1H), 2.39 (s, 3H), 2.21 (s, 3H), 1.81 (s, 3H). MS (ESI) m/e [M + 1]⁺ 283. | 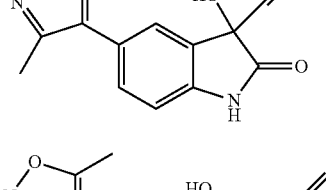 |
| 1.23 | 3-allyl-5-(3,5-dimethylisoxazol-4-yl)-3-hydroxyindolin-2-one | (DMSO-d₆) δ 10.34 (s, 1H), 7.23 (s, 1H), 7.19 (d, J = 8.0 Hz, 1H), 6.87 (d, J = 8.0 Hz, 1H), 6.06 (s, 1H), 5.03-5.55 (m, 1H), 4.94-4.98 (m, 2H), 2.57-2.59 (m, 1H), 2.48-2.50 (m, 1H), 2.37 (s, 3H), 2.19 (s, 3H). MS (ESI) m/e [M + 1]⁺ 285. | 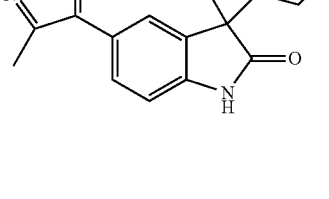 |

| # | Name | ¹H NMR data LC/MS m/z (M + 1) | Structure |
|---|------|-------------------------------|-----------|
| 1.24 | 3-(but-3-enyl)-5-(3,5-dimethylisoxazol-4-yl)-3-hydroxyindolin-2-one | (DMSO-d₆) δ 10.36 (s, 1H), 7.26 (s, 1H), 7.21 (d, J = 8.0 Hz, 1H), 6.90 (d, J = 8.0 Hz, 1H), 5.98 (s, 1H), 5.68-5.69 (m, 1H), 4.85-4.92 (m, 2H), 2.38 (s, 3H), 2.21 (s, 3H), 1.84-1.88 (m, 4H). MS (ESI) m/e [M + 1]⁺ 285. | 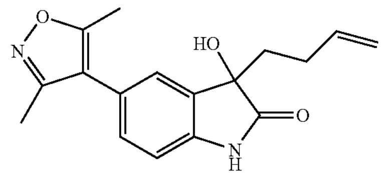 [SMILES: C=CCCC1(O)C(=O)Nc2ccc(-c3c(C)noc3C)cc21] |
| 1.25 | 5-(3,5-dimethylisoxazol-4-yl)-3-hydroxy-3-(pent-4-enyl)indolin-2-one | (DMSO-d₆) δ 10.33 (s, 1H), 7.21-7.32 (m, 2H), 6.89 (d, J = 8.0 Hz, 1H), 5.92 (s, 1H), 5.66-5.72 (m, 1H), 4.88-4.95 (m, 2H), 2.37 (s, 3H), 2.20 (s, 3H), 1.85-1.90 (m, 4H), 1.00-1.19 (m, 2H). MS (ESI) m/e [M + 1]⁺ 312. | 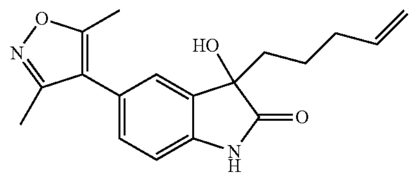 [SMILES: C=CCCCC1(O)C(=O)Nc2ccc(-c3c(C)noc3C)cc21] |
| 1.26 | 3-tert-butyl-5-(3,5-dimethylisoxazol-4-yl)-3-hydroxyindolin-2-one | (DMSO-d₆) δ 10.25 (s, 1H), 7.17-7.20 (m, 2H), 6.86 (d, J = 8.0 Hz, 1H), 5.76 (s, 1H), 2.37 (s, 3H), 2.20 (s, 3H), 0.97 (s, 9H). MS (ESI) m/e [M + 1]⁺ 301. | 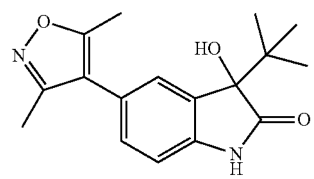 [SMILES: Cc1noc(C)c1-c1ccc2c(c1)C(O)(C(C)(C)C)C(=O)N2] |
| 1.27 | 5-(3,5-dimethylisoxazol-4-yl)-3-hydroxy-3-isopropylindolin-2-one | (DMSO-d₆) δ 10.33 (s, 1H), 7.18-7.22 (m, 2H), 6.89 (d, J = 8.0 Hz, 1H), 5.88 (s, 1H), 2.38 (s, 3H), 2.20 (s, 3H), 2.08-2.12 (m, 1H), 0.98 (d, J = 6.8 Hz, 3H), 0.68 (d, J = 6.8 Hz, 3H). MS (ESI) m/e [M + 1]⁺ 287. | 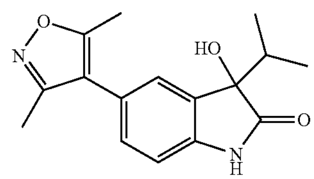 [SMILES: Cc1noc(C)c1-c1ccc2c(c1)C(O)(C(C)C)C(=O)N2] |
| 1.28 | 5-(3,5-dimethylisoxazol-4-yl)-3-hydroxy-2-(2-methylallyl)indolin-2-one | (DMSO-d₆) δ 10.33 (s, 1H), 7.25 (s, 1H), 7.18 (d, J = 8.0 Hz, 1H), 6.89 (d, J = 8.0 Hz, 1H), 6.03 (s, 1H), 4.66 (s, 1H), 4.52 (s, 1H), 2.50-2.66 (m, 2H), 2.36 (s, 3H), 2.18 (s, 3H), 1.46 (s, 3H). MS (ESI) m/e [M + 1]⁺ 299. | 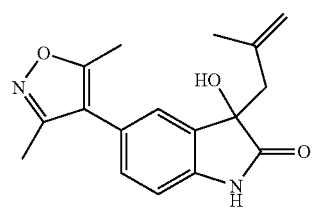 [SMILES: C=C(C)CC1(O)C(=O)Nc2ccc(-c3c(C)noc3C)cc21] |
| 1.29 | 5-(3,5-dimethylisoxazol-4-yl)-3-hydroxy-3-(3-phenylpropyl)indolin-2-one | (DMSO-d₆) δ 10.32 (s, 1H), 7.06-7.22 (m, 7H), 6.88 (d, J = 8.0 Hz, 1H), 5.92 (s, 1H), 2.35 (s, 3H), 2.18 (s, 3H), 1.75-1.83 (m, 2H), 1.25-1.42 (m, 4H). MS (ESI) m/e [M + 1]⁺ 363. | 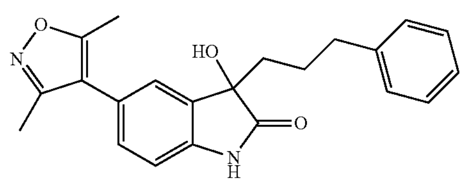 [SMILES: Cc1noc(C)c1-c1ccc2c(c1)C(O)(CCCc1ccccc1)C(=O)N2] |

Compound 1.30a and 1.30b

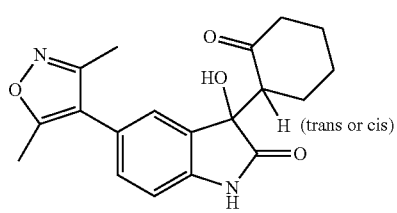

1.30a

Fast isomer in normal chromatography
Eluting reagent: PE/EtOAc = 1/1

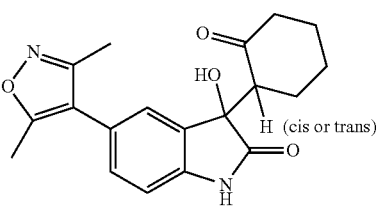

1.30b

Slow isomer in normal chromatography
Eluting reagent: PE/EtOAc = 1/1

5-(3,5-Dimethylisoxazol-4-yl)-3-hydroxy-3-(2-oxo-cyclohexyl)indolin-2-one 5-(3,5-dimethylisoxazol-4-yl)indoline-2,3-dione (242 mg, 1.0 mmol) is dissolved in MeOH (20 ml), cyclohexanone (196 mg, 2.0 mmol) and dimethylamine (0.4 mmol) are added and the reaction mixture is stirred for 4 h at room temperature. After that, the mixture is concentrated in vacuo and the residue was purified with chromatography on column to give two isomers (The first 50 mg, 14.7%, the second 30 mg, 8.8% and mixture 100 mg, 29.3%). The fast isomer (50 mg, 14.7%): $^1$H NMR (400 MHz, DMSO-$d_6$): δ 10.25 (s, 1H), 7.29 (d, J=1.6 Hz, 1H), 7.17 (dd, J=1.6, 8.0 Hz, 1H), 6.84 (d, J=8.0 Hz, 1H), 5.83 (s, 1H), 3.32-3.41 (m, 1H), 2.30-2.40 (m, 5H), 2.19 (s, 3H), 1.98-2.06 (m, 2H), 1.80-1.83 (m, 2H), 1.44-1.64 (m, 2H), MS (ESI) m/e [M+1]$^+$ 341.0; the slow isomer (30 mg, 8.8%): $^1$H NMR (400 MHz, DMSO-$d_6$): δ 10.31 (s, 1H), 7.16-7.20 (m, 2H), 6.88 (d, J=8.0 Hz, 1H), 5.92 (s, 1H), 3.08-3.12 (m, 1H), 2.59-2.62 (m, 1H), 2.36 (s, 3H), 2.29-2.35 (m, 1H), 2.19 (s, 3H), 1.77-2.00 (m, 4H), 1.62-1.68 (m, 1H), 1.42-1.50 (m, 1H), MS (ESI) m/e [M+1]$^+$ 341.

Compound 1.31

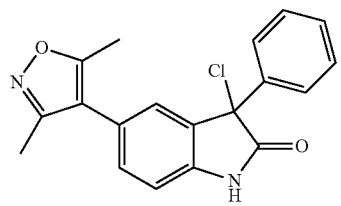

3-Chloro-5-(3,5-dimethylisoxazol-4-yl)-3-phenylindolin-2-one

To a solution of 5-(3,5-dimethylisoxazol-4-yl)-3-hydroxy-3-phenylindolin-2-one (30 g, 0.094 mol) in THF (300 mL) was added pyridine (40 mL) followed by SOCl$_2$ (20 mL) at 0° C. The reaction mixture was stirred at 0° C. for 0.5 h and quenched by the addition of saturated ammonium chloride solution (50 mL). The organic layer was washed with saturated ammonium chloride (2×50 mL). The combined aqueous layers were extracted with CH$_2$Cl$_2$ (200 mL). The combined organic layers was dried over anhydrous sodium sulfate and filtered. The filtrate was concentrated in vacuo to afford target compound (25 g, 79%). $^1$H NMR (400 MHz, DMSO-$d_6$): δ 11.11 (s, 1H), 7.37-7.53 (m, 6H), 7.08 (d, J=8.0 Hz, 1H), 2.30 (s, 3H), 2.20 (s, 3H).

Compound 1.32

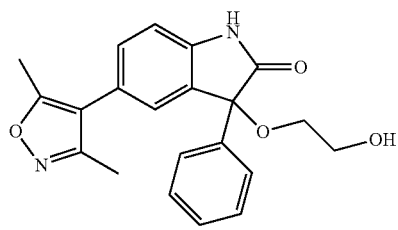 [SMILES: Cc1noc(C)c1-c1ccc2c(c1)C(OCCO)(c1ccccc1)C(=O)N2]

5-(3,5-Dimethylisoxazol-4-yl)-3-(2-hydroxyethoxy)-3-phenylindolin-2-one 30 mg (0.088 mmol) of 3-chloro-5-(3,5-dimethylisoxazol-4-yl)-3-phenylindolin-2-one and 139 mg (0.176 mmol) of pyridine were dissolved in 5 ml of THF. After the addition of 54 mg (0.88 mmol) of ethane-1,2-diol, the reaction solution was stirred for 5 h at room temperature. Subsequently, the solution was diluted with water. The aqueous phase was extracted with 2×25 mL of EtOAc. The combined organic phases were washed with aqueous NaHCO$_3$ and with water, dried and concentrated in vacuo. The resulting residue was purified by Pre-TLC (eluent: Hexane/EtOAc=1/1) to give product (5 mg, 15%) as a white solid. $^1$H NMR (400 MHz, DMSO-$d_6$): δ 10.77 (s, 1H), 7.32-7.35 (m, 6H), 7.20 (s, 1H), 7.04 (d, J=8.0 Hz, 1H), 4.65 (t, J=5.6 Hz, 1H), 3.23-3.52 (m, 4H), 2.35 (s, 3H), 2.18 (s, 3H). MS (ESI) m/e [M+1]$^+$ 365.

Compound 1.33

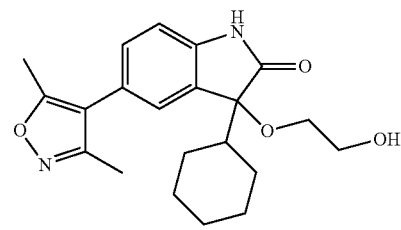 [SMILES: Cc1noc(C)c1-c1ccc2c(c1)C(OCCO)(C1CCCCC1)C(=O)N2]

3-Cyclohexyl-5-(3,5-dimethylisoxazol-4-yl)-3-(2-hydroxyethoxy)indolin-2-one

Compound 3-cyclohexyl-5-(3,5-dimethylisoxazol-4-yl)-3-(2-hydroxyethoxy)indolin-2-one was synthesized according the procedure of compound 1.32. $^1$H NMR (400 MHz, DMSO-$d_6$): δ 10.59 (s, 1H), 7.27 (d, J=8.0 Hz, 1H), 7.21 (s, 1H), 6.92 (d, J=8.0 Hz, 1H), 4.49 (t, J=5.6 Hz, 1H), 3.37-3.43 (m, 2H), 2.93-3.13 (m, 2H), 2.40 (s, 3H), 2.22 (s, 3H), 1.82-1.90 (m, 2H), 1.56-1.70 (m, 4H), 0.94-1.15 (m, 4H), 0.74-0.78 (m, 1H). MS (ESI) m/e [M+1]$^+$ 365.

Compound 1.34

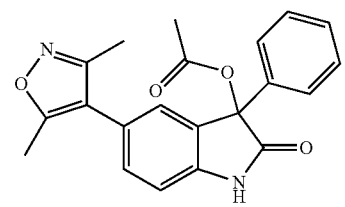 [SMILES: CC(=O)OC1(c2ccccc2)C(=O)Nc2ccc(-c3c(C)noc3C)cc21]

5-(3,5-Dimethylisoxazol-4-yl)-2-oxo-3-phenylindolin-3-yl acetate

To a solution of 3-chloro-5-(3,5-dimethylisoxazol-4-yl)-3-phenylindolin-2-one (50 mg, 0.15 mmol) in dioxane (2 mL) was added sodium acetate (90 mg, 1.1 mmol), the reaction mixture was stirred at 85° C. for 6 h and quenched by the addition of saturated ammonium chloride solution (10 mL). The organic layer was extracted with CH$_2$Cl$_2$ (2×20 mL). The combined organic layers was dried over anhydrous sodium sulfate and filtered. The filtrate was concentrated in vacuo to afford crude product, ant it was purified by Pre-TLC (eluent: Hexane/EtOAc=1/1) to give product (20 mg, 37%) as a white solid. $^1$H NMR (400 MHz, DMSO-$d_6$): δ 10.78 (s, 1H), 7.33-7.38 (m, 6H), 7.25 (s, 1H), 7.01 (d, J=8.0 Hz, 1H), 2.35 (s, 3H), 2.18 (s, 3H), 2.15 (s, 3H). MS (ESI) m/e [M+1]$^+$ 363.

Example 2
Synthesis of Compound 2.1-2.58

Compound 2.1

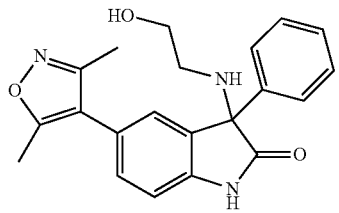 [SMILES: Cc1noc(C)c1-c1ccc2c(c1)C(NCCO)(c1ccccc1)C(=O)N2]

5-(3,5-di methylisoxazol-4-yl)-3-(2-hydroxyethylamino)-3-phenylindolin-2-one 34 mg (0.1 mmol) of 3-chloro-5-(3,5-dimethylisoxazol-4-yl)-3-phenylindolin-2-one and 86 mg (10 mmol) of 2-aminoethanol were solved in THF (5 mL), the reaction solution was stirred for 16 h at room temperature. Subsequently, the solution was diluted with water. The aqueous phase was extracted with CH$_2$Cl$_2$ (2×10 mL). The combined organic phases were washed with aqueous NaHCO$_3$ and with water, dried and concentrated in vacuo. The resulting residue was purified by silicon gel chromatography (eluent: EtOAc/MeOH=50/1) to give product (20 mg, 55%) as a white solid. $^1$H NMR (400 MHz, DMSO-d$_6$): δ 10.67 (s, 1H), 7.44 (d, J=8.0 Hz, 1H), 7.18-7.34 (m, 5H), 7.18 (s, 1H), 6.99 (d, J=8.0 Hz, 1H), 4.51 (t, J=5.6 Hz, 1H), 3.40-3.42 (m, 2H), 2.96-2.99 (m, 1H), 2.40-2.42 (m, 1H), 2.35 (s, 3H), 2.27-2.29 (m, 1H), 2.17 (s, 3H). MS (ESI) m/e [M+1]$^+$ 364.

Compound 2.2

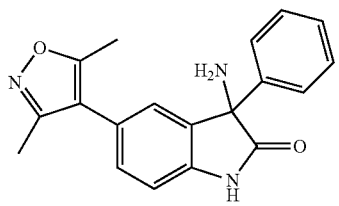 [SMILES: Cc1noc(C)c1-c1ccc2c(c1)C(N)(c1ccccc1)C(=O)N2]

Step 1: 5-bromo-3-hydroxy-3-phenylidolin-2-one

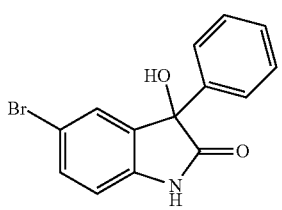 [SMILES: O=C1Nc2ccc(Br)cc2C1(O)c1ccccc1]

To a mixture of 5-bromoindoline-2,3-dione (94 g, 416 mmol, 1.0 eq) in THF (1 L) was added dropwise a solution of phenylmagnesium chloride in THF (2.0 M, 500 mL, 1.0 mol, 2.4 eq) at 0° C., the reaction mixture was stirred for 2 hours at room temperature. Then the mixture was quenched with sat. NH$_4$Cl.aq, washed with brine, dried over Na$_2$SO$_4$, and the solvent was removed to give crude product. Then the crude product was stirred in PE/EA for 1.0 h, the solid was collected by filter and dried in the air to give 77 g (Yield 61%) product. $^1$H NMR (400 MHz, DMSO-d$_6$): δ$_H$ 10.57 (s, 1H), 7.42-7.45 (dd, 1H, J=8.4, 2.0 Hz), 7.26-7.36 (m, 5H), 7.20-7.21 (d, 1H, J=2.0 Hz), 6.87-6.89 (d, 1H, J=8.0 Hz), 6.78 (s, 1H).

Step 2: 5-(3,5-dimethylisoxazol-4-yl)-3-hydroxy-3-phenylindolin-2-one

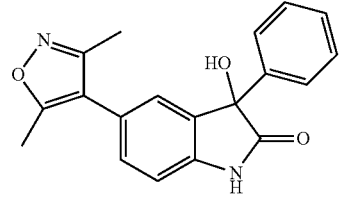 [SMILES: Cc1noc(C)c1-c1ccc2c(c1)C(O)(c1ccccc1)C(=O)N2]

Under N$_2$, a mixture of 3,5-dimethylisoxazol-4-ylboronic acid (28 g, 200 mmol, 1.5 eq), dichloro[1,1'-bis(di-tert-butylphosphino)ferrocene]palladium(II) (4.5 g, 6.1 mmol, 0.05 eq), 5-bromo-3-hydroxy-3-phenylindolin-2-one (40 g, 132 mmol, 1.0 eq) and Na$_2$CO$_3$ (45 g, 425 mmol, 3.2 eq) in dioxane/H$_2$O (500 mL/120 mL) was heated to reflux for 5 h. After cooled down, 500 mL EA was added, the mixture was filtered through a pad of celite, the filter was washed with brine (500 mL×2), dried over Na$_2$SO$_4$, concentrated, purified by sili-gel to give product 27.7 g (yield, 65.6%). $^1$H NMR (400 MHz, DMSO-d$_6$): δ$_H$ 10.51 (s, 1H), 7.25-7.34 (m, 6H), 7.10 (m, 1H), 6.99-7.01 (d, 1H, J=8.0 Hz), 6.72 (s, 1H), 2.33 (s, 3H), 2.16 (s, 3H). MS (ESI) m/e [M+1]$^+$ 321.

Step 3: 3-amino-5-(3,5-dimethylisoxazol-4-yl)-3-phenylindolin-2-one

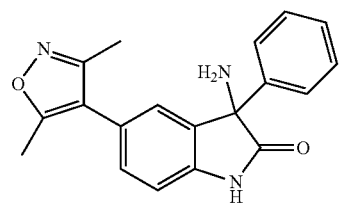 [SMILES: Cc1noc(C)c1-c1ccc2c(c1)C(N)(c1ccccc1)C(=O)N2]

Under N$_2$, to a solution of 5-(3,5-dimethylisoxazol-4-yl)-3-hydroxy-3-phenylindolin-2-one (21 g, 65.6 mmol, 1.0 eq) in THF (300 mL) was added dropwise pyridine (30 mL) and SOCl$_2$ (15 mL) at −15° C.~−20° C., the mixture was stirred for 20 min at −15° C.~−20° C., quenched with brine (50 mL), washed with brine (300 mL×2), the organic phase was concentrated to give 17.5 g crude product. The crude product was dissolved in NH$_3$/MeOH (7M, 200 mL), and stirred for 2 hours at room temperature. Then the solvent was removed in vacuo to give crude product, which was dissolved in EA (200 mL), washed with water (100 mL), then brine (100 mL), dried over Na$_2$SO$_4$, concentrated to give 15 g crude product, which was purified by sili-gel to give 8.5 g (yield 40%) product as white solid. $^1$H NMR (DMSO-d$_6$) δ$_H$ 10.53 (s, 1H), 7.39-7.41 (d, 2H, J=8.0 Hz), 7.29-7.33 (t, 2H, J=8.0 Hz), 7.21-7.26 (m, 2H), 7.14 (s, 1H), 6.98-7.00 (d, 1H, J=8.0 Hz), 2.75 (s, 2H), 2.33 (s, 3H), 2.16 (s, 3H)

Compound 2.2a and 2.2b 2.2a

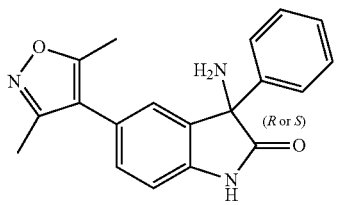

Fast isomer in chiral ASH HPLC
Eluting reagent: CO$_2$/MeOH/DEA = 70/30/0.1

-continued 2.2b

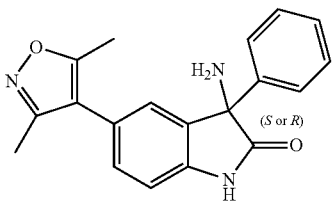

Slow isomer in chiral ASH HPLC
Eluting reagent: CO$_2$/MeOH/DEA = 70/30/0.1

Each enantiomer of racemic 2.2a and 2.2b was separated using preparative HPLC on a CHIRALPAK ASH with CO$_2$/MeOH/DEA=70/30/0.1 as an eluent. The enantiomeric excesses were determined by using HPLC on a CHIRALPAK ASH with CO$_2$/MeOH/DEA=60/40/0.1 (v/v/v) as an eluent at a flow rate of 2.0 mL/min. The first one enantiomer eluted at the retention time of 4.84 min, (DMSO-d$_6$) $\delta_H$ 10.53 (s, 1H), 7.20-7.41 (m, 6H), 7.13 (d, J=1.6 Hz, 1H), 6.99 (d, J=8.0 Hz, 1H), 2.71 (br s, 2H), 2.32 (s, 3H), 2.15 (s, 3H); and the other enantiomer eluted at the retention time of 6.91 min, (DMSO-d$_6$) $\delta_H$ 10.53 (s, 1H), 7.20-7.41 (m, 6H), 7.13 (d, J=2.0 Hz, 1H), 6.99 (d, J=8.0 Hz, 1H), 2.71 (br s, 2H), 2.33 (s, 3H), 2.16 (s, 3H). MS (ESI) m/e [M+1]$^+$ 320. The following compounds, Compound 2.3 through 2.37, were synthesized starting from the corresponding reagent to the similar procedures described as those of Compound 2.1.

| # | Name | $^1$H NMR data LC/MS m/z (M + 1) | Structure |
|---|---|---|---|
| 2.3 | 5-(3,5-dimethylisoxazol-4-yl)-3-phenyl-3-(piperidin-1-yl)indolin-2-one | (DMSO-d$_6$) δ 10.64 (s, 1H), 7.22-7.49 (m, 7H), 6.95 (d, J = 8.0 Hz, 1H), 2.45-2.50 (m, 4H), 2.37 (s, 3H), 2.19 (s, 3H), 1.36-1.48 (m, 6H). MS (ESI) m/e [M + 1]$^+$ 388. | 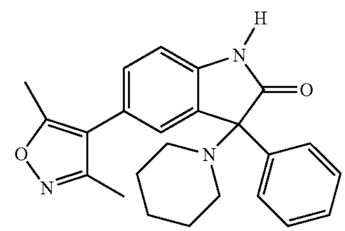 [SMILES: Cc1noc(C)c1-c1ccc2c(c1)C(c1ccccc1)(N1CCCCC1)C(=O)N2] |
| 2.4 | 5-(3,5-dimethylisoxazol-4-yl)-3-(4-hydroxypiperidin-1-yl)-3-phenylindolin-2-one | (DMSO-d$_6$) $\delta_H$ 10.65 (s, 1H), 7.49 (d, J = 7.6 Hz, 2H), 7.34 (t, J = 7.6 Hz, 2H), 7.31-7.19 (m, 3H), 6.96 (d, J = 7.6 Hz, 1H), 4.52 (d, J = 4.4 Hz, 1H), 3.41 (m, 1H), 2.67 (m, 2H), 2.12-2.41 (m, 8H), 1.66-1.70 (s, 2H), 1.37-1.40 (m, 2H). MS (ESI) m/e [M + 1]$^+$ 404. | 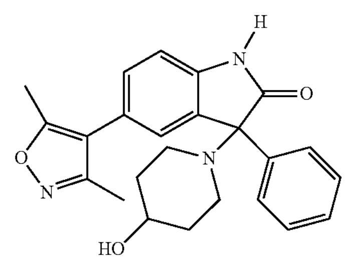 [SMILES: Cc1noc(C)c1-c1ccc2c(c1)C(c1ccccc1)(N1CCC(O)CC1)C(=O)N2] |
| 2.5 | 5-(3,5-dimethylisoxazol-4-yl)-3-(4-methylpiperazin-1-yl)-3-phenylindolin-2-one | (DMSO-d$_6$) $\delta_H$ 10.69 (s, 1H), 7.23-7.50 (m, 7H), 6.97 (d, J = 8.0 Hz, 1H), 2.49-2.50 (m, 4H), 2.36 (s, 3H), 2.34-2.35 (m, 4H), 2.19 (s, 3H), 2.17 (s, 3H). MS (ESI) m/e [M + 1]$^+$ 403. | 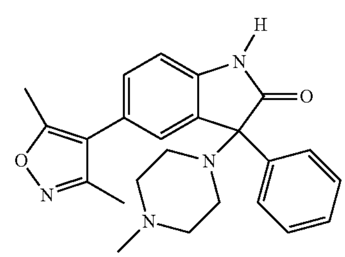 [SMILES: Cc1noc(C)c1-c1ccc2c(c1)C(c1ccccc1)(N1CCN(C)CC1)C(=O)N2] |
| 2.6 | 5-(3,5-dimethylisoxazol-4-yl)-3-morpholino-3-phenylindolin-2-one | (DMSO-d$_6$) $\delta_H$ 10.74 (s, 1H), 7.52 (d, J = 8.0 Hz, 2H), 7.24-7.38 (m, 5H), 6.97 (d, J = 8.0 Hz, 1H), 3.56 (s, 4H), 2.49 (s, 4H), 2.36 (s, 3H), 2.19 (s, 3H). MS (ESI) m/e [M + 1]$^+$ 390. | 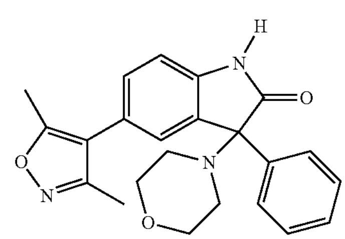 [SMILES: Cc1noc(C)c1-c1ccc2c(c1)C(c1ccccc1)(N1CCOCC1)C(=O)N2] |

| # | Name | ¹H NMR data LC/MS m/z (M + 1) | Structure |
|---|------|-------------------------------|-----------|
| 2.7a | 5-(3,5-dimethylisoxazol-4-yl)-3-((R)-2-hydroxy-1-phenylethylamino)-3-phenylindolin-2-on | (DMSO-d₆) δ$_H$ 10.22 (s, 1H), 7.45-7.48 (m, 2H), 7.21-7.33 (m, 4H), 7.06-7.16 (m, 6H), 6.87 (d, J = 7.6 Hz, 1H), 4.83 (t, J = 5.6 Hz, 1H), 3.55-3.59 (m, 1H), 3.36-3.42 (m, m1H), 2.37 (s, 3H), 2.20 (s, 3H). MS (ESI) m/e [M + 1]⁺ 440. | 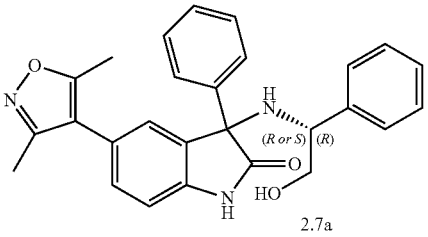<br>2.7a<br>Fast isomer in normal chromatography<br>Eluting reagent: DCM-MeOH = 100/1~20/1 |
| 2.7b | 5-(3,5-dimethylisoxazol-4-yl)-3-((R)-2-hydroxy-1-phenylethylamino)-3-phenylindolin-2-one | (DMSO-d₆) δ$_H$ 10.75 (s, 1H), 7.49-7.52 (m, 2H), 7.25-7.36 (m, 3H), 6.90-7.08 (m, 6H), 6.79 (d, J = 8.0 Hz, 1H), 6.49 (s, 1H), 4.89 (t, J = 5.6 Hz, 1H), 3.47-3.50 (m, 2H), 3.33-3.44 (m, 2H), 2.08 (s, 3H), 1.91 (s, 3H). MS (ESI) m/e [M + 1]⁺ 440. | 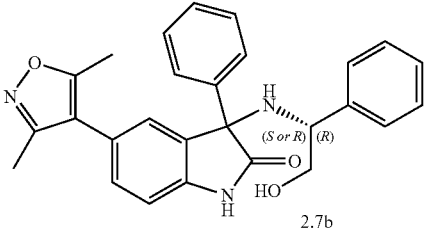<br>2.7b<br>Slow isomer in normal chromatography<br>Eluting reagent: DCM-MeOH = 100/1~20/1 |
| 2.8a | 5-(3,5-dimethylisoxazol-4-yl)-3-((S)-2-hydroxy-1-phenylethylamino)-3-phenylindolin-2-one | (DMSO-d₆) δ$_H$ 10.22 (s, 1H), 7.45-7.48 (m, 2H), 7.21-7.34 (m, 4H), 7.06-7.14 (m, 6H), 6.87 (d, J = 7.6 Hz, 1H), 4.82 (bs, 1H), 3.56-3.59 (m, 1H), 3.37-3.43 (m, 2H), 2.37 (s, 3H), 2.19 (s, 3H). MS (ESI) m/e [M + 1]⁺ 440. | 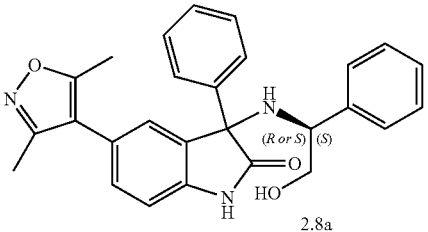<br>2.8a<br>Fast isomer in normal chromatography<br>Eluting reagent: DCM/MeOH = 100/1~20/1 |
| 2.8b | 5-(3,5-dimethylisoxazol-4-yl)-3-((S)-2-hydroxy-1-phenylethylamino)-3-phenylindolin-2-one | (DMSO-d₆) δ$_H$ 10.81 (s, 1H), 7.50-7.53 *(m, 2H), 7.27-7.38 (m, 3H), 7.07-7.09 (m, 2H), 6.94-7.02 (m, 4H), 6.80 (d, J = 8.4 Hz, 1H), 6.58 (s, 1H), 4.25 (bs, 2H), 3.39-3.57 (m, 3H), 2.11 (s, 3H), 1.94 (s, 3H). MS (ESI) m/e [M + 1]⁺ 440. | 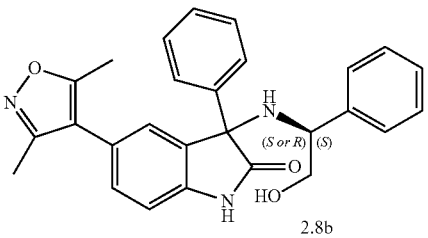<br>2.8b<br>Slow isomer in normal chromatography<br>Eluting reagent: DCM-MeOH = 100/1~20/1 |
| 2.9a | 5-(3,5-dimethylisoxazol-4-yl)-3-((S)-1-hydroxypropan-2-ylamino)-3-phenylindolin-2-one | (DMSO-d₆) δ$_H$ 10.65 (s, 1H), 7.45-7.47 (m, 2H), 7.22-7.32 (m, 4H), 7.19 (s, 1H), 6.98 (d, J = 8.4 Hz, 1H), 4.41 (t, J = 5.6 Hz, 1H), 3.16-03.22 (m, 1H), 3.02-3.09 (m, 1H), 2.65 (d, J = 4.2 Hz, 1H), 2.36 (s, 3H), 2.18 (s, 3H), 1.79-1.84 (m, 1H), 0.93 (d, J = 6.4 Hz, 3H). MS (ESI) m/e [M + 1]⁺ 378. | 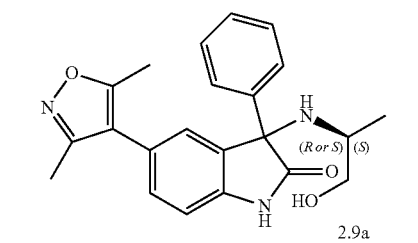<br>2.9a<br>Fast isomer in HPLC<br>Eluting reagent:<br>CH₃CN/H₂O/CF₃COOH = 25/100/0.1 |

| # | Name | ¹H NMR data LC/MS m/z (M + 1) | Structure |
|---|------|-------------------------------|-----------|
| 2.9b | 5-(3,5-dimethylisoxazol-4-yl)-3-((S)-1-hydroxypropan-2-ylamino)-3-phenylindolin-2-one | (DMSO-d₆) δ$_H$ 10.66 (s, 1H), 7.43-7.46 (m, 2H), 7.22-7.33 (m, 5H), 6.98 (d, J = 8.0 Hz, 1H) 4.46 (t, J = 5.6 Hz, 1H), 3.25-3.30 (m, 1H), 3.12-3.18 (m, 1H), 2.90 (d, J = 4.4 Hz, 1H), 2.35 (s, 3H), 2.18 (s, 3H), 0.73 (d, J = 6.0 Hz, 3H). MS (ESI) m/e [M + 1]⁺ 378. | 2.9b<br>(S or R) (S)<br>Slow isomer in HPLC<br>Eluting reagent:<br>CH₃CN/H₂O/CF₃COOH = 25/100/0.1 |
| 2.10a | 5-(3,5-dimethylisoxazol-4-yl)-3-((R)-1-hydroxypropan-2-ylamino)-3-phenylindolin-2-one | (DMSO-d₆) δ$_H$ 10.64 (s, 1H), 7.44-7.47 (m, 2H), 7.22-7.32 (m, 4H), 7.19 (s, 1H), 6.98 (d, J = 8.4 Hz, 1H), 4.41 (t, J = 5.6 Hz, 1H), 3.16-3.21 (m, 1H), 3.04-3.09 (m, 1H), 2.65 (d, J = 4.2 Hz, 1H), 2.42-2.47 (m, 1H), 2.36 (s, 3H), 2.18 (s, 3H), 0.92 (d, J = 6.4 Hz, 3H). MS (ESI) m/e [M + 1]⁺ 378. | 2.10a<br>(R or S) (R)<br>Fast isomer in HPLC<br>Eluting reagent:<br>CH₃CN/H₂O/CF₃COOH = 25/100/0.1 |
| 2.10b | 5-(3,5-dimethylisoxazol-4-yl)-3-((R)-1-hydroxypropan-2-ylamino)-3-phenylindolin-2-one | (DMSO-d₆) δ$_H$ 10.66 (s, 1H), 7.43-7.46 (m, 2H), 7.22-7.33 (m, 5H), 6.98 (d, J = 8.0 Hz, 1H), 4.46 (t, J = 5.6 Hz, 1H), 3.25-3.30 (m, 2H), 3.12-3.18 (m, 1H), 2.90 (d, J = 4.8 Hz, 1H), 2.35 (s, 3H), 2.18 (s, 3H), 0.73 (d, J = 6.4 Hz, 3H). MS (ESI) m/e [M + 1]⁺ 378. | 2.10b<br>(S or R) (R)<br>Slow isomer in HPLC<br>Eluting reagent:<br>CH₃CN/H₂O/CF₃COOH = 25/100/0.1 |
| 2.11a | 5-(3,5-dimethylisoxazol-4-yl)-3-((R)-1-hydroxy-3-methylbutan-2-ylamino)-3-phenylindolin-2-one | (DMSO-d₆) δ$_H$ 10.56 (s, 1H), 7.46-7.49 (m, 2H), 7.25-7.33 (m, 5H), 7.11 (s, 1H), 6.98 (d, J = 8.4 Hz, 1H), 4.25 (t, J = 5.6 Hz, 1H), 3.09-3.16 (m, 2H), 2.56 (d, J = 5.6 Hz, 1H), 2.38 (s, 3H), 2.24-2.30 (m, 1H), 2.20 (s, 3H), 1.79-1.84 (m, 1H), 0.89 (d, J = 7.2 Hz, 3H), 0.80 (d, J = 7.2 Hz, 3H). MS (ESI) m/e [M + 1]⁺ 406. | 2.11a<br>(R or S) (R)<br>Fast isomer in normal chromatography<br>Eluting reagent: DCM/MeOH = 100/1~20/1 |

| # | Name | ¹H NMR data LC/MS m/z (M + 1) | Structure |
|---|---|---|---|
| 2.11b | 5-(3,5-dimethylisoxazol-4-yl)-3-((R)-1-hydroxy-3-methylbutan-2-ylamino)-3-phenylindolin-2-one | (DMSO-d$_6$) δ$_H$ 10.75 (s, 1H), 7.47-7.50 (m, 2H), 7.19-7.34 (m, 4H), 7.11 (s, 1H), 6.99 (d, J = 8.4 Hz, 1H), 4.27 (t, J = 5.6 Hz, 1H), 3.37-3.43 (m, 1H), 2.29-3.35 (m, 1H), 2.66 (d, J = 7.6 Hz, 1H), 2.32 (s, 3H), 1.66-1.72 (m, 1H), 0.80 (d, J = 7.2 Hz, 6H). MS (ESI) m/e [M + 1]$^+$ 406. | 2.11b<br>Slow isomer in normal chromatography<br>Eluting reagent: DCM/MeOH = 100/1~20/1 |
| 2.12a | 5-(3,5-dimethylisoxazol-4-yl)-3-((S)-1-hydroxy-3-methylbutan-2-ylamino)-3-phenylindolin-2-one | (DMSO-d$_6$) δ$_H$ 10.57 (s, 1H), 7.46-7.49 (m, 2H), 7.23-7.34 (m, 5H), 6.97 (d, J = 8.8 Hz, 1H), 4.25 (t, J = 5.6 Hz, 1H), 3.09-3.17 (m, 2H), 2.56 (d, J = 5.6 Hz, 1H), 2.38 (s, 3H), 2.25-2.29 (m, 1H), 2.20 (s, 3H), 1.77-1.86 (m, 1H), 0.89 (d, J = 6.8 Hz, 3H), 0.81 (d, J = 7.2 Hz, 3H). MS (ESI) m/e [M + 1]$^+$ 406. | 2.12a<br>Fast isomer in normal chromatography<br>Eluting reagent: DCM/MeOH = 100/1~20/1 |
| 2.12b | 5-(3,5-dimethylisoxazol-4-yl)-3-((S)-1-hydroxy-3-methylbutan-2-ylamino)-3-phenylindolin-2-one | (DMSO-d$_6$) δ$_H$ 10.75 (s, 1H), 7.47-7.50 (m, 2H), 7.19-7.34 (m, 4H), 7.11 (s, 1H), 6.98 (d, J = 8.0 Hz, 1H), 4.27 (t, J = 5.6 Hz, 1H), 3.37-3.43 (m, 1H), 2.29-3.35 (m, 1H), 2.66 (d, J = 7.6 Hz, 1H), 2.31 (s, 3H), 2.15-2.20 (m, 1H), 2.14 (s, 3H), 1.65-1.73 (m, 1H), 0.80 (d, J = 6.8 Hz, 6H). MS (ESI) m/e [M + 1]$^+$ 406. | 2.12b<br>Slow isomer in normal chromatography<br>Eluting reagent: DCM/MeOH = 100/1~20/1 |
| 2.13a | 5-(3,5-dimethylisoxazol-4-yl)-3-((R)-2-hydroxypropylamino)-3-phenylindolin-2-one | (DMSO-d$_6$) δ$_H$ 10.64 (s, 1H), 7.44-7.46 (m, 2H), 7.23-7.34 (m, 4H), 7.20 (s, 1H), 6.98 (d, J = 8.0 Hz, 1H), 4.48 (d, J = 4.4 Hz, 1H), 3.62-3.66 (m, 1H), 2.89 (t, J = 7.6 Hz, 1H), 2.35 (s, 3H), 2.28-2.33 (m, 1H), 2.18 (s, 3H), 2.10-2.16 (m, 1H), 1.06 (d, J = 5.6 Hz, 3H). MS (ESI) m/e [M + 1]$^+$ 378. | 2.13a<br>Fast isomer in HPLC<br>Eluting reagent:<br>CH$_3$CN/H$_2$O/CF$_3$COOH = 25/100/0.1 |
| 2.13b | 5-(3,5-dimethylisoxazol-4-yl)-3-((R)-2-hydroxypropylamino)-3-phenylindolin-2-one | (DMSO-d$_6$) δ$_H$ 10.69 (s, 1H), 7.44-7.47 (m, 2H), 7.22-7.34 (m, 4H), 7.16 (s, 1H), 6.98 (d, J = 8.0 Hz, 1H), 4.55 (d, J = 4.8 Hz, 1H), 3.62-3.66 (m, 1H), 2.95 (dd, J = 4.8 Hz, 5.2 Hz, 1H), 2.34 (s, 3H), 2.25-2.31 (m, 1H), 2.16 (s, 3H), 2.05-2.08 (m, 1H), 1.00 (d, J = 6.4 Hz, 3H). MS (ESI) m/e [M + 1]$^+$ 378. | 2.13b<br>Slow isomer in HPLC<br>Eluting reagent:<br>CH$_3$CN/H$_2$O/CF$_3$COOH = 25/100/0.1 |

| # | Name | ¹H NMR data LC/MS m/z (M + 1) | Structure |
|---|------|-------------------------------|-----------|
| 2.14a | 5-(3,5-dimethylisoxazol-4-yl)-3-((S)-2-hydroxypropylamino)-3-phenylindolin-2-one | (DMSO-d$_6$) δ$_H$ 10.64 (s, 1H), 7.45-7.47 (m, 2H), 7.25-7.44 (m, 4H), 7.20 (s, 1H), 6.98 (d, J = 8.0 Hz, 1H), 4.48 (d, J = 4.4 Hz, 1H), 3.60-3.66 (m, 1H), 2.89 (t, J = 7.6 Hz, 1H), 2.35 (s, 3H), 2.28-2.33 (m, 1H), 2.18 (s, 3H), 2.11-2.15 (m, 1H), 1.02 (d, J = 6.4 Hz, 3H). MS (ESI) m/e [M + 1]⁺ 378. | 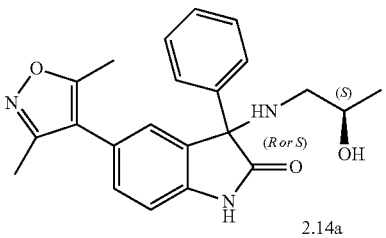 2.14a<br>Fast isomer in HPLC<br>Eluting reagent:<br>CH$_3$CN/H$_2$O/CF$_3$COOH = 25/100/0.1 |
| 2.14b | 5-(3,5-dimethylisoxazol-4-yl)-3-((S)-2-hydroxypropylamino)-3-phenylindolin-2-one | (DMSO-d$_6$) δ$_H$ 10.68 (s, 1H), 7.44-7.47 (m, 2H), 7.22-7.34 (m, 4H), 7.16 (s, 1H), 6.98 (d, J = 8.4 Hz, 1H), 4.54 (d, J = 4.8 Hz, 1H), 3.61-3.67 (m, 1H), 2.95 (dd, J = 4.0 Hz, 5.2 Hz, 1H), 2.34 (s, 3H), 2.24-2.32 (m, 1H), 2.16 (s, 3H), 2.03-2.09 (m, 1H), 0.99 (d, J = 6.4 Hz, 3H). MS (ESI) m/e [M + 1]⁺ 378. | 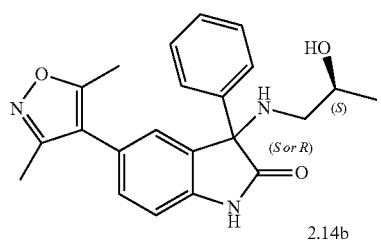 2.14b<br>Slow isomer in HPLC<br>Eluting reagent:<br>CH$_3$CN/H$_2$O/CF$_3$COOH = 25/100/0.1 |
| 2.15 | 5-(3,5-dimethylisoxazol-4-yl)-3-(3-hydroxypiperidin-1-yl)-3-phenylindolin-2-one | (DMSO-d$_6$) δ$_H$ 10.66-10.67 (m, 1H), 7.48-7.50 (m, 2H), 7.21-7.36 (m, 5H), 6.96 (d, J = 8.0 Hz, 1H), 4.55-4.57 (m, 1H), 3.34-3.49 (m, 1H), 2.76-2.79 (m, 1H), 2.54-2.59 (m, 1H), 2.36-2.37 (m, 3H), 2.19-2.22 (m, 3H), 1.78-2.13 (m, 3H), 1.55-1.58 (m, 1H), 1.39-1.42 (m, 1H), 1.02-1.05 (m, 1H). MS (ESI) m/e [M + 1]⁺ 404. | 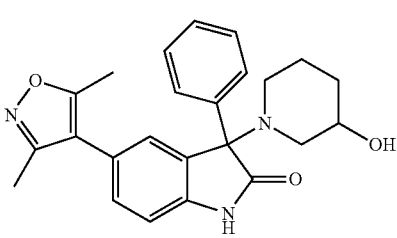 [SMILES: Cc1noc(C)c1-c1ccc2c(c1)C(c1ccccc1)(N1CCCC(O)C1)C(=O)N2] |
| 2.16 | 5-(3,5-dimethylisoxazol-4-yl)-3-((S)-3-hydroxypiperidin-1-yl)-3-phenylindolin-2-one | (DMSO-d$_6$) δ$_H$ 10.68 (m, 1H), 7.48-7.50 (m, 2H), 7.22-7.36 (m, 5H), 6.96 (d, J = 8.0 Hz, 1H), 4.55-4.58 (m, 1H), 3.32-3.46 (m, 1H), 2.76-2.79 (m, 1H), 2.57-2.60 (m, 1H), 2.36-2.37 (m, 3H), 2.19-2.20 (m, 3H), 1.78-2.13 (m, 3H), 1.55-1.57 (m, 1H), 1.36-1.42 (m, 1H), 1.02-1.05 (m, 1H). MS (ESI) m/e [M + 1]⁺ 404. | 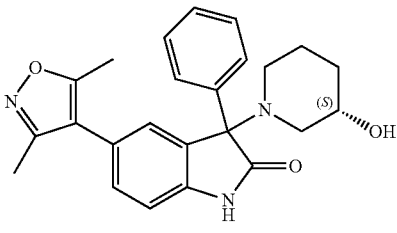 |
| 2.17 | 5-(3,5-dimethylisoxazol-4-yl)-3-((R)-3-hydroxypiperidin-1-yl)-3-phenylindolin-2-one | (DMSO-d$_6$) δ$_H$ 10.68 (m, 1H), 7.49-7.51 (m, 2H), 7.21-7.37 (m, 5H), 6.95-6.97 (d, J = 8.0 Hz, 1H), 4.55-4.58 (m, 1H), 3.40-3.52 (m, 1H), 2.74-2.82 (m, 1H), 2.55-2.63 (m, 1H), 2.37-2.38 (m, 3H), 2.19-2.20 (m, 3H), 1.91-2.17 (m, 2H), 1.76-1.84 (m, 1H), 1.52-1.62 (m, 1H), 1.35-1.46 (m, 1H), 0.99-1.10 (m, 1H). MS (ESI) m/e [M + 1]⁺ 404. | 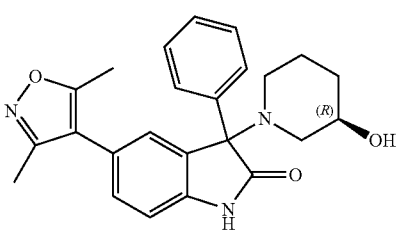 |

| # | Name | ¹H NMR data LC/MS m/z (M + 1) | Structure |
|---|---|---|---|
| 2.17a | 5-(3,5-dimethylisoxazol-4-yl)-3-((R)-3-hydroxypiperidin-1-yl)-3-phenylindolin-2-one | (DMSO-d$_6$) δ$_H$ 10.68 (s, 1H), 7.50 (d, J = 7.6 Hz, 2H), 7.21-7.37 (m, 5H), 6.96 (d, J = 7.6 Hz, 1H), 4.57 (d, J = 5.6 Hz, 1H), 3.40-3.50 (m, 1H), 2.75-2.81 (m, 1H), 2.55-2.60 (m, 1H), 2.37 (s, 3H), 2.20 (s, 3H), 2.16-2.20 (m, 1H), 1.91-1.97 (m, 1H), 1.76-1.84 (m, 1H), 1.52-1.62 (m, 1H), 1.35-1.46 (m, 1H), 0.99-1.10 (m, 1H). MS (ESI) m/e [M + 1]$^+$ 404. | 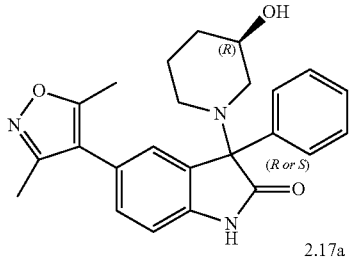<br>2.17a<br>Fast isomer in normal chromatography<br>Eluting reagent: DCM/MeOH = 40/1 |
| 2.17b | 5-(3,5-dimethylisoxazol-4-yl)-3-((R)-3-hydroxypiperidin-1-yl)-3-phenylindolin-2-one | (DMSO-d$_6$) δ$_H$ 10.68 (s, 1H), 7.50 (d, J = 7.6 Hz, 2H), 7.23-7.37 (m, 5H), 6.96 (d, J = 8.0 Hz, 1H), 4.56 (d, J = 4.8 Hz, 1H), 3.43-3.52 (m, 1H), 2.74-2.80 (m, 1H), 2.57-2.62 (m, 1H), 2.36 (s, 3H), 2.19 (s, 3H), 2.00-2.14 (m, 1H), 1.76-1.83 (m, 1H), 1.53-1.61 (m, 1H), 1.33-1.42 (m, 1H), 1.00-1.10 (m, 1H). MS (ESI) m/e [M + 1]$^+$ 404. | 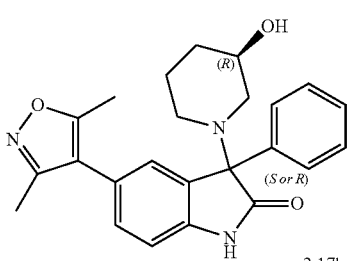<br>2.17b<br>Slow isomer in normal chromatography<br>Eluting reagent: DCM/MeOH = 40/1 |
| 2.18 | 3-cyclohexyl-5-(3,5-dimethylisoxazol-4-yl)-3-(2-hydroxyethylamino)indolin-2-one | (DMSO-d$_6$) δ$_H$ 10.49 (s, 1H), 7.26 (d, J = 8.0 Hz, 1H), 7.19 (s, 1H), 6.95 (d, J = 8.0 Hz, 1H), 4.47 (t, J = 5.6 Hz, 1H), 3.34-3.38 (m, 2H), 2.39 (s, 3H), 2.31-2.33 (m, 1H), 2.27 (s, 3H), 1.97-2.06 (m, 2H), 1.34-1.57 (m, 5H), 0.73-1.15 (m, 6H). MS (ESI) m/e [M + 1]$^+$ 370. | 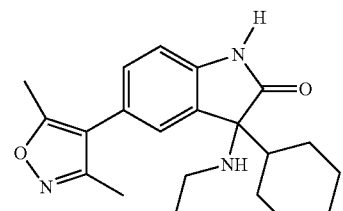 |
| 2.19a | 3-cyclohexyl-5-(3,5-dimethylisoxazol-4-yl)-3-((S)-1-hydroxy-3-methylbutan-2-ylamino)indolin-2-one | (DMSO-d$_6$) δ$_H$ 10.39 (s, 1H), 7.19 (d, J = 8.0 Hz,. 1H), 7.18 (s, 1H), 6.88 (d, J = 8.0 Hz, 1H), 4.07 (t, J = 5.6 Hz, 1H), 3.00-3.03 (m, 2H), 2.40 (s, 3H), 2.22 (s, 3H), 2.06 (s, 2H), 1.87 (d, J = 11.6 Hz, 1H), 1.55-1.72 (m, 6H), 0.91-1.16 (m, 4H), 0.81 (d, J = 6.8 Hz, 3H), 0.6-0.74 (m, 4H). MS (ESI) m/e [M + 1]$^+$ 412. | 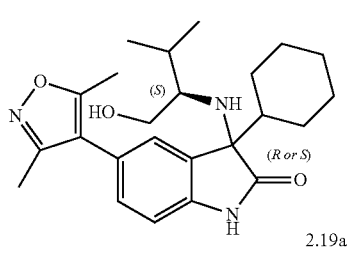<br>2.19a<br>Fast isomer in normal chromatography<br>Eluting reagent: DCM/MeOH = 50/1 |
| 2.19b | 3-cyclohexyl-5-(3,5-dimethylisoxazol-4-yl)-3-((S)-1-hydroxy-3-methylbutan-2-ylamino)indolin-2-one | (DMSO-d$_6$) δ$_H$ 10.47 (s, 1H), 7.20 (d, J = 8.0 Hz, 1H), 7.11 (s, 1H), 6.91 (d, J = 8.0 Hz, 1H), 4.15 (t, J = 5.2 Hz, 1H), 3.27-3.31 (m, 1H), 3.14-3.20 (m, 1H), 2.37 (s, 3H), 2.19 (s, 3H), 2.05-2.13 (m, 2H), 1.92 (s, 1H), 1.42-1.73 (m, 6H), 0.87-1.18 (m, 4H), 0.71 (t, J = 7.6 Hz, 6H), 0.50-0.61 (m, 1H). MS (ESI) m/e [M + 1]$^+$ 412. | 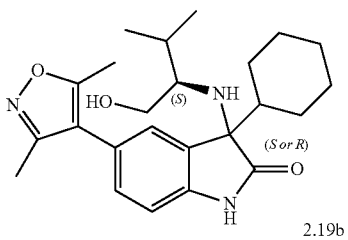<br>2.19b<br>Slow isomer in normal chromatography<br>Eluting reagent: DCM/MeOH = 50/1 |

| # | Name | ¹H NMR data LC/MS m/z (M + 1) | Structure |
|---|---|---|---|
| 2.20a | 3-cyclohexyl-5-(3,5-dimethylisoxazol-4-yl)-3-((R)-1-hydroxy-3-methylbutan-2-ylamino)indolin-2-one | (DMSO-d₆) δ_H 10.39 (s, 1H), 7.19 (d, J = 8.0 Hz, 1H), 7.18 (s, 1H), 6.88 (d, J = 8.0 Hz, 1H), 4.07 (t, J = 4.8 Hz, 1H), 3.01 (s, 2H), 2.40 (s, 3H), 2.22 (s, 3H), 2.07 (s, 2H), 1.87 (d, J = 12 Hz, 1H), 1.55-1.74 (m, 6H), 0.88-1.16 (m, 4H), 0.81 (d, J = 6.8 Hz, 3H), 0.70-0.74 (m, 4H). MS (ESI) m/e [M + 1]⁺ 412. | 2.20a Fast isomer in normal chromatography Eluting reagent: DCM/MeOH = 50/1 |
| 2.20b | 3-cyclohexyl-5-(3,5-dimethylisoxazol-4-yl)-3-((R)-1-hydroxy-3-methylbutan-2-ylamino)indolin-2-one | (DMSO-d₆) δ_H 10.47 (s, 1H), 7.20 (d, J = 8.0 Hz, 1H), 7.11 (s, 1H), 6.90 (d, J = 8.0 Hz, 1H), 4.14 (t, J = 5.2 Hz, 1H), 3.27-3.31 (m, 1H), 3.15-3.20 (m, 1H), 2.37 (s, 3H), 2.19 (s, 3H), 2.05-2.10 (m, 2H), 1.93 (s, 1H), 1.42-1.73 (m, 6H), 0.87-1.18 (m, 4H), 0.71 (t, J = 7.6 Hz, 6H), 0.51-0.61 (m, 1H). MS (ESI) m/e [M + 1]⁺ 412. | 2.20b Slow isomer in normal chromatography Eluting reagent: DCM/MeOH = 50/1 |
| 2.21 | 3-cyclohexyl-5-(3,5-dimethylisoxazol-4-yl)-3-((S)-2-hydroxypropylamino)indolin-2-one | (DMSO-d₆) δ_H 10.40-10.62 (m, 1H), 7.11-7.21 (m, 2H), 6.87-6.90 (m, 1H), 4.30-4.27 (m, 1H), 3.51-3.52 (m, 1H), 2.36-2.38 (m, 3H), 2.09-2.20 (m, 4H), 1.54-1.89 (m, 6H), 0.90-1.01 (m, 6H), 0.65-0.71 (m, 1H). MS (ESI) m/e [M + 1]⁺ 384. | 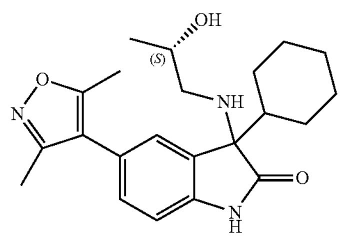 |
| 2.22 | 3-cyclohexyl-5-(3,5-dimethylisoxazol-4-yl)-3-((R)-2-hydroxypropylamino)indolin-2-one | (DMSO-d₆) δ_H 10.40-10.42 (m, 1H), 7.11-7.21 (m, 2H), 6.88-6.90 (m, 1H), 4.30-4.47 (m, 1H), 3.51-3.52 (m, 1H), 2.36-2.38 (m, 3H), 2.11-2.20 (m, 4H), 1.58-1.89 (m, 6H), 0.90-1.09 (m, 6H), 0.66-0.72 (m, 1H). MS (ESI) m/e [M + 1]⁺ 384. | 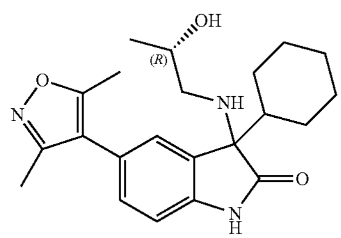 |
| 2.23 | 3-cyclohexyl-5-(3,5-dimethylisoxazol-4-yl)-3-((S)-1-hydroxypropan-2-ylamino)indolin-2-one | (DMSO-d₆) δ_H 10.41-10.43 (m, 1H), 7.12-7.21 (m, 2H), 6.88-6.91 (m, 1H), 4.22-4.423 (m, 1H), 2.91-3.10 (m, 2H), 2.16-2.38 (m, 8H), 1.91-1.94 (m, 1H), 1.50-1.61 (m, 5H), 0.84-1.11 (m, 6H), 0.58-0.65 (m, 3H). MS (ESI) m/e [M + 1]⁺ 384. | 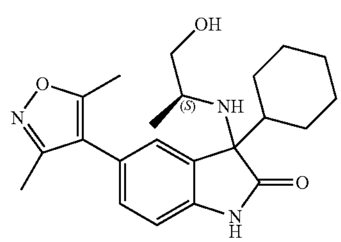 |
| 2.24 | 3-cyclohexyl-5-(3,5-dimethylisoxazol-4-yl)-3-((R)-1-hydroxypropan-2-ylamino)indolin-2-one | (DMSO-d₆) δ_H 10.42-10.43 (m, 1H), 7.13-7.21 (m, 2H), 6.88-6.91 (m, 1H), 4.22-4.43 (m, 1H), 2.93-3.17 (m, 2H), 2.16-2.37 (m, 8H), 1.91-1.94 (m, 1H), 1.51-1.62 (m, 5H), 0.84-1.11 (m, 6H), 0.58-0.65 (m, 3H). MS (ESI) m/e [M + 1]⁺ 384. | 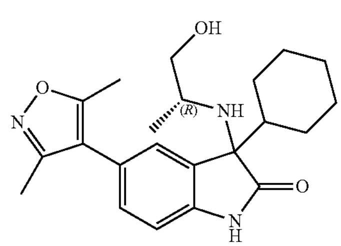 |

| # | Name | ¹H NMR data LC/MS m/z (M + 1) | Structure |
|---|------|-------------------------------|-----------|
| 2.25 | 3-cyclohexyl-5-(3,5-dimethylisoxazol-4-yl)-3-(isopentylamino)indolin-2-one | (DMSO-d₆) δ_H 10.40 (s, 1H), 7.19 (d, J = 8.0 Hz, 1H), 7.12 (s, 1H), 6.89 (d, J = 8.0 Hz, 1H), 2.38 (s, 3H), 2.20 (s, 3H), 1.99-2.21 (m, 3H), 1.49-1.56 (m, 6H), 0.96-1.16 (m, 6H), 0.68-0.74 (m, 7H). MS (ESI) m/e [M + 1]⁺ 396. | 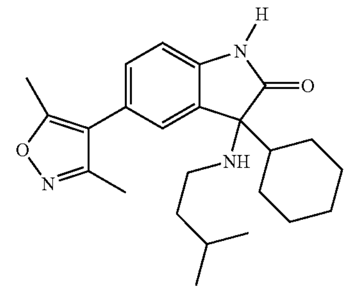 [SMILES: Cc1noc(C)c1-c1ccc2c(c1)C(NCCC(C)C)(C1CCCCC1)C(=O)N2] |
| 2.26 | 3-cyclohexyl-5-(3,5-dimethylisoxazol-4-yl)-3-(4-methylpieprazin-1-yl)indolin-2-one | (DMSO-d₆) δ_H 10.44 (s, 1H), 7.21 (d, J = 8.0 Hz, 1H), 7.11 (s, 1H), 6.88 (d, J = 8.0 Hz, 1H), 2.50-2.52 (m, 4H), 2.39 (s, 3H), 2.26-2.28 (m, 4H), 2.21 (s, 3H), 2.11 (s, 3H), 2.03-2.06 (m, 1H), 1.57-1.82 (m, 4H), 1.10-1.43 (m, 6H). MS (ESI) m/e [M + 1]⁺ 396. | 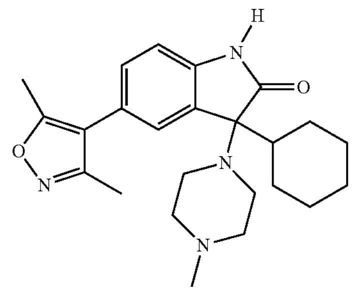 [SMILES: Cc1noc(C)c1-c1ccc2c(c1)C(C1CCCCC1)(N1CCN(C)CC1)C(=O)N2] |
| 2.27 | 3-cyclohexyl-5-(3,5-dimethylisoxazol-4-yl)-3-(isopropylamino)indolin-2-one | (DMSO-d₆) δ_H 10.42 (s, 1H), 7.19 (d, J = 8.0 Hz, 1H), 7.13 (s, 1H), 6.89 (d, J = 8.0 Hz, 1H), 2.41-2.42 (m, 1H), 2.38 (s, 3H), 2.20 (s, 3H), 1.92-2.04 (m, 2H), 1.48-1.68 (m, 5H), 0.92-1.13 (m, 4H), 0.86 (d, J = 6.0 Hz, 3H), 0.69 (d, J = 6.0 Hz, 1H). MS (ESI) m/e [M + 1]⁺ 368. | 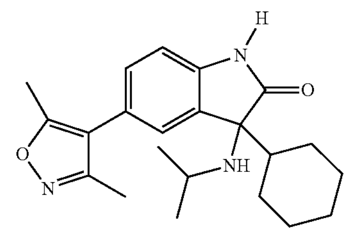 [SMILES: Cc1noc(C)c1-c1ccc2c(c1)C(NC(C)C)(C1CCCCC1)C(=O)N2] |
| 2.28 | 3-cyclohexyl-3-(2-(dimethylamino)ethylamino)-5-(3,5-dimethylisoxazol-4-yl)indolin-2-one | (DMSO-d₆) δ_H 10.50 (s, 1H), 7.21 (d, J = 8.0 Hz, 1H), 7.15 (s, 1H), 6.91 (d, J = 8.0 Hz, 1H), 2.50-2.57 (m, 1H), 2.42-2.45 (m, 1H), 2.38 (s, 3H), 2.25-2.30 (m, 8H), 2.21 (s, 3H), 2.08-2.13 (m, 1H), 1.92-1.95 (m, 1H), 1.50-1.69 (m, 5H), 0.92-1.13 (m, 4H), 0.65-0.74 (m, 1H). MS (ESI) m/e [M + 1]⁺ 397. | 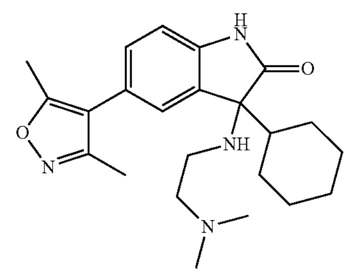 [SMILES: Cc1noc(C)c1-c1ccc2c(c1)C(NCCN(C)C)(C1CCCCC1)C(=O)N2] |
| 2.29 | 3-cyclohexyl-3-(2-(dimethylamino)ethylamino)-5-(3,5-dimethylisoxazol-4-yl)indolin-2-one | (DMSO-d₆) δ_H 10.50 (s, 1H), 7.23 (m, d, J = 8.0 Hz, 1H), 7.14 (s, 1H), 6.88 (d, J = 8.0 Hz, 1H), 3.50 (brs, 4H), 2.50-2.51 (m, 4H), 2.39 (s, 3H), 2.21 (s, 3H), 2.03-2.07 (m, 1H), 1.40-1.82 (m, 5H), 1.14-1.22 (m, 3H), 0.93-0.96 (m, 1H), 0.63-0.66 (m, 1H). MS (ESI) m/e [M + 1]⁺ 396. | 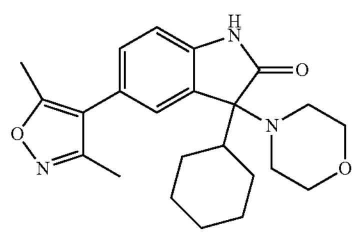 [SMILES: Cc1noc(C)c1-c1ccc2c(c1)C(C1CCCCC1)(N1CCOCC1)C(=O)N2] |
| 2.30 | 3-cyclohexyl-5-(3,5-dimethylisoxazol-4-yl)-3-((R)-3-hydroxypiperidin-1-yl)indolin-2-one | (DMSO-d₆) δ_H 10.41-10.42 (m, 1H), 7.22 (d, J = 8.0 Hz, 1H), 7.12 (s, 1H), 6.88 (d, J = 8.0 Hz, 1H), 4.56-4.57 (m, 1H), 3.31-3.40 (m, 1H), 2.58-2.98 (m, 1H), 2.40-2.41 (m, 3H), 2.22-2.23 (m, 3H), 0.84-2.17 (m, 17H), 0.57-0.74 (m, 1H). MS (ESI) m/e [M + 1]⁺ 410. | 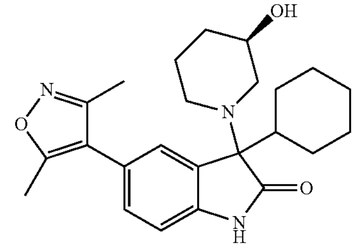 [SMILES: Cc1noc(C)c1-c1ccc2c(c1)C(C1CCCCC1)(N1CCC[C@@H](O)C1)C(=O)N2] |

| # | Name | ¹H NMR data LC/MS m/z (M + 1) | Structure |
|---|---|---|---|
| 2.31 | 3-cyclohexyl-5-(3,5-dimethylisoxazol-4-yl)-3-(4-hydroxypiperidin-1-yl)indolin-2-one | (DMSO-d$_6$) $\delta_H$ 10.39 (m, 1H), 7.20 (d, J = 8.0 Hz, 1H), 7.12 (s, 1H), 6.87 (d, J = 8.0 Hz, 1H), 4.48 (d, J = 3.6 Hz, 1H), 3.37 (s, 1H), 2.83 (s, 1H), 2.40 (s, 3H), 1.58-1.78 (m, 6H), 1.15-1.44 (m, 5H), 0.92-0.98 (m, 4H), 0.63-0.72 (m, 1H). MS (ESI) m/e [M + 1]$^+$ 410. | 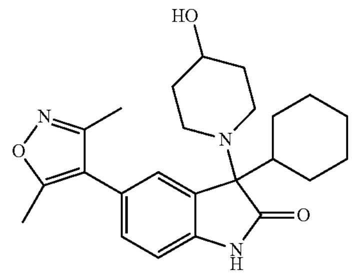 [SMILES: Cc1noc(C)c1-c1ccc2c(c1)C(C1CCCCC1)(N1CCC(O)CC1)C(=O)N2] |
| 2.32 | 3-cyclohexyl-5-(3,5-dimethylisoxazol-4-yl)-3-(3-hydroxypiperidin-1-yl)indolin-2-one | (DMSO-d$_6$) $\delta_H$ 10.40-10.41 (m, 1H), 7.22 (d, J = 8.0 Hz, 1H), 7.12 (s, 1H), 6.88 (d, J = 8.0 Hz, 1H), 4.54-4.56 (m, 1H), 3.27-3.38 (m, 1H), 2.58-2.98 (m, 1H), 2.40-2.41 (m, 3H), 2.22-2.24 (m, 3H), 0.97-2.17 (m, 17H), 0.58-0.73 (m, 1H). MS (ESI) m/e [M + 1]$^+$ 410. | 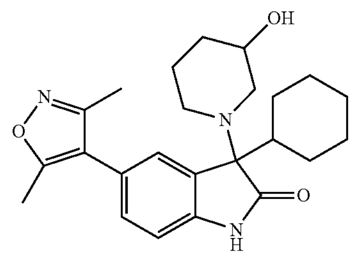 [SMILES: Cc1noc(C)c1-c1ccc2c(c1)C(C1CCCCC1)(N1CCCC(O)C1)C(=O)N2] |
| 2.33 | 3-cyclohexyl-5-(3,5-dimethylisoxazol-4-yl)-3-(3-hydroxyazetidin-1-yl)indolin-2-one | (DMSO-d$_6$) $\delta_H$ 10.46 (s, 1H), 7.20 (d, J = 8.0 Hz, 1H), 7.12 (s, 1H), 6.89 (d, J = 8.0 Hz, 1H), 4.11-4.18 (m, 1H), 3.64-3.65 (m, 1H), 3.31-3.32 (m, 1H), 3.19-3.21 (m, 1H), 2.64-2.65 (m, 1H), 2.39 (s, 1H), 2.21 (s, 3H), 1.56-1.98 (m, 5H), 1.14-1.38 (m, 5H), 0.50-0.59 (m, 1H). MS (ESI) m/e [M + 1]$^+$ 382. | 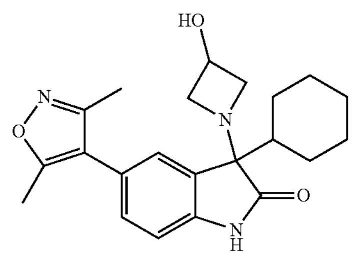 [SMILES: Cc1noc(C)c1-c1ccc2c(c1)C(C1CCCCC1)(N1CC(O)C1)C(=O)N2] |
| 2.34 | 3-cyclopentyl-5-(3,5-dimethylisoxazol-4-yl)-3-morpholinoindolin-2-one | (DMSO-d$_6$) $\delta_H$ 10.47 (s, 1H), 7.19-7.23 (m, 2H), 6.90 (d, J = 8.0 Hz, 1H), 3.50-3.51 (m, 4H), 2.61-2.65 (m, 4H), 2.37 (s, 3H), 2.20 (s, 3H), 1.62-1.68 (m, 2H), 1.24-1.47 (m, 7H). MS (ESI) m/e [M + 1]$^+$ 382. | 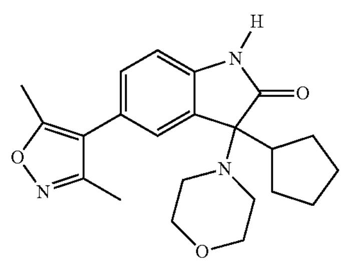 [SMILES: Cc1noc(C)c1-c1ccc2c(c1)C(C1CCCC1)(N1CCOCC1)C(=O)N2] |
| 2.35 | 3-cyclopentyl-5-(3,5-dimethylisoxazol-4-yl)-3-(2-hydroxyethylamino)indolin-2-one | (DMSO-d$_6$) $\delta_H$ 10.44 (s, 1H), 7.20-7.21 (m, 2H), 6.90 (d, J = 8.0 Hz, 1H), 4.41 (t, J = 5.6 Hz, 1H), 3.16-3.30 (m, 2H), 2.38 (s, 3H), 2.24-2.31 (m, 2H), 2.20 (s, 3H), 1.99-2.04 (m, 1H), 1.33-1.62 (m, 7H), 1.11-1.14 (m, 1H). MS (ESI) m/e [M + 1]$^+$ 356. | 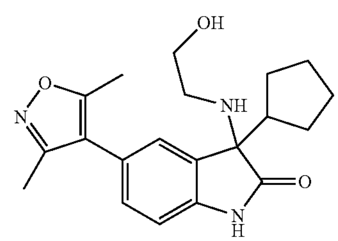 [SMILES: Cc1noc(C)c1-c1ccc2c(c1)C(NCCO)(C1CCCC1)C(=O)N2] |
| 2.36 | 3-cyclopentyl-5-(3,5-dimethylisoxazol-4-yl)-3-(4-methylpiperazin-1-yl)indolin-2-one | (DMSO-d$_6$) $\delta_H$ 10.53 (s, 1H), 7.23 (d, J = 8.0 Hz, 1H), 7.17 (s, 1H), 6.92 (d, J = 8.0 Hz, 1H), 3.16-3.30 (m, 2H), 2.59-2.67 (m, 7H), 2.36-2.38 (m, 5H), 2.20 (s, 3H), 2.20 (s, 3H), 1.99-2.04 (m, 1H), 1.33-1.62 (m, 7H), 1.11-1.14 (m, 1H). MS (ESI) m/e [M + 1]$^+$ 356. | 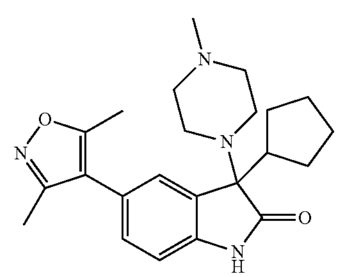 [SMILES: Cc1noc(C)c1-c1ccc2c(c1)C(C1CCCC1)(N1CCN(C)CC1)C(=O)N2] |

| # | Name | ¹H NMR data LC/MS m/z (M + 1) | Structure |
|---|---|---|---|
| 2.37 | 3-amino-3-cyclohexyl-5-(3,5-dimethylisoxazol-4-yl) indolin-2-one | (DMSO-d₆) δ$_H$ 10.29 (s, 1H), 7.17-7.18 (m, 2H), 7.12 (s, 1H), 6.88 (d, J = 8.0 Hz, 1H), 2.39 (s, 3H), 2.21 (s, 3H), 1.97-2.00 (m, 1H), 1.51-1.62 (m, 5H), 0.89-1.14 (m, 4H), 0.68-0.74 (m, 1H). MS (ESI) m/e [M + 1]⁺ 326 | 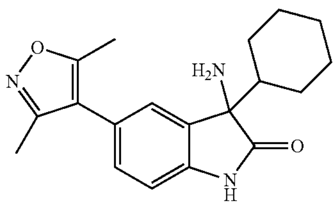 [SMILES: Cc1noc(C)c1-c1ccc2c(c1)C(N)(C1CCCCC1)C(=O)N2] |

Compound 2.37a

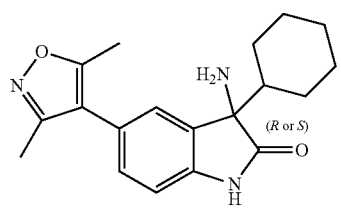

Fast isomer in chiral AD HPLC
Eluting reagent: Hexane/EtOH = 7/3

Step 1: (S,Z)—N-(5-(3,5-dimethylisoxazol-4-yl)-2-oxoindolin-3-ylidene)-2-methylpropane-2-sulfonamide

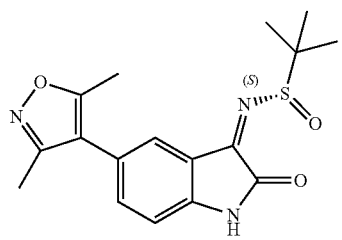

To a solution of 5-(3,5-dimethylisoxazol-4-yl)indoline-2,3-dione (2.42 g, 10 mmol) in THF (50 mL) was added (S)-2-methylpropane-2-sulfinamide (1.33 g, 11 mmol) and tetraethoxytitanium (9.12 g, 40 mmol). The mixture was heated at reflux for 15 h, and then cooled to RT, saturated NaHCO₃ (50 mL) was added, filtrated, washed with EtOAc (50 mL), and the filtrate was extracted with EtOAc (2×50 mL), dried with Na₂SO₄, filtrated, concerned in vacuum, the mixture was purified with chromatography on column to give red solid (2.6 g, 74%). ¹H NMR (400 MHz, DMSO-d₆): δ$_H$ 10.80 (s, 1H), 7.57 (d, J=8.0 Hz, 2H), 7.18-7.32 (m, 5H), 6.93 (d, J=8.0 Hz, 1H), 4.66-4.68 (m, 1H), 4.15-4.29 (m, 2H), 2.85-2.89 (m, 5H), 2.37 (s, 3H), 2.18 (s, 3H), 1.91-1.98 (m, 1H), 1.63-1.68 (m, 1H). MS (ESI) m/e [M+1]⁺ 346.

Step 2: (S,Z)-tert-butyl 3-(tert-butylsulfinylimino)-5-(3,5-dimethylisoxazol-4-yl)-2-oxoindoline-1-carboxylate Under a nitrogen atmosphere, a mixture of (S,Z)—N-(5-(3,5-dimethylisoxazol-4-yl)-2-oxoindolin-3-ylidene)-2-methylpropane-2-sulfonamide (0.50 g, 1.43 mmol), (Boc)₂O (0.38 g, 1.74 mmol), and DMAP (0.017 g, 0.14 mmol) in anhydrous THF (20 mL) was stirred from 0° C. to RT for 2.5 h. After cooling to 0° C., the reaction mixture was quenched by adding saturated NaHCO₃ (10 mL), and the mixture was extracted with CH₂Cl₂ (2×20 mL), combined the organic phase, dried, filtered, and the filtrate was concentrated in vacuo. The residue was used for the next step without further purified.

Step 3: (S-tert-butyl 3-cyclohexyl-3-(1,1-dimethylethlsulfinamido)-5-(3,5-dimethyl-isoxazol-4-yl)-2-oxoindoline-1-carboxylate

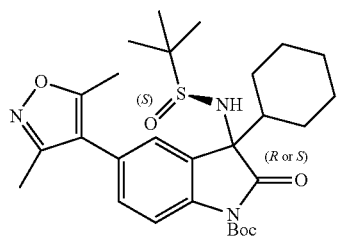

To a solution of (S,Z)-tert-butyl 3-(tert-butylsulfinylimino)-5-(3,5-dimethyl-isoxazol-4-yl)-2-oxoindoline-1-carboxylate (0.40 mmol) in 6 mL of dry THF under nitrogen atmosphere was added cyclohexylmagnesium chloride solution (0.9 mmol) at 0° C. The reaction mixture was stirred for 1 h at 0° C. and at room temperature for 12 h. The reaction was quenched with 10 mL of saturated aq. NH₄Cl solution, and the organic phase was extracted with CH₂Cl₂ (2×10 mL), dried over Na₂SO₄, and evaporated under reduced pressure. The crude addition product was purified by flash chromatography to give desired isomer as predominant product. MS (ESI) m/e [M+1-100]⁺ 430.

Step 4: 3-Amino-3-cyclohexyl-5-(3,5-dimethylisoxazol-4-yl)indolin-2-one

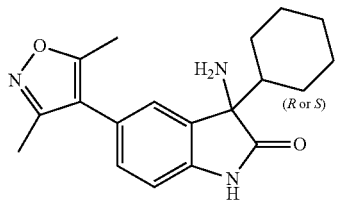

To a solution of (S)-tert-butyl 3-cyclohexyl-3-(1,1-dimethylethylsulfinamido)-5-(3,5-dimethyl-isoxazol-4-yl)-2-oxoindoline-1-carboxylate (53 mg, 0.1 mmol) in 2 mL of dioxane was added, a HCl saturated dioxane solution (1.0 mmol) at room temperature. The reaction mixture was stirred for 15 min. The reaction was quenched with 6 mL of aqueous NaHCO₃, and the organic phase was extracted with CH₂Cl₂, dried, and evaporated under reduced pressure to afford pure (S)-3-amino-3-cyclohexyl-5-(3,5-dimethylisoxazol-4-yl)indolin-2-one (21 mg, 65%) as a solid. ¹H NMR (400 MHz, DMSO-d₆): $\delta_H$ 10.32 (s, 1H), 7.17-7.19 (m, 2H), 6.88 (d, J=8.8 Hz, 1H), 2.39 (s, 3H), 2.21 (s, 3H), 1.90-1.93 (m, 1H), 1.53-1.63 (m, 5H), 0.95-1.11 (m, 4H), 0.68-0.72 (m, 1H). MS (ESI) m/e [M+1]⁺ 326. MS (ESI) m/e [M+1]⁺ 326.
Compound 2.37b

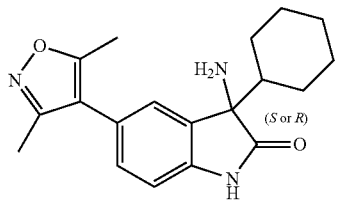 [SMILES: Cc1noc(C)c1-c1ccc2c(c1)C(N)(C1CCCCC1)C(=O)N2]

Slow isomer in chiral AD HPLC
Eluting reagent: Hexane/EtOH = 7/3

3-Amino-3-cyclohexyl-5-(3,5-dimethylisoxazol-4-yl)indolin-2-one

Compound 2.37b was synthesized using the same procedure of compound 2.37a. ¹H NMR (400 MHz, DMSO-d₆): $\delta_H$ 10.35 (s, 1H), 7.18-7.20 (m, 2H), 6.89 (d, J=8.4 Hz, 1H), 2.39 (s, 3H), 2.21 (s, 3H), 1.90-1.93 (m, 1H), 1.53-1.68 (m, 5H), 0.95-1.11 (m, 4H), 0.68-0.72 (m, 1H). MS (ESI) m/e [M+1]⁺ 326.

Compound 2.38

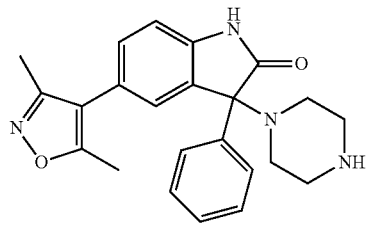 [SMILES: Cc1noc(C)c1-c1ccc2c(c1)C(c1ccccc1)(N1CCNCC1)C(=O)N2]

Step 1: tert-butyl 4-(5-(3,5-dimethylisoxazol-4-yl)-2-oxo-3-phenylindolin-3-yl)piperazine-1-carboxylate

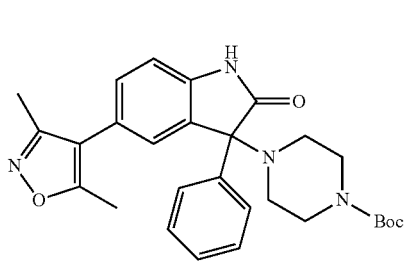 [SMILES: Cc1noc(C)c1-c1ccc2c(c1)C(c1ccccc1)(N1CCN(C(=O)OC(C)(C)C)CC1)C(=O)N2]

676 mg (2.0 mmol) of 3-chloro-5-(3,5-dimethylisoxazol-4-yl)-3-phenylindolin-2-one and 774 mg (6.0 mmol) of DIPEA were dissolved in 20 ml of THF, after the addition of 774 mg (4.0 mmol) of tert-butyl piperazine-1-carboxylate, the reaction solution was stirred for 0.5 h at room temperature. Subsequently, the solution was diluted with water. The aqueous phase was extracted with CH₂Cl₂ (2×30 mL). The combined organic phases were washed with aqueous NaHCO₃ and with water, dried and concentrated in vacuum. The resulting residue was purified by chromatography (eluent: CH₂Cl₂/MeOH=20/1) to give product (940 mg, 96%) as a white solid. ¹H NMR (400 MHz, DMSO-d₆): $\delta_H$ 10.75 (s, 1H), 7.51 (d, J=8.0 Hz, 1H), 7.25-7.38 (m, 6H), 6.98 (d, J=8.0 Hz, 1H), 3.27-3.29 (m, 4H), 2.47-2.38 (m, 4H), 2.36 (s, 3H), 2.18 (s, 3H), 1.35 (s, 9H). MS (ESI) m/e [M+1]⁺ 489.

Step 2: 5-(3,5-dimethylisoxazol-4-yl)-3-phenyl-3-(piperazin-1-yl)indolin-2-one

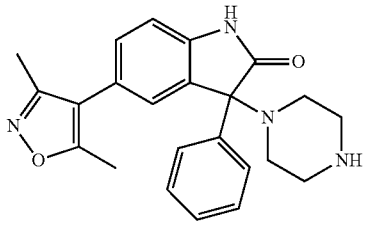 [SMILES: Cc1noc(C)c1-c1ccc2c(c1)C(c1ccccc1)(N1CCNCC1)C(=O)N2]

To a solution of tert-butyl 4-(5-(3,5-dimethylisoxazol-4-yl)-2-oxo-3-phenylindolin-3-yl)piperazine-1-carboxylate (0.9 g, 1.8 mmol) in CH₂Cl₂ (5 mL) was added TFA (5 mL) at 0° C., after adding up, the reaction was stirred at room temperature for 2.0 h. The solvent was evaporated in vacuo to give crude product. It was dissolved in water (20 mL), and was neutralized with NaHCO₃ to PH=7~8, and then the mixture was extracted with EtOAc (2×30 mL), combined organic phase, dried with $Na_2SO_4$, filtrated, concentrated to give crude product, and the mixture was purified by chromatography (eluent. $CH_2Cl_2$/MeOH/$NH_3H_2O$=20/1/0.05) to give product (500 mg, 71.6%) as a white solid. $^1$H NMR (400 MHz, DMSO-$d_6$): $\delta_H$ 10.75 (s, 1H), 7.49 (d, J=8.0 Hz, 2H), 7.23-7.36 (m, 5H), 6.97 (d, J=8.0 Hz, 1H), 2.65-2.66 (m, 4H), 2.31-2.47 (m, 7H), 2.19 (s, 3H). MS (ESI) m/e [M+1]$^+$ 389.

The following compounds, compound 2.39 through 2.46, were synthesized starting from the corresponding reagent to the similar procedures described as those of compound 2.38.

| # | Name | $^1$H NMR data LC/MS M/z (M + 1) | Structure |
|---|------|-----------------------------------|-----------|
| 2.39 | 5-(3,5-Dimethylisoxazol-4-yl)-3-phenyl-3-(piperazin-1-yl)indolin-2-one | (DMSO-$d_6$) $\delta_H$ 10.44 (s, 1H), 7.22 (d, J = 8.0 Hz, 1H), 7.12 (s, 1H), 6.88 (d, J = 8.0 Hz, 1H), 2.64-2.66 (m, 4H), 2.46-2.49 (m, 4H), 2.40 (s, 3H), 2.20 (s, 3H), 2.03-2.09 (m, 1H), 1.41-1.82 (m, 5H), 1.10-1.21 (m, 3H), 0.93-0.96 (m, 1H), 0.65-0.68 (m, 1H). MS (ESI) m/e [m + 1]$^+$ 395. | 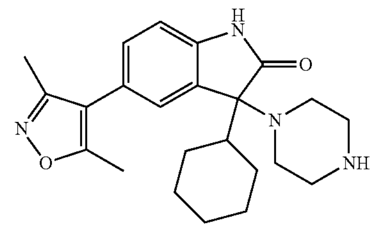 [SMILES: Cc1noc(C)c1-c1ccc2c(c1)C(C1CCCCC1)(N1CCNCC1)C(=O)N2] |
| 2.40 | 3-Cyclopentyl-5-(3,5-dimethylisoxazol-4-yl)-3-(piperazin-1-yl)indolin-2-one | (DMSO-$d_6$) $\delta_H$ 10.48 (s, 1H), 7.22 (d, J = 8.0 Hz, 1H), 7.18 (s, 1H), 6.89 (d, J = 8.0 Hz, 1H), 2.71-2.73 (m, 4H), 2.56-2.60 (m, 4H), 2.38 (s, 3H), 2.20 (s, 3H), 1.63-1.65 (m, 3H), 136-1.51 (m, 5H), 0.93-0.96 (m, 1H). MS (ESI) m/e [M + 1]$^+$ 381. | 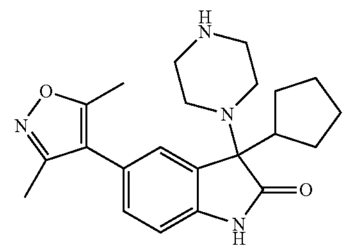 [SMILES: Cc1noc(C)c1-c1ccc2c(c1)C(C1CCCC1)(N1CCNCC1)C(=O)N2] |
| 2.41 | Tert-butyl (3r)-1-(5-(3,5-dimethylisoxazol-4-yl)-2-oxo-3-phenylindolin-3-yl)pyrrolidin-3-ylcarbamate | (DMSO-$d_6$) $\delta_H$ 10.72-10.74 (m, 1H), 7.49-7.53 (m, 2H), 7.22-7.36 (m, 5H), 6.95-6.98 (m, 1H), 3.79-3.89 (m, 1H), 2.60-2.76 (m, 2H), 2.44-2.49 (m, 1H), 2.34-2.36 (m, 3H), 2.30-2.34 (m, 1H), 2.17-2.19 (m, 3H), 1.91-2.04 (m, 1H), 1.51-1.62 (m, 1H), 1.33 (s, 9H). MS (ESI) m/e [m + 1]$^+$ 489. | 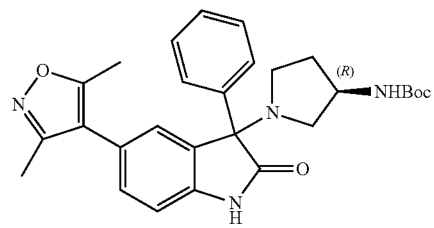 |
| 2.42 | 3-((R)-3-aminopyrrolidin-1-yl)-5-(3,5-dimethylisoxazol-4-yl)-3-phenylindolin-2-one | (DMSO-$d_6$) $\delta_H$ 10.97-10.99 (m, 1H), 7.65-7.68 (m, 2H), 7.22-7.50 (m, 5H), 6.97-7.04 (m, 1H), 3.64-3.66 (m, 1H), 2.63-3.21 (m, 3H), 2.37 (2S, 3H), 2.20 (2S, 3H), 2.12 (br, 1H), 1.76 (br, 1H). MS (ESI) m/e [M + 1]$^+$ 389. | 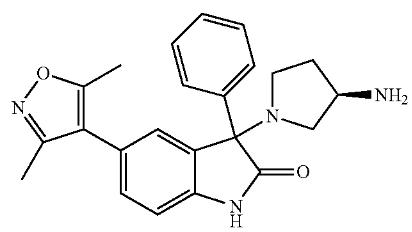 [SMILES: Cc1noc(C)c1-c1ccc2c(c1)C(c1ccccc1)(N1CC[C@@H](N)C1)C(=O)N2] |
| 2.43 | Tert-butyl (3r)-1-(5-(3,5-dimethyloxazol-4-yl)-2-oxo-3-phenylindolin-3-yl)piperidin-3-ylcarbamate | (DMSO-$d_6$) $\delta_H$ 10.66-10.68 (m, 1H), 7.48-7.53 (m, 2H), 7.21-7.37 (m, 5H), 6.93-6.96 (m, 1H), 6.63-6.70 (m, 1H), 3.37-3.51 (m, 1H), 2.55-2.71 (m, 2H), 2.36-2.37 (2S, 3H), 2.19-2.20 (2S, 3H), 1.99-2.33 (m, 3H), 1.55-1.74 (m, 2H), 1.37-1.47 (m, 1H), 1.31-1.32 (m, 9H). MS (ESI) m/e [m + 1]$^+$ 503. | 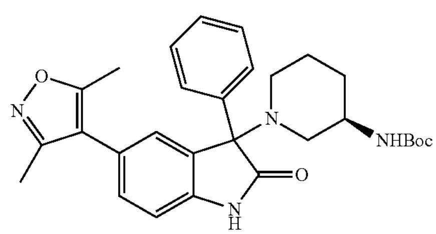 [SMILES: Cc1noc(C)c1-c1ccc2c(c1)C(c1ccccc1)(N1CCC[C@@H](NC(=O)OC(C)(C)C)C1)C(=O)N2] |
| 2.44 | Tert-butyl (3s)-1-(5-(3,5-dimethylisoxazol-4-yl)-2-oxo-3-phenylindolin-3-yl)piperidin-3-ylcarbamate | (DMSO-$d_6$) $\delta_H$ 10.67-10.69 (m, 1H), 7.48-7.53 (m, 2H), 7.21-7.37 (m, 5H), 6.93-6.96 (m, 1H), 6.63-6.70 (m, 1H), 3.37-3.51 (m, 1H), 2.55-2.71 (m, 2H), 2.36-2.37 (m, 3H), 2.19-2.20 (m, 3H), 1.99-2.33 (m, 3H), 1.55-1.74 (m, 2H), 1.37-1.47 (m, 1H), 1.31-1.32 (s, 9H). MS (ESI) m/e [m + 1]$^+$ 503. | 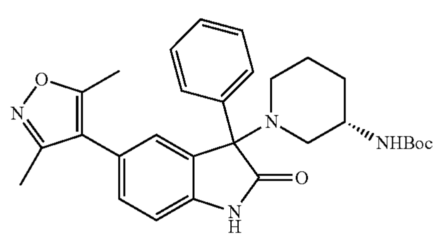 [SMILES: Cc1noc(C)c1-c1ccc2c(c1)C(c1ccccc1)(N1CCC[C@H](NC(=O)OC(C)(C)C)C1)C(=O)N2] |

| # | Name | ¹H NMR data LC/MS M/z (M + 1) | Structure |
|---|---|---|---|
| 2.45 | 3-((R)-3-aminopiperidin-1-yl)-5-(3,5-dimethylisoxazol-4-yl)-3-phenylindolin-2-one | (DMSO-d₆) δ$_H$ 10.92-10.93 (m, 1H), 8.02-8.19 (m, 3H), 7.30-7.65 (m, 7H), 7.04-7.05 (m, 1H), 5.06-5.08 (m, 2H), 2.98-3.23 (m, 2H), 2.43-2.56 (m, 5H), 2.27-2.29 (m, 3H), 1.54-1.78 (m, 4H). MS (ESI) m/e [m + 1]⁺ 403. | 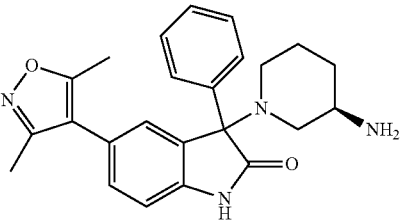 [SMILES: Cc1noc(C)c1-c1ccc2c(c1)C(c1ccccc1)(N1CCC[C@@H](N)C1)C(=O)N2] |
| 2.46 | 3-((S)-3-aminopiperidin-1-yl)-5-(3,5-dimethylisoxazol-4-yl)-3-phenylindolin-2-one | (DMSO-d₆) δ$_H$ 10.86-10.87 (m, 1H), 7.98-8.03 (m, 3H), 7.58-7.59 (m, 2H), 7.24-7.39 (m, 5H), 6.98 (d, J = 8.0 Hz, 1H), 5.11-5.14 (m, 2H), 2.87-3.19 (m, 2H), 2.62-2.70 (m, 1H), 2.37-2.39 (m, 5H), 2.20-2.22 (m, 3H), 1.64-1.92 (m, 2H), 1.38-1.56 (m, 2H). MS (ESI) m/e [m + 1]⁺ 403. | 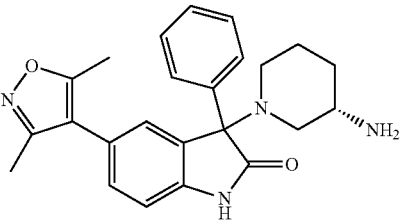 [SMILES: Cc1noc(C)c1-c1ccc2c(c1)C(c1ccccc1)(N1CCC[C@H](N)C1)C(=O)N2] |

Compound 2.47

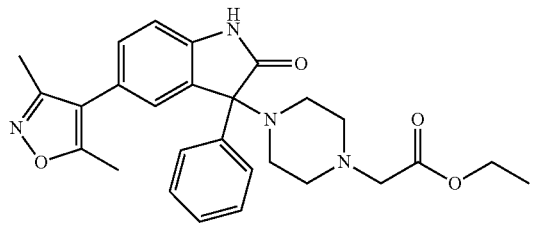 [SMILES: CCOC(=O)CN1CCN(C2(c3ccccc3)C(=O)Nc3ccc(-c4c(C)noc4C)cc32)CC1]

Ethyl 2-(4-(5-(3,5-dimethylisoxazol-4-yl)-2-oxo-3-phenylindolin-3-yl)piperazin-1-yl)acetate To a solution of 5-(3,5-dimethylisoxazol-4-yl)-3-phenyl-3-(piperazin-1-yl)indolin-2-one (194 mg, 0.5 mmol) in DMF (3.0 mL) was added ethyl 2-bromoacetate (417 mg, 2.5 mmol) and potassium carbonate (208 mg, 1.5 mmol), and the mixture was stirred in RT for 0.5 h, and then saturated NH₄Cl (10 mL) was added, and the mixture was extracted with CH₂Cl₂ (2×10 mL), combined the organic phase, dried with Na₂SO₄, concentrated in vacuo to give crude product. The mixture was purified with chromatography on column using CH₂Cl₂/MeOH (50/1, v/v) as eluting to afford a white solid (100 mg, 42%). ¹H NMR (400 MHz, DMSO-d₆): δ$_H$ 7.52 (d, J=8.0 Hz, 2H), 7.29-7.37 (m, 5H), 7.17 (d, J=8.0 Hz, 1H), 4.65 (s, 2H), 4.16 (q, J=6.8 Hz, 2H), 2.50-2.52 (m, 4H), 2.36 (s, 3H), 218 (s, 3H), 1.17 (t, J=6.8 Hz, 3H). MS (ESI) m/e [M+1]⁺ 475.

Compound 2.48

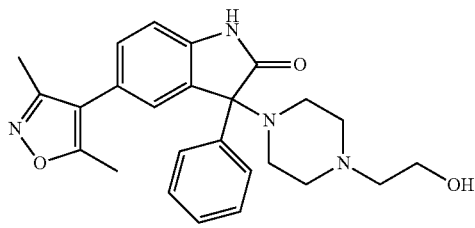 [SMILES: Cc1noc(C)c1-c1ccc2c(c1)C(c1ccccc1)(N1CCN(CCO)CC1)C(=O)N2]

5-(3,5-Dimethylisoxazol-4-yl)-3-(4-(2-hydroxyethyl)piperazin-1-yl)-3-phenylindolin-2-one To a solution of Ethyl 2-(4-(5-(3,5-dimethylisoxazol-4-yl)-2-oxo-3-phenylindolin-3-yl)piperazin-1-yl)acetate (100 mg, 0.21 mmol) in THF (5 mL) was added lithium aluminium tetrahydride (38 mg, 1.05 mmol) at 0° C., the reaction mixture was stirred at RT for 2.0 h. After cooling to 0° C., the reaction was quenched by addition of aq. saturated NH₄Cl solution (50 mL). The mixture was diluted with water and extracted with EtOAc (50 mL). The organic layer was washed with brine, dried over anhydrous MgSO4, filtered and evaporated in vacuo to yield crude product which were purified on flash column chromatography to afford the title compound as a white solid (30 mg, 33%). ¹H NMR (400 MHz, DMSO-d₆): δ H 10.69 (s, 1H), 7.22-7.51 (m, 7H), 6.96 (d, J=8.0 Hz, 1H), 4.31 (s, 1H), 3.40-3.45 (m, 2H), 2.13-2.40 (m, 13H), 2.02 (s, 3H). MS (ESI) m/e [M+1]⁺ 433.

Compound 2.49

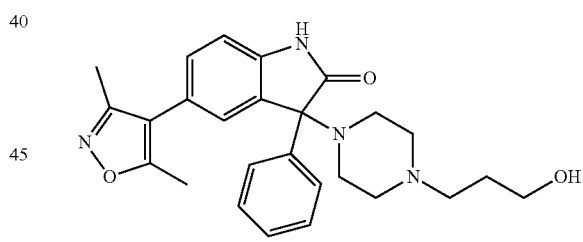

5-(3,5-Dimethylisoxazol-4-yl)-3-(4-(3-hydroxypropyl)piperazin-1-yl)-3-phenylindolin-2-one A mixture of 5-(3,5-dimethylisoxazol-4-yl)-3-phenyl-3-(piperazin-1-yl)indolin-2-one (77 mg, 0.2 mmol), 3-bromopropan-1-ol (278 mg, 2.0 mmol), and potassium carbonate (55 mg, 0.4 mmol) in DMF (3 mL) was stirred at RT for 0.5 hours, and then diluted with ethyl acetate (20 mL) and extracted with water (2×20 mL) and brine (50 mL). Aqueous layers were back washed with ethyl acetate (20 mL). Organic layers were combined, dried (MaSO₄), filtered and concentrated. Residue was purified by Pre-TLC using CH₂Cl₂/MeOH (10:1) as eluting to afford product (20 mg, 22%) as a white solid. ¹H NMR (400 MHz, DMSO-d₆): δ H 10.69 (s, 1H), 7.23-7.50 (m, 7H), 6.96 (d, J=8.0 Hz, 1H), 3.36-3.39 (m, 2H), 2.29-2.32 (m, 13H), 2.18 (s, 3H), 1.50-1.52 (m, 2H). MS (ESI) m/e [M+1]⁺ 447.

Compound 2.50a and 2.50b

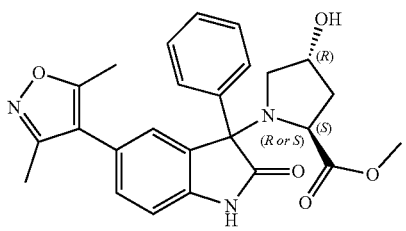

2.50a

Fast isomer in normal chromatography
Eluting reagent: DCM/MeOH = 20/1

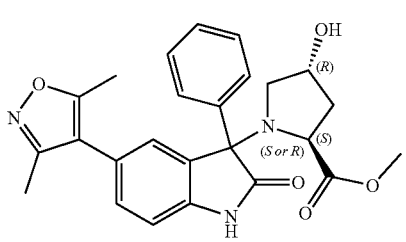

2.50b

Slow isomer in normal chromatography
Eluting reagent: DCM/MeOH = 20/1

676 mg (2.0 mmol) of 3-chloro-5-(3,5-dimethylisoxazol-4-yl)-3-phenylindolin-2-one and 544 mg (3.0 mmol) of (2S, 4R)-methyl 4-hydroxypyrrolidine-2-carboxylate were solved in CH$_2$Cl$_2$ (10 mL), the reaction solution was stirred for 0.5 h at room temperature. Subsequently, the solution was diluted with water. The aqueous phase was extracted with CH$_2$Cl$_2$ (2×10 mL). The combined organic phases were washed with aqueous NaHCO$_3$ and with water, dried and concentrated in vacuo. The resulting residue was purified by chromatography (eluent: CH$_2$Cl$_2$/MeOH=50/1) to give the fast isomer product (150 mg, 16%) and the slow isomer (140 mg, 15%) on normal phase column chromatography as white solid. The fast isomer (2.50a): $^1$H NMR (400 MHz, DMSO-d$_6$): $\delta_H$ 10.85 (s, 1H), 7.50 (d, J=8.0 Hz, 2H), 7.20-7.36 (m, 4H), 7.16 (s, 1H), 6.94 (d, J=8.0 Hz, 1H), 4.80 (d, J=5.2 Hz, 1H), 4.21-4.25 (m, 1H), 3.50-3.54 (m, 1H), 3.14 (s, 3H), 3.05-3.09 (m, 1H), 2.87-2.91 (m, 1H), 2.36 (s, 3H), 2.16 (s, 3H), 1.85-1.93 (m, 2H), MS (ESI) m/e [M+1]$^+$ 448; the slow isomer (2.50b): $^1$H NMR (400 MHz, DMSO-d$_6$): $\delta_H$ 10.82 (s, 1H), 7.50 (d, J=8.0 Hz, 2H), 7.17-7.30 (m, 5H), 6.93 (d, J=8.0 Hz, 1H), 4.91 (d, J=4.8 Hz, 1H), 4.26-4.31 (m, 1H), 4.15-4.18 (m, 1H), 3.34 (s, 3H), 3.10-3.34 (m, 1H), 2.31-2.35 (m, 4H), 2.16 (s, 3H), 1.86-1.90 (m, 2H), MS (ESI) m/e [M+1]$^+$ 448.

Compound 2.51a and 2.51b

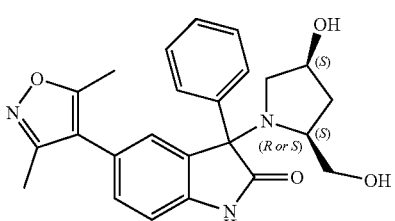

2.51a

Fast isomer in normal chromatography
Eluting reagent: DCM/MeOH = 10/1

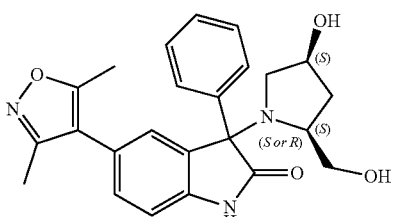

2.51b

Slow isomer in normal chromatography
Eluting reagent: DCM/MeOH = 10/1

Compounds 2.51a and 2.51b were synthesized from compounds 2.50a and 2.50b using the same procedure as described in Compound 2.48. The fast isomer (2.51a) $^1$H NMR (400 MHz, DMSO-d$_6$): $\delta$ H 10.68 (s, 1H), 7.23-7.58 (m, 6H), 6.95 (d, J=7.6 Hz, 1H), 4.70 (d, J=4.8 Hz, 1H), 4.13-4.16 (m, 21H), 2.89-3.00 (m, 4H), 2.38 (s, 3H), 2.29-2.33 (m, 1H), 2.21 (s, 3H), 1.87-1.92 (m, 1H), 1.55-1.59 (m, 1H). MS (ESI) m/e [M+1]420; the slow isomer (2.51b) $^1$H NMR (400 MHz, DMSO-d$_6$): $\delta_H$ 10.80 (s, 1H), 7.57 (d, J=8.0 Hz, 2H), 7.18-7.32 (m, 5H), 6.93 (d, J=8.0 Hz, 1H), 4.66-4.68 (m, 1H), 4.15-4.29 (m, 2H), 2.85-2.89 (m, 5H), 2.37 (s, 3H), 2.18 (s, 3H), 1.91-1.98 (m, 1H), 1.63-1.68 (m, 1H). MS (ESI) m/e [M+1]$^+$ 420.

The following compounds, compound 2.52 through 2.58, were synthesized starting from the corresponding reagent to the similar procedures described as those of compound 2.50a and 2.51a.

| # | Name | $^1$H NMR data LC/MS M/z (M + 1) | Structure |
|---|------|---------------------------------|-----------|
| 2.52 | (2S)-1-Methyl 1-(5-(3,5-dimethylisoxazol-4-yl)-2-oxo-3-phenylindolin-3-yl)pyrrolidine-2-carboxylate | (400 MHz, CDCl$_3$): $\delta_H$ 7.74-7.78 (m, 2H), 7.30-7.39 (m, 4H), 7.06-7.10 (m, 1H), 6.89-6.91 (m, 1H), 4.54-4.57 (m, 0.5 H), 3.45-3.52 (m, 1H), 3.45 (s, 1.5H), 3.40-3.43 (m, 1H), 3.31 (s, 1.5 H), 3.21-3.23 (m, 0.5 H), 2.60-2.62 (m, 1H), 2.15-2.40 (m, 7H), 1.56-2.00 (m, 4H), MS (ESI) m/e [M + 1]$^+$ 432. | 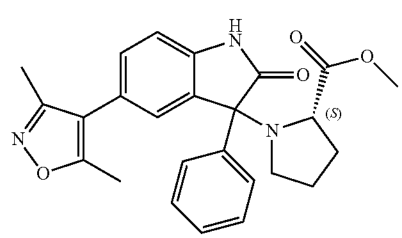 |

-continued

| # | Name | ¹H NMR data LC/MS M/z (M + 1) | Structure |
|---|---|---|---|
| 2.53 | 5-(3,5-Dimethylisoxazol-4-yl)-3-((s)-2-(hydroxymethyl)pyrrolidin-1-yl)-3-phenylindolin-2-one | (400 MHz, CDCl₃): δ$_H$ 7.99-8.05 (m, 2H), 7.42-7.49 (m, 3H), 7.22-7.26 (m, 2H), 7.02-7.05 (m, 1H), 3.45-3.88 (m, 4H), 2.05-2.42 (m, 10H). MS (ESI) m/e [M + 1]⁺ 404. | 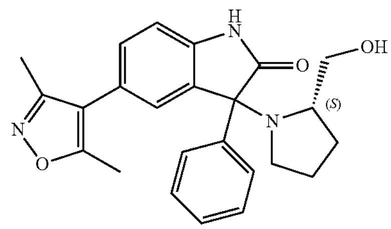 |
| 2.54 | (2R)-Methyl 1-(5-(3,5-dimethylisoxazol-4-yl)-2-oxo-3-phenylindolin-3-yl)pyrrolidine-2-carboxylate | (400 MHz, CDCl₃): δ$_H$ 7.68-7.77 (m, 2H), 7.29-7.38 (m, 4H), 7.05-7.09 (m, 1H), 6.88-6.91 (m, 1H), 4.50-4.52 (m, 0.5 H), 3.19-3.52 (m, 5.5H), 1.80-2.39 (m, 10H), 1.56-2.00 (m, 4H), MS (ESI) m/e [M + 1]⁺ 432. | 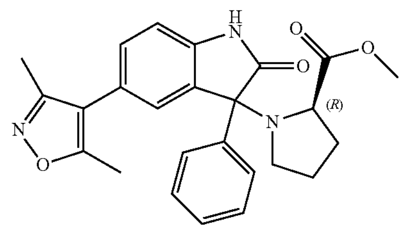 |
| 2.55 | 5-(3,5-Dimethylisoxazol-4-yl)-3-((r)-2-(hydroxymethyl)pyrrolidin-1-yl)-3-phenylindolin-2-one | (400 MHz, CDCl₃): δ$_H$ 7.94-7.99 (m, 2H), 7.43-7.48 (m, 3H), 7.22-7.26 (m, 2H), 7.02-7.05 (m, 1H), 3.43-3.90 (m, 4H), 2.07-2.43 (m, 10H). MS (ESI) m/e [M + 1]⁺ 404. | 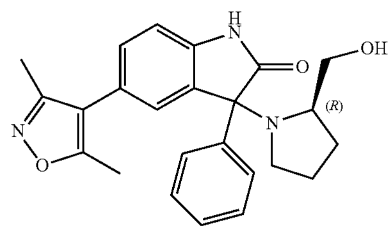 |
| 2.56 | (2R)-Methyl 2-(5-(3,5-dimethylisoxazol-4-yl)-2-oxo-3-phenylindolin-3-ylamino)-3-(1h-imidazol-5-yl)propanoate | (400 MHz, DMSO-d₆): δ$_H$ 10.67-10.73 (m, 1H), 7.21-7.40 (m, 7H), 6.88-7.00 (m, 3H), 3.43-3.64 (m, 3H), 2.78-2.83 (m, 2H), 2.13-2.37 (m, 6H). MS (ESI) m/e [M + 1]⁺ 472. | 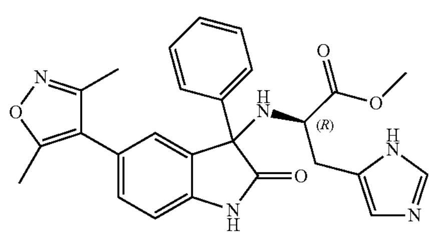 |
| 2.57 | (2S)-Methyl 2-(5-(3,5-dimethylisoxazol-4-yl)-2-oxo-3-phenylindolin-3-ylamino)-3-(1h-imidazol-5-yl)propanoate | (400 MHz, CDCl₃): δ$_H$ 7.29-7.60 (m, 6H), 6.80-7.18 (m, 4H), 3.41-3.58 (m, 4H), 2.78-2.83 (m, 2H), 2.89-2.91 (m, 2H), 2.17-2.40 (m, 6H). MS (ESI) m/e [M + 1]⁺ 472. | 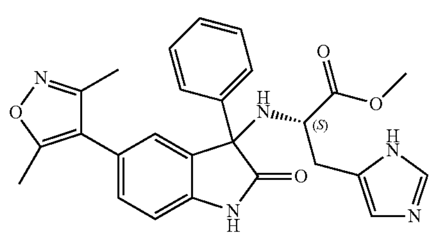 |
| 2.57a | 5-(3,5-Dimethylisoxazol-4-yl)-3-((s)-1-hydroxy-3-(1h-imidazol-5-yl)propan-2-ylamino)-3-phenylindolin-2-one | (400 MHz, CD₃OD): δ$_H$ 8.30 (s, 1H), 7.93 (s, 1H), 7.47 (d, J = 8.0 Hz, 2H), 7.19-7.31 (m, 4H), 7.04 (d, J = 8.0 Hz, 1H), 7.00 (s, H), 6.68 (s, 1H), 3.40-3.52 (m, 2H), 2.66-2.74 (m, 3H), 2.28 (s, 3H), 2.11 (s, 3H). MS (ESI) m/e [M + 1]⁺ 444. | 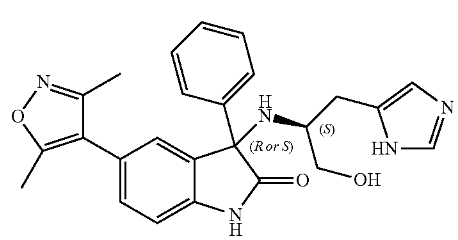 |

2.57a
Fast isomer in HPLC
Eluting reagent:
CH₃CN/H₂O = 15/1 to 20/1

-continued

| # | Name | ¹H NMR data LC/MS M/z (M + 1) | Structure |
|---|---|---|---|
| 2.57b | 5-(3,5-Dimethylisoxazol-4-yl)-3-((s)-1-hydroxy-3-(1h-imidazol-5-yl)propan-2-ylamino)-3-phenylindolin-2-one | (400 MHz, CD₃OD): δ_H 8.24-8.28 (m, 2H), 7.36 (d, J = 8.0 Hz, 2H), 7.09-7.23 (m, 7H), 7.00 (d, J = 8.0 Hz, 1H), 3.09-3.20 (m, 2H), 2.72-2.77 (m, 3H), 2.27 (s, 3H), 2.11 (s, 3H). MS (ESI) m/e [M + 1]⁺ 444. | Slow isomer in HPLC Eluting reagent: CH₃CN/H₂O = 15/1 to 20/1 |
| 2.58 | 5-(3,5-Dimethylisoxazol-4-yl)-3-(3-hydroxyazetidin-1-yl)-3-phenylindolin-2-one | (400 MHz, DMSO-d₆): δH 10.76 (s, 1H), 7.11-7.45 (m, 7H), 6.99 (d, J = 8.0 Hz, 1H), 5.29 (d, J = 5.6 Hz, 1H), 4.24-4.25 (m, 1H), 3.33-3.36 (m, 3H), 2.88-2.90 (m, 1H), 2.34 (s, 3H), 2.16 (s, 3H). MS (ESI) m/e [M + 1]⁺ 376. | 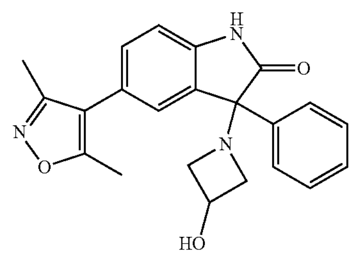 [SMILES: Cc1noc(C)c1-c1ccc2c(c1)C(c1ccccc1)(N1CC(O)C1)C(=O)N2] |

Compound 2.59

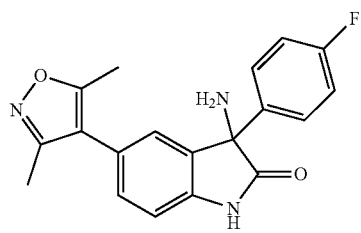 [SMILES: Cc1noc(C)c1-c1ccc2c(c1)C(N)(c1ccc(F)cc1)C(=O)N2]

Step 1:
5-bromo-3-(4-fluorophenyl)-3-hydroxyindolin-2-one

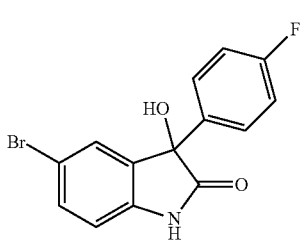 [SMILES: O=C1Nc2ccc(Br)cc2C1(O)c1ccc(F)cc1]

To a solution of 5-bromoindoline-2,3-dione (120 g, 530 mmol, 1.0 eq) in THF (1 L) was added dropwise (4-fluorophenyl)magnesium bromide in THF (0.8 M, 1.6 L, 1280 mmol, 2.4 eq) at 0° C.~15° C., the mixture was stirred for overnight at room temperature. Then mixture was cooled to 0° C., quenched with H₂O (20 mL), concentrated to give crude product, which was dissolved in EtOAc (2 L), washed with 1N HCl.aq (2 L), brine (1 L×2), dried over Na₂SO₄, the organic phase was concentrated to give crude product. Then the crude product was stirred in PE, filtered to obtained yellow solid, and dried in air to give 136 g (yield 80%) product, which was used to the next step without further purification. ¹H NMR (400 MHz, DMSO-d₆): δ_H 10.58 (s, 1H), 7.44-7.46 (dd, 1H, J₁=8.4 Hz, 2.0 Hz), 7.28-7.32 (m, 2H), 7.22-7.25 (m, 1H), 7.14-7.18 (t, 2H, J=8.8 Hz), 6.87-6.89 (d, 1H, J=8.4 Hz), 6.84 (s, 1H). MS (ESI) [M+1-18]⁺ 304, 306.

Step 2: 5-(3,5-dimethylisoxazol-4-yl)-3-(4-fluorophenyl)-3-hydroxyindolin-2-one

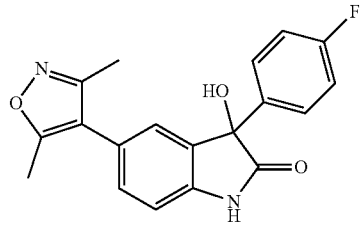 [SMILES: Cc1noc(C)c1-c1ccc2c(c1)C(O)(c1ccc(F)cc1)C(=O)N2]

A mixture of 3,5-dimethylisoxazol-4-ylboronic acid (120 g, 851 mmol, 2.0 eq), dichloro[1,1'-bis(di-tert-butylphosphino)ferrocene]palladium(II) (10 g, 13.7 mmol, 0.03 eq), 5-bromo-3-(4-fluorophenyl)-3-hydroxyindolin-2-one (136 g, 422 mmol, 1.0 eq) and Na₂CO₃ (100 g, 943 mmol, 2.2 eq) were dissolved in dioxane/H₂O (800 mL/200 mL), which was heated to reflux for 5 h under N₂ atmosphere. After cooled to room temperature, IL EA was added, the mixture was filtered through a pad of celite, the filter was washed with brine (1 L×2), dried over Na₂SO₄, concentrated, which was purified by silical gel to give 70 g yellow solid (yield, 49%). ¹H NMR (400 MHz, DMSO-d₆): δ_H 10.56 (s, 1H), 7.31-7.33 (m, 2H), 6.93 (d, J=8.0 Hz, 1H), 4.27-4.35 (m, 4H), 2.35 (s, 3H), 2.18 (s, 3H). MS (ESI) m/e [M+1]⁺ 339.

Step 3: 3-amino-5-(3,5-dimethylisoxazol-4-yl)-3-(4-fluorophenyl)indolin-2-one

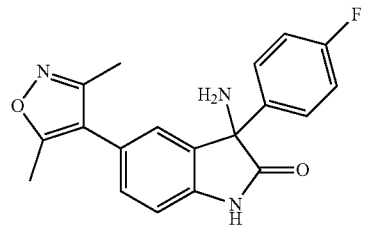 [SMILES: Cc1noc(C)c1-c1ccc2c(c1)C(N)(c1ccc(F)cc1)C(=O)N2]

Under N₂, to a solution of 5-(3,5-dimethylisoxazol-4-yl)-3-(4-fluorophenyl)-3-hydroxyindolin-2-one (52 g, 154 mmol, 1.0 eq) in THF (500 mL) was added pyridine (40 mL, 496 mmol, 3.2 eq) and SOCl₂ (16 mL, 219 mmol, 1.4 eq) slowly at −15° C.~−20° C., the mixture was stirred for 20 min at −15° C.~−20° C., quenched with brine, washed with brine (300 mL×2), to the THF layer was added NH₃/H₂O (100 mL), the mixture was stirred for 2 hours at room temperature, washed with brine, dried, concentrated, purified by silicon gel to give a crude product which was recrystallized from i-PrOH/toluene to give 14 g (yield 27%) product as white solid. ¹H NMR (DMSO-d₆) δ$_H$ 10.57 (s, 1H), 7.40-7.44 (m, 2H), 7.22-7.24 (dd, 1H, J=8.0 Hz, 1.6 Hz), 7.11-7.16 (m, 3H), 6.98-7.00 (d, 1H, J=8.0 Hz), 2.75 (s, 2H), 2.33 (s, 3H), 2.16 (s, 3H)

Compound 2.59a and 2.59b

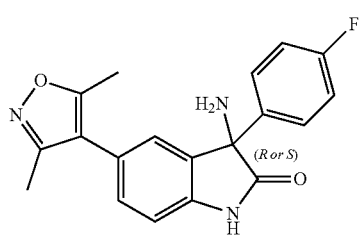

Fast isomer in chiral OJH HPLC
Eluting reagent: CO2/(MeOH70ACN30) = 70/30

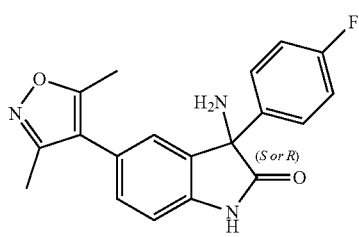

Slow isomer in chiral OJH HPLC
Eluting reagent: CO2/(MeOH70ACN30) = 70/30

Each enantiomer of racemic 2.59a and 2.59b was separated using preparative HPLC on a CHIRALPAK OJ-H with CO₂/(EtOH80ACN20)=72/28 as an eluent. The enantiomeric excesses were determined by using HPLC on a CHIRALPAK OJ-H with CO₂/(MeOH70ACN30)=70/30 as an eluent at a flow rate of 2.0 mL/min. The first one enantiomer eluted at the retention time of 3.55 min, ¹H NMR (400 MHZ, DMSO-D₆): δ$_H$ 10.57 (s, 1H), 7.11-7.44 (m, 6H), 6.98 (d, J=7.6 HZ, 1H), 2.76 (s, 2H), 2.34 (s, 3H), 2.17 (s, 3H). MS (ESI) M/E [M+1]⁺ 338; and the other enantiomer eluted at the retention time of 7.07 min, ¹H NMR (400 MHZ, DMSO-D₆): δ$_H$ 10.55 (s, 1H), 7.11-7.44 (m, 6H), 6.98 (d, J=8.0 HZ, 1H), 2.76 (s, 2H), 2.33 (s, 3H), 2.16 (s, 3H). MS (ESI) M/E [M+1]⁺ 338.

Example 3

Synthesis of Compound 3.1 through 3.10

Compound 3.1

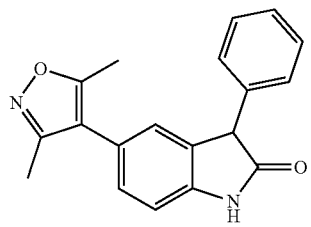 [SMILES: Cc1noc(C)c1-c1ccc2c(c1)C(c1ccccc1)C(=O)N2]

5-(3,5-Dimethylisoxazol-4-yl)-3-phenylindolin-2-one

To a solution of 5-(3,5-dimethylisoxazol-4-yl)-3-(2-hydroxyethylamino)-3-phenylindolin-2-one (32 g, 0.1 mmol) in dichloromethane (500 mL) was added trifluoroacetic acid (20 g) and triethylsilane (20 g). The brown solution was stirred at ambient temperature for 3 h and concentrated in vacuo to dryness. The residue was diluted with dichloromethane (500 mL), washed with saturated ammonium chloride solution (200 mL), brine (3×400 mL), dried over anhydrous sodium sulfate and filtered. The filtrate was concentrated in vacuo to dryness. The residue was crystallized from ether to give the title compound. ¹H NMR (400 MHz, DMSO-d₆): δ$_H$ 10.63 (s, 1H), 7.18-7.36 (m, 6H), 6.99-7.04 (m, 2H), 4.82 (s, 1H), 2.32 (s, 3H), 2.15 (s, 3H). MS (ESI) m/e [M+1]⁺ 305.

Compound 3.2

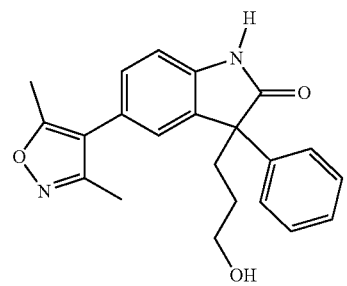 [SMILES: Cc1noc(C)c1-c1ccc2c(c1)C(CCCO)(c1ccccc1)C(=O)N2]

5-(3,5-dimethylisoxazol-4-yl)-3-(3-hydroxypropyl)-3-phenylindolin-2-one

A mixture of 5-(3,5-dimethylisoxazol-4-yl)-3-phenylindolin-2-one (1.5 g, 5 mmol), 3-bromopropan-1-ol (1.3 g, 10.0 mmol), potassium iodide (0.16 g, 1 mmol) and potassium carbonate (1.3 g, 10.0 mmol) in THF (50 mL) was heated at 60° C. for 5 hours in a capped pressure tube. The mixture was then cooled to room temperature and diluted with ethyl acetate (20 mL) and extracted with water (2×20 mL) and brine (20 mL). Aqueous layers were back washed with ethyl acetate (20 mL). Organic layers were combined, dried (MgSO4), filtered and concentrated. Residue was purified by flash chromatography (dichloromethane, then 5% ethyl acetate in dichloromethane as solvent) to give product (0.74 g, 41%). $^1$H NMR (400 MHz, DMSO-d$_6$): $\delta_H$ 10.65 (s, 1H), 7.23-7.36 (m, 7H), 7.00 (d, J=8.0 Hz, 1H), 4.39 (m, 1H), 3.31-3.33 (m, 2H), 2.37 (s, 3H), 2.18-2.28 (m, 2H), 2.16 (s, 3H), 1.21-1.27 (m, 1H), 1.02-1.06 (m, 1H) MS (ESI) m/e [M+1]$^+$ 363.

Compound 3.3

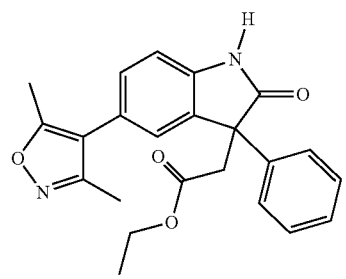 [SMILES: CCOC(=O)CC1(c2ccccc2)C(=O)Nc2ccc(-c3c(C)noc3C)cc21]

Ethyl 2-(5-(3,5-dimethylisoxazol-4-yl)-2-oxo-3-phenylindolin-3-yl)acetate

A mixture of 5-(3,5-dimethylisoxazol-4-yl)-3-phenyl indolin-2-one (260 mg, 0.85 mmol), ethyl bromoacetate (172 mg, 1.0 mmol), potassium iodide (171 mg, 1.0 mmol) and potassium carbonate (260 mg, 1.88 mmol) in acetone (10 mL) was heated at 60° C. for 15 hours in a capped pressure tube. The mixture was then cooled to room temperature and diluted with ethyl acetate (30 mL) and extracted with water (2×30 mL) and brine (20 mL). Aqueous layers were back washed with ethyl acetate (30 mL). Organic layers were combined, dried (MgSO$_4$), filtered and concentrated. Residue was purified by flash chromatography (dichloromethane, then 5% ethyl acetate in dichloromethane as solvent) to give product (200 mg, 59.9%). $^1$H NMR (400 MHz, DMSO-d$_6$): $\delta_H$ 10.61 (s, 1H), 7.21-7.39 (m, 7H), 6.97 (d, J=8.0 Hz, 1H), 3.82-3.85 (m, 2H), 3.41 (s, 3H), 2.36 (s, 3H), 2.19 (s, 3H), 0.90 (t, J=6.8 Hz, 1H). MS (ESI) m/e [M+1]$^+$ 391.

Compound 3.4

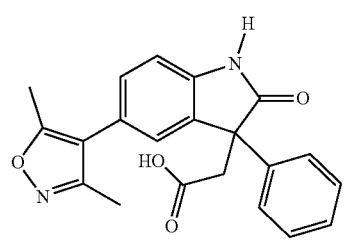 [SMILES: Cc1noc(C)c1-c1ccc2c(c1)C(CC(=O)O)(c1ccccc1)C(=O)N2]

2-(5-(3,5-dimethylisoxazol-4-yl)-2-oxo-3-phenylindolin-3-yl)acetic acid

Ethyl-2-(5-(3,5-dimethyl isoxazol-4-yl)-2-oxo-3-phenylindolin-3-yl)acetate (35 mg, 0.089 mmol) dissolved in THF/MeOH (2 mL/2 mL) was added LiOH.H$_2$O (40 mg) in H$_2$O (2 mL). The reaction was stirred at room temperature until complete consumption of the starting material as indicated by TLC. The reaction was added water, acidified with 3% HCl until pH<1 and extracted with EtOAc (3×5 mL). The combined extracts were washed with brine, dried over MgSO$_4$ and concentrated under vacuum. The title compound was purified on Pre-TLC to afford the title compound as a white solid (20 mg, 62%). $^1$H NMR (400 MHz, DMSO-d$_6$) $\delta_H$ 12.17 (s, 1H), 10.56 (s, 1H), 7.41 (s, 1H), 7.35-7.29 (m, 4H), 7.22-7.24 (m, 2H), 6.96 (d, J=8.0 Hz, 1H), 3.29-3.30 (m, 2H), 2.38 (s, 3H), 2.21 (s, 3H). MS (ESI) m/e [M+1]$^+$ 363.

Compound 3.5

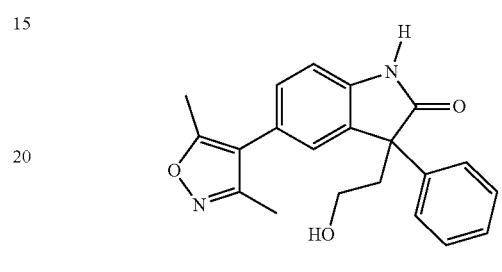

5-(3,5-Dimethylisoxazol-4-yl)-3-(2-hydroxyethyl)-3-phenylindolin-2-one

To a solution of methyl 2-(5-(3,5-dimethylisoxazol-4-yl)-2-oxo-3-phenylindolin-3-yl)acetate (50 mg, 0.13 mmol) in EtOH (20 mL) was added NaBH$_4$ (49 mg, 1.3 mmol), the reaction mixture was stirred at reflux for 3.0 h. After cooling to 0° C., the reaction was quenched by addition of aq. saturated NH$_4$Cl (2 mL) solution. The mixture was diluted with water (10 mL) and extracted with EtOAc (15 mL). The organic layer was washed with brine, dried over anhydrous MgSO$_4$, filtered and evaporated in vacuo to yield crude product which were purified on flash column chromatography to afford the title compound as a white solid (10 mg, 22%). $^1$H NMR (400 MHz, DMSO-d$_6$): $\delta_H$ 10.59 (s, 1H), 7.22-7.35 (m, 7H), 6.98 (d, J=8.0 Hz, 1H), 4.48-4.51 (m, 1H), 3.15-3.17 (m, 2H), 2.44-2.48 (m, 2H), 2.32 (s, 3H), 2.20 (s, 3H). MS (ESI) m/e [M+1]$^+$ 349.

Compound 3.6

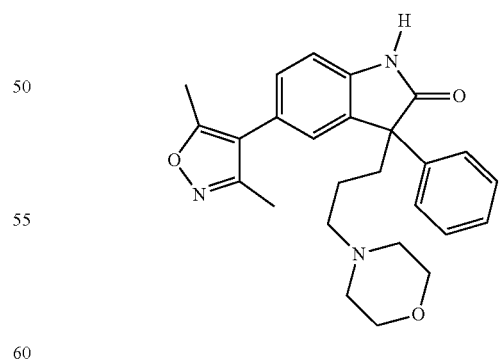

5-(3,5-dimethylisoxazol-4-yl)-3-(3-morpholinopropyl)-3-phenylindolin-2-one

A mixture of compound 5-(3,5-dimethylisoxazol-4-yl)-3-(3-hydroxypropyl)-3-phenylindolin-2-one (0.72 g, 2.0 mmol), DIPEA (1.05 mL, 6.0 mmol), MsCl (250 mg, 2.2 mmol) in CH₂Cl₂ (20 mL) was stirred at 0° C. then gradually raised to RT overnight. The contents were diluted with CH₂Cl₂, washed with water (2×10 mL), and concentrated. The crude was purified with flash chromatography to afford compound 3-(5-(3,5-dimethylisoxazol-4-yl)-2-oxo-3-phenylindolin-3-yl)propyl methanesulfonate (575 mg, 65.3%). $^1$H NMR (400 MHz, DMSO-d$_6$): $\delta_H$ 10.73 (s, 1H), 7.24-7.38 (m, 7H), 7.02 (d, J=8.0 Hz, 1H), 4.13-4.16 (m, 2H), 3.12 (s, 3H), 2.37 (s, 3H), 2.30-2.34 (m, 2H), 2.20 (s, 3H), 1.30-1.48 (m, 2H). To a stirred solution of 3-(5-(3,5-dimethylisoxazol-4-yl)-2-oxo-3-phenylindolin-3-yl)propyl methanesulfonate (440 mg, 1.0 mmol) in dry THF (10 mL) was successively added triethylamine (280 μl, 2.0 mmol) and morpholine (174 mg, 2.0 mmol) at room temperature. The reaction mixture was heated at 80° C. for 15 h and then water (10 mL) was added. The aqueous layer was extracted with dichloromethane (3×10 mL). The combined organic layers were dried over sodium sulfate and filtered. After concentration of the filtrate in vacuo, the residue was purified by chromatography on silica gel (eluent: CH₂Cl₂/MeOH: 95/5) to afford compound (385 mg, 89.3%) as a white solid. $^1$H NMR (400 MHz, CDCl₃): $\delta_H$ 7.88 (s, 1H), 7.28-7.39 (m, 5H), 7.14-7.16 (m, 1H), 7.08 (s, 1H), 7.02 (d, J=8.0 Hz, 1H), 3.76 (m, 4H), 2.45-2.55 (m, 5H), 2.37-2.39 (m, 4H), 2.22-2.29 (m, 5H), 1.54-1.55 (m, 2H). MS (ESI) m/e [M+1]⁺ 432.0.

The following compounds, compound 3.7 through 3.10, were synthesized starting from the corresponding reagent to the similar procedures described as those of compound 3.6.

| # | Name | $^1$HNMR data LC/MS M/z (M + 1) | Structure |
|---|---|---|---|
| 3.7 | 5-(3,5-Dimethylisoxazol-4-yl)-3-(3-(4-methylpiperazin-1-yl)propyl)-3-phenylindolin-2-one | (DMSO-d$_6$) $\delta_H$ 8.50 (s, 1H), 7.27-7.37 (m, 5H), 7.15 (d, J = 8.0 Hz, 1H), 7.08 (s, 1H), 7.05 (d, J = 8.0 Hz, 1H), 2.65-2.78 (m, 9H), 2.45-2.53 (m, 4H), 2.38 (s, 3H), 2.24 (s, 3H), 2.18-2.22 (m, 2H), 1.37-1.45 (m, 2H). MS (ESI) m/e [M + 1]⁺ 445. | 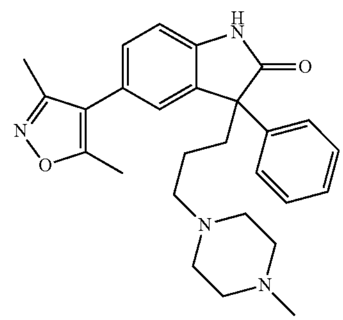 [SMILES: Cc1noc(C)c1-c1ccc2c(c1)C(CCCN1CCN(C)CC1)(c1ccccc1)C(=O)N2] |
| 3.8 | 5-(3,5-Dimethylisoxazol-4-yl)-3-phenyl-3-(3-(piperazin-1-yl)propyl)indolin-2-one | (DMSO-d$_6$) $\delta_H$ 10.64 (s, 1H), 7.22-7.35 (m, 7H), 7.00 (d, J = 8.0 Hz, 1H), 2.62-2.66 (m, 4H), 2.36 (s, 3H), 2.15-2.19 (m, 11H), 0.86-1.24 (m, 2H). MS (ESI) m/e [M + 1]⁺ 431. | 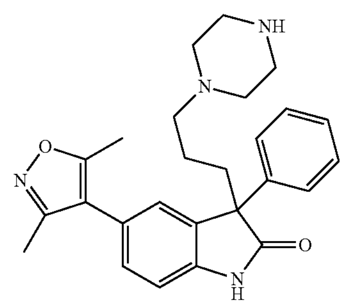 [SMILES: Cc1noc(C)c1-c1ccc2c(c1)C(CCCN1CCNCC1)(c1ccccc1)C(=O)N2] |
| 3.9 | 5-(3,5-Dimethylisoxazol-4-yl)-3-(3-(4-hydroxypiperidin-1-yl)propyl)-3-phenylindolin-2-one | (DMSO-d$_6$) $\delta_H$ 10.65 (s, 1H), 7.22-7.34 (m, 7H), 7.01 (d, J = 8.0 Hz, 1H), 4.48 (d, J = 4.0 Hz, 1H), 3.32-3.34 (m, 1H), 2.48-2.51 (m, 2H), 2.36 (s, 3H), 2.16-2.31 (m, 7H), 1.78-1.86 (m, 2H), 1.60-1.62 (m, 2), 1.18-1.35 (m, 3H), 1.02-1.05 (m, 1H). MS (ESI) m/e [M + 1]⁺ 446. | 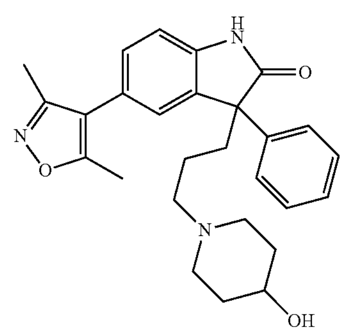 [SMILES: Cc1noc(C)c1-c1ccc2c(c1)C(CCCN1CCC(O)CC1)(c1ccccc1)C(=O)N2] |
| 3.10 | 3-(3-(Dimethylamino)propyl)-5-(3,5-dimethylisoxazol-4-yl)-3-phenylindolin-2-one | (DMSO-d$_6$) $\delta_H$ 10.65 (s, 1H), 7.23-7.36 (m, 7H), 7.01 (d, J = 8.0 Hz, 1H), 2.36 (s, 3H), 2.16-2.26 (m, 7H), 2.01 (s, 6H), 1.02-1.21 (m, 2H). MS (ESI) m/e [M + 1]⁺ 390. | 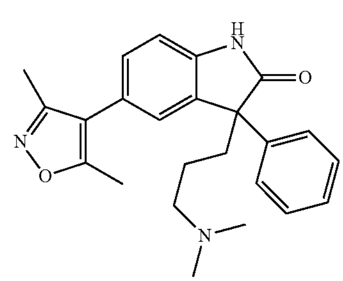 [SMILES: Cc1noc(C)c1-c1ccc2c(c1)C(CCCN(C)C)(c1ccccc1)C(=O)N2] |

Example 4

Synthesis of Compound 4.1 through 4.11

Compound 4.1 and 4.2

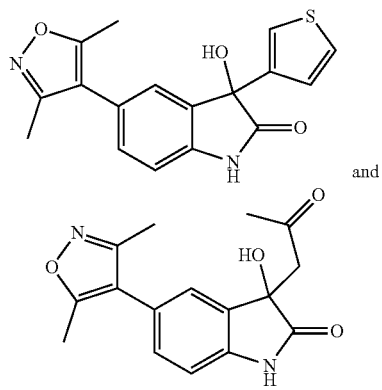

5-(3,5-Dimethylisoxazol-4-yl)-3-hydroxy-3-(thiophen-3-yl)indolin-2-one and 5-(3,5-dimethylisoxazol-4-yl)-3-hydroxy-3-(2-oxopropyl)indolin-2-one In a flame dried Schlenk tube flushed with nitrogen, 145 mg (0.56 mmol, 3 mol %) of Rh(acac)(C$_2$H$_4$)$_2$ and 405 mg (1.31 mol, 7 mol %) of triphenyl phosphite were dissolved in 200 mL of acetone. After stirring for 5 min at room temperature, 4.54 g (18.75 mmol) of substrate 5-(3,5-dimethylisoxazol-4-yl)indoline-2,3-dione and 4.8 g (37.5 mmol) of thiophen-3-ylboronic acid were added and the resulting mixture was stirred at reflux temperature. After 40 h the reaction mixture was cooled to RT and the solvent evaporated under reduced pressure. The two products were purified by column chromatography using eluent conditions reported for TLC to afford two white solid. The structures were confirmed by NMR and LC/MS. The fast compound is 5-(3,5-dimethylisoxazol-4-yl)-3-hydroxy-3-(2-oxopropyl)indolin-2-one: $^1$H NMR (400 MHz, DMSO-d$_6$): $\delta_H$ 10.33 (s, 1H), 7.26 (d, J=1.6 Hz, 1H), 7.18 (dd, J=1.6, 8.0 Hz, 1H), 6.80 (d, J=8.0 Hz, 1H), 6.12 (s, 1H), 3.35 (d, J=16.4 Hz, 1H), 3.01 (d, J=16.4 Hz, 1H), 2.37 (s, 3H), 2.19 (s, 3H), 2.02 (s, 3H). MS (ESI) m/e [M+1]$^+$ 301; and the slow compound is 5-(3,5-Dimethylisoxazol-4-yl)-3-hydroxy-3-(thiophen-3-yl)indolin-2-one: $^1$H NMR (400 MHz, DMSO-d$_6$): $\delta_H$ 10.47 (s, 1H), 7.47 (dd, J=4.8, 3.2 Hz, 1H), 7.22-7.26 (m, 3H), 7.13 (d, J=4.8 Hz, 1H), 6.96 (d, J=8.0 Hz, 1H), 6.65 (s, 1H), 2.36 (s, 3H), 2.19 (s, 3H) MS (ESI) m/e [M+1]$^+$ 327.

Example 4.1a and 4.1b 4.1a

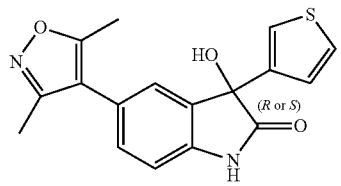 [SMILES: Cc1noc(C)c1-c1ccc2c(c1)C(Cl)(c1ccsc1)C(=O)N2]

Fast isomer in chiral SFC
Eluting reagent: CO$_2$/MeOH = 7/3

4.1b

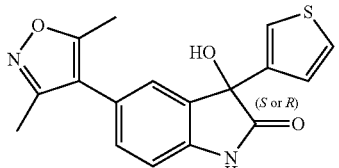

Slow isomer in chiral SFC
Eluting reagent: CO$_2$/MeOH = 7/3

Compound 4.1 was separated into two enantiomeric stereoisomers (Compound 4.1a, fast isomer, and Compound 4.1b, slow isomer) by chiral prep-HPLC. The chiral separation conditions are shown below.

| | |
|---|---|
| Column | CHIRALCEL OJ-H |
| Column size | 3 cm × 25 cm |
| Injection | 3 ml |
| Mobile phase | CO$_2$/MeOH = 80/20 |
| Flow rate | 80 ml/min |
| Wave length | UV 280 nm |
| Temperature | 35° C. |
| Sample solution | 20 mg/ml in mobile phase |
| Prep-SFC equipment | DAICEL-SFC |

Example 4.3

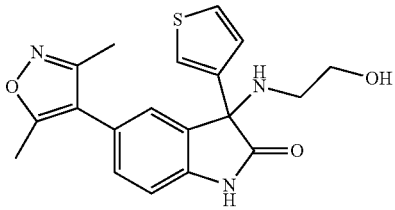 [SMILES: Cc1noc(C)c1-c1ccc2c(c1)C(NCCO)(c1ccsc1)C(=O)N2]

Step 1: 3-Chloro-5-(3,5-dimethylisoxazol-4-yl)-3-(thiophen-3-yl)indolin-2-one

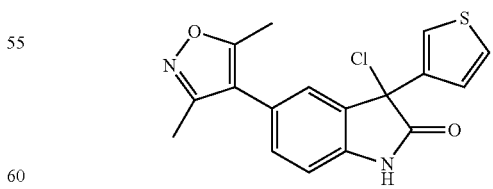

To a solution of 5-(3,5-dimethylisoxazol-4-yl)-3-hydroxy-3-(thiophen-3-yl)indolin-2-one (500 mg, 1.53 mmol) in CH$_2$Cl$_2$ (75.0 mL) was added pyridine (1.21 g, 15.3 mmol) followed by SOCl$_2$ (728 mg, 6.12 mmol) at 0° C. The reaction mixture was stirred at 0° C. for 2 h and the mixture was evaporated in vacuum to give crude product, which was used for the next step without further purification.

Step 2: 5-(3,5-Dimethylisoxazol-4-yl)-3-(2-hydroxyethylamino)-3-(thiophen-3-yl)indolin-2-one

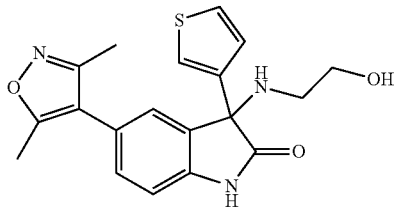

110 mg (0.33 mmol) Of 3-chloro-5-(3,5-dimethylisoxazol-4-yl)-3-(thiophen-3-yl)indolin-2-one and 220 mg (1.65 mmol) of DIPEA were dissolved in 25 ml of $CH_2Cl_2$. After the addition of 55 mg (0.65 mmol) of 2-aminoethanol, the reaction solution was stirred for 16 h at room temperature. Subsequently, the solution was diluted with water. The aqueous phase was extracted with $CH_2Cl_2$ (2×20 mL). The combined organic phases were washed with aqueous $NaHCO_3$ and with water, dried and concentrated in vacuo. The resulting residue was purified by chromatography (eluent: $CH_2Cl_2$/MeOH=20/1) to give product (85 mg, 69.8%) as a white solid. $^1$H NMR (400 MHz, DMSO-$d_6$): δ H 7.48-7.50m, 1H), 7.20-731 (m, 3H), 6.97 (d, J=8.0 Hz, 1H), 4.47 (t, J=5.6 Hz, 1H), 3.20-3.38 (m, 4H), 3.17 (d, J=5.3 Hz, 2H), 2.37 (s, 3H), 2.20 (s, 3H). MS (ESI) m/e [M+1]$^+$ 370.

The following compounds, Compound 4.4 through 4.10b, were synthesized starting from the corresponding reagent to the similar procedures described as those of compound 4.3.

| # | NAME | $^1$H NMR DATA LC/MS M/Z (M + 1) | STRUCTURE |
|---|------|-----------------------------------|-----------|
| 4.4 | 3-AMINO-5-(3,5-DIMETHYLISOXAZOL-4-YL)-3-(THIOPHEN-3-YL)INDOLIN-2-ONE | (DMSO-$d_6$) δ H 10.51 (s, 1H), 7.46-7.48 (m, 1H), 7.22-7.29 (m, 3H), 7.11 (d, J = 5.2 Hz, 1H), 6.96 (d, J = 8.0 Hz, 1H), 2.36 (s, 3H), 2.19 (m, 3H). MS (ESI) m/e [M + 1]$^+$ 326. | 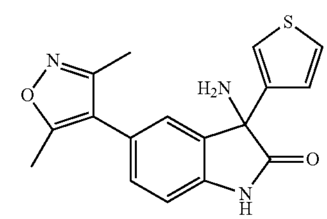 [SMILES: Cc1noc(C)c1-c1ccc2c(c1)C(N)(c1ccsc1)C(=O)N2] |
| 4.5 | 5-(3,5-DIMETHYLISOXAZOL-4-YL)-3-(4-HYDROXYPIPERIDIN-1-YL)-3-(THIOPHEN-3-YL)INDOLIN-2-ONE | (DMSO-$D_6$) ΔH 10.63 (S, 1H), 7.54-7.55 (M, 1H), 7.40-7.42 (M, 2H), 7.23 (DD, J = 8.0, 1.6 HZ, 1H), 7.14-7.15 (M, 1H), 6.93 (D, J = 8.0 HZ, 1H), 4.51 (D, J = 4.0 HZ, 1H), 3.38-3.39 (M, 1H), 2.61-2.62 (M, 2H), 2.39 (S, 3H), 2.34-2.35 (M, 1H), 2.18-2.21 (M, 4H), 1.64-1.66 (M, 2H), 1.32-1.36 (M, 2H). MS (ESI) M/E [M + 1]$^+$ 410. | 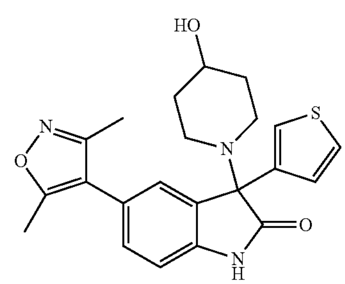 [SMILES: Cc1noc(C)c1-c1ccc2c(c1)C(c1ccsc1)(N1CCC(O)CC1)C(=O)N2] |
| 4.6A | 3-((R)-3-AMINOPIPERIDIN-1-YL)-5-(3,5-DIMETHYLISOXAZOL-4-YL)-3-(THIOPHEN-3-YL)INDOLIN-2-ONE | (DMSO-$d_6$) δH 10.81 (s, 1H), 7.96 (br s, 2H), 7.57-7.60 (m, 3H), 7.24-7.26 (m, 2H), 6.95 (d, J = 8.0, 1H), 4.43 (br s, 2H), 3.16-3.19 (m, 1H), 2.87-2.90 (m, 1H), 2.32-2.47 (m, 6H), 2.24 (s, 3H), 1.65-1.77 (m, 2H), 1.42-1.51 (m, 2H). MS (ESI) m/e [M + 1]$^+$ 409. | 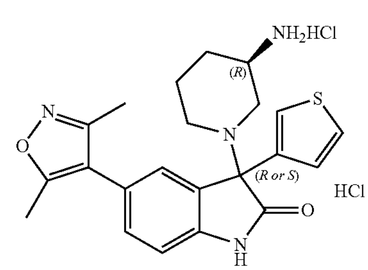 |

4.6a
Fast isomer in chiral AD HPLC
Eluting reagent:
Hexane/EtOH/Et$_3$N = 80/20/0.1

| # | NAME | ¹H NMR DATA LC/MS M/Z (M + 1) | STRUCTURE |
|---|------|-------------------------------|-----------|
| 4.6B | 3-((R)-3-AMINOPIPERIDIN-1-YL)-5-(3,5-DIMETHYL-ISOXAZOL-4-YL)-3-(THIOPHEN-3-YL)INDOLIN-2-ONE | (DMSO-d₆) δH 10.84 (s, 1H), 7.98 (br s, 2H), 7.57-7.62 (m, 3H), 7.25-7.27 (m, 2H), 6.97 (d, J = 8.0, 1H), 5.03 (br s, 2H), 3.13-3.16 (m, 1H), 2.82-2.87 (m, 1H), 2.64-2.67 (m, 1H), 2.36-2.47 (m, 5H), 2.24 (s, 3H), 1.80-1.84 (m, 1H), 1.60-1.67 (m, 1H), 1.33-1.43 (m, 2H). MS (ESI) m/e [M + 1]⁺ 409. | 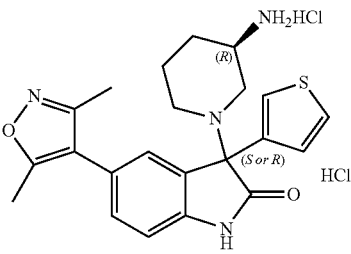<br>4.6b<br>Slow isomer in chiral AD HPLC<br>Eluting reagent:<br>Hexane/EtOH/Et₃N = 80/20/0.1 |
| 4.7A | 3-((S)-3-AMINOPIPERIDIN-1-YL)-5-(3,5-DIMETHYLISOXAZOL-4-YL)-3-(THIOPHEN-3-YL)INDOLIN-2-ONE | (DMSO-d₆) δH 10.63 (s, 1H), 7.54 (dd, J = 3.2, 4.8, 1H), 7.43 (dd, J = 1.2, 4.8, 1H), 7.35 (d, J = 1.2, 1H), 7.23 (dd, J = 1.6, 8.0, 1H), 7.15-7.16 (m, 1H), 6.93 (d, J = 8.0, 1H), 2.66-2.68 (m, 1H), 2.51-2.59 (m, 3H), 2.39 (s, 3H), 2.25-2.27 (m, 1H), 2.22 (s, 3H), 1.88-1.92 (m, 1 H), 1.64-1.69 (m, 1H), 1.50-1.55 (m, 1H), 1.34-1.40 (m, 1h). MS (ESI) m/e [M + 1]⁺ 409. | 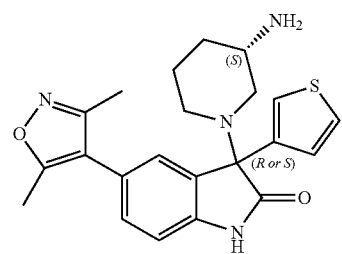<br>4.7a<br>Fast isomer in chiral AD HPLC<br>Eluting reagent:<br>Hexane/EtOH/Et₃N = 80/20/0.1 |
| 4.7B | 3-((S)-3-AMINOPIPERIDIN-1-YL)-5-(3,5-DIMETHYLISOXAZOL-4-YL)-3-(THIOPHEN-3-YL)INDOLIN-2-ONE | (DMSO-d₆) δH 10.58 (s, 1H), 7.54 (dd, J = 2.8, 4.8, 1H), 7.43 (dd, J = 1.2, 4.8, 1H), 7.35 (d, J = 1.2, 1H), 7.23 (dd, J = 1.6, 8.0, 1H), 7.14-7.15 (m, 1H), 6.93 (d, J = 8.0, 1H), 2.60-2.62 (m, 2H), 2.39 (s, 3H), 2.22 (s, 3H), 2.15-2.17 (m, 1H), 1.97-2.02 (m, 2H), 1.53-1.67 (m, 3H), 1.31-1.36 (m, 1H). MS (ESI) m/e [M + 1]⁺ 409. | 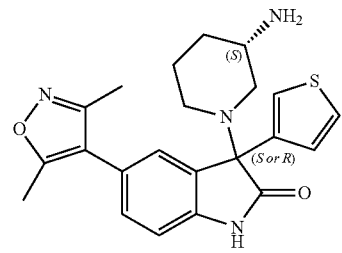<br>4.7b<br>Slow isomer in chiral AD HPLC<br>Eluting reagent:<br>Hexane/EtOH/Et₃N = 80/20/0.1 |
| 4.8 | 5-(3,5-dimethylisoxazol-4-yl)-3-(3-hydroxypiperidin-1-yl)-3-(thiophen-3-yl)indolin-2-one | (DMSO-d₆) δH 10.65 (s, 1H), 7.54-7.55 (m, 1H), 7.42-7.44 (m, H), 7.36 (s, 1H), 7.22-7.25 (m, 1H), 7.16-7.17 (m, 1H), 6.93 (d, J = 8.0 Hz, 1H), 3.39-3.45 (m, 1H), 2.67-2.76 (m, 2H), 2.39 (s, 3H), 2.21 (s, 3H), 1.99-2.08 (m, 2H), 1.52-1.77 (m, 2H), 1.29-1.37 (m, 2H). MS (ESI) m/e [M + 1]⁺ 410. | 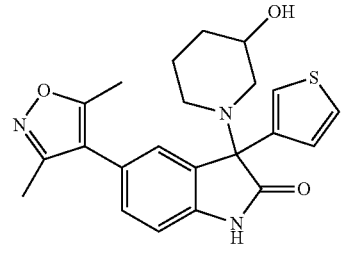<br>4.8 |

| # | NAME | ¹H NMR DATA LC/MS M/Z (M + 1) | STRUCTURE |
|---|------|-------------------------------|-----------|
| 4.9a | (R)-5-(3,5-dimethylisoxazol-4-yl)-3-((R)-3-hydroxypiperidin-1-yl)-3-(thiophen-3-yl)indolin-2-one | (DMSO-d₆) δH 10.66 (s, 1H), 7.54-7.56 (m, 1H), 7.44 (d, J = 5.2 Hz, 1H), 7.36 (s, 1H), 7.22-7.25 (m, 1H), 7.18 (s, 1H), 6.94 (d, J = 8.0 Hz, 1H), 3.33-3.34 (m, 1H), 2.74-2.76 (m, 1H), 2.39 (s, 3H), 2.15-2.45 (m, 4H), 1.92-2.00 (m, 2H), 1.53-1.78 (m, 2H), 1.29-1.37 (m, 1H), 1.01-1.04 (m, 1H). MS (ESI) m/e [M + 1]⁺ 410. | 4.9a<br>Fast isomer in normal chromatography<br>Eluting reagent: DCM/MeOH = 15/1 |
| 4.9b | (R)-5-(3,5-dimethylisoxazol-4-yl)-3-((R)-3-hydroxypiperidin-1-yl)-3-(thiophen-3-yl)indolin-2-one | (DMSO-d₆) δH 10.64 (s, 1H), 7.54-7.56 (m, 1H), 7.44 (d, J = 1.2, 5.2 Hz, 1H), 7.36 (d, J = 1.6 Hz, 1H), 7.23 (dd, J = 1.6, 8.0 Hz, 1H)), 7.16-7.18 (m, 1H), 6.93 (d, J = 8.0 Hz, 1H), 4.53 (d, J = 3.6 Hz, 1H), 3.39-3.42 (m, 1H), 2.61-2.71 (m, 1H), 2.52-2.56 (m, 1H), 2.38 (s, 3H), 2.21 (s, 3H), 2.03-2.11 (m, 2H), 1.53-1.78 (m, 2H), 1.30-1.34 (m, 1H), 1.01-1.04 (m, 1H). MS (ESI) m/e [M + 1]⁺ 410. | 4.9b<br>Slow isomer in normal chromatography<br>Eluting reagent: DCM/MeOH = 15/1 |
| 4.10a | (R)-5-(3,5-dimethylisoxazol-4-yl)-3-((S)-3-hydroxypiperidin-1-yl)-3-(thiophen-3-yl)indolin-2-one | (DMSO-d₆) δH 10.65 (s, 1H), 7.54-7.56 (m, 1H), 7.44 (dd, J = 1.2, 5.2 Hz, 1H), 7.35 (d, J = 1.2 Hz, 1H), 7.23 (dd, J = 1.6, 8.0 Hz, 1H)), 7.16-7.18 (m, 1H), 6.94 (d, J = 8.0 Hz, 1H), 4.54 (d, J = 2.4 Hz, 1H), 3.38-3.40 (m, 1H), 2.73-2.76 (m, 1H), 2.52-2.56 (m, 1H), 2.38 (s, 3H), 2.21 (s, 3H), 1.90-2.00 (m, 2H), 1.53-1.78 (m, 2H), 1.30-1.34 (m, 1H), 1.01-1.04 (m, 1H). MS (ESI) m/e [M + 1]⁺ 410. | 4.10a<br>Fast isomer in normal chromatography<br>Eluting reagent: DCM/MeOH = 15/1 |
| 4.10b | (R)-5-(3,5-dimethylisoxazol-4-yl)-3-((S)-3-hydroxypiperidin-1-yl)-3-(thiophen-3-yl)indolin-2-one | (DMSO-d₆) δH 10.65 (s, 1H), 7.54-7.56 (m, 1H), 7.43 (dd, J = 1.2, 5.2 Hz, 1H), 7.36 (d, J = 1.6 Hz, 1H), 7.23 (dd, J = 1.6, 8.0 Hz, 1H)), 7.16-7.17 (m, 1H), 6.93 (d, J = 8.0 Hz, 1H), 4.53 (d, J = 2.8 Hz, 1H), 3.38-3.40 (m, 1H), 2.67-2.69 (m, 1H), 2.52-2.56 (m, 1H), 2.39 (s, 3H), 2.21 (s, 3H), 2.03-2.08 (m, 2H), 1.54-1.77 (m, 2H), 1.27-1.34 (m, 1H), 1.01-1.04 (m, 1H). MS (ESI) m/e [M + 1]⁺ 410. | 4.10b<br>Slow isomer in normal chromatography<br>Eluting reagent: DCM/MeOH = 15/1 |

Example 4.11

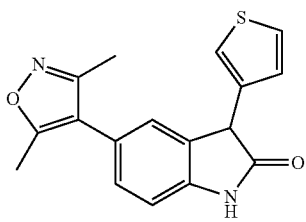 [SMILES: Cc1noc(C)c1-c1ccc2c(c1)C(c1ccsc1)C(=O)N2]

5-(3,5-Dimethylisoxazol-4-yl)-3-(thiophen-3-yl)
indolin-2-one

To a solution of 5-(3,5-dimethylisoxazol-4-yl)-3-hydroxy-3-(thiophen-3-yl)indolin-2-one (50 mg, 0.153 mmol) in trifluoroacetic acid (10 mL) was added triethylsilane (5 mL). The brown solution was stirred at ambient temperature for 3 h and concentrated in vacuo to dryness. The residue was diluted with dichloromethane (20 mL), washed with saturated ammonium chloride solution (10 mL), brine (3×20 mL), dried over anhydrous sodium sulfate and filtered. The filtrate was concentrated in vacuo to dryness. The residue was purified with chromatography on column to give the title compound (37 mg, 78.0%). $^1$H NMR (400 MHz, DMSO-d$_6$): $\delta_H$ 10.62 (s, 1H), 7.53 (m, 1H), 7.31-7.32 (m, 1H), 7.22 (d, J=8.0 Hz, 1H), 7.16 (s, 1H), 7.02-7.03 (m, 1H), 6.97 (d, J=8.0 Hz, 1H), 4.90 (s, 1H), 2.35 (s, 3H), 2.18 (s, 3H). MS (ESI) m/e [M+1]$^+$ 311.

Example 5.1

Synthesis of Compound 5.1

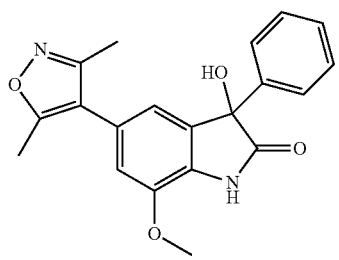 [SMILES: COc1cc(-c2c(C)noc2C)cc2c1NC(=O)C2(O)c1ccccc1]

Step 1: N-(4-bromo-2-methoxyphenyl)-2-(hydroxyimino)acetamide

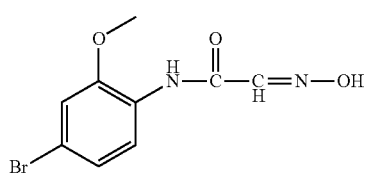

Hydroxylamine hydrochloride (6.67 g, 96 mmol) in water (15 mL) was added to a suspension of 2,2,2-trichloro-1-ethoxyethanol (6.96 g, 36 mmol) and sodium sulfate (38.3 g, 270 mmol) in water (45 mL) and 2N HCl (30 mL). The mixture was stirred at 60° C. for 20 min. 4-Bromo-2-methoxybenzenamine (6.06 g, 30 mol) in 2N HCl (30 mL) was added, and the mixture was heated to 90° C. for 2 h. The mixture was cooled to room temperature. The solid was collected by filtration, washed with water, and air dried to afford the title compound (5.55 g, crude, 68% yield). This material was used in the next step without further purification. MS (ESI) m/e [M+1]$^+$ 273, 275.

Step 2: 5-Bromo-7-methoxyindoline-2,3-dione

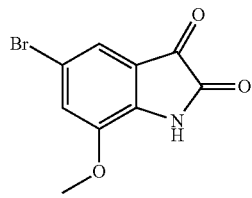

To concentrated H$_2$SO$_4$ (30 ml) at 65° C. was added N-(4-bromo-2-methoxyphenyl)-2-(hydroxyimino)acetamide (5.55 g, 20 mmol) portionwise. The mixture was heated at 90° C. for 1.5 h. The mixture was cooled to room temperature, poured onto ice, and stirred for 10 min. The solid was collected by filtration, washed with water, and air dried to afford 5-Bromo-7-methoxyindoline-2,3-dione (3.6 g, crude, 70% yield). This material was used without further purification. $^1$H NMR (400 MHz, DMSO-d$_6$): $\delta_H$ 7.93 (s, 1H), 7.38 (s, 1H), 3.94 (s, 3H). MS (ESI) m/e [M+1]$^+$ 256, 258.

Step 3: 5'-Bromo-7'-methoxyspiro[[1,3]dioxolane-2,3'-indolin]-2'-one

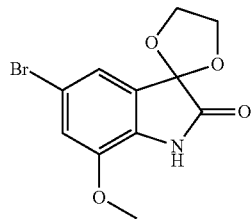

A stirred mixture of 5-bromo-7-methoxyindoline-2,3-dione (3.6 g, 14 mmol), p-TSA (1.14 g, 6 mmol) and toluene (100 mL) was refluxed using a Dean-Stark apparatus for 0.2 h. Ethylene glycol (9.3 g, 150 mmol, 10.7 eq.) was added and refluxed using a Dean-Stark apparatus for another 2 hours. The mixture was cooled and concentrated to 20 mL. EtOAc (100 mL) was added, washed with water (20 mL), brine (50 mL×2), dried over Na$_2$SO$_4$, filtered and concentrated under reduced pressure. Purified by column (CH$_2$CL$_2$/EtOAc=8:1) to give the desired product as a light brown solid (0.21 g, crude, 5%). $^1$H NMR (400 MHz, DMSO-d$_6$): $\delta_H$ 10.66 (s, 1H), 7.48 (s, 1H), 7.26-7.27 (m, 1H), 7.13-7.14 (m, 1H), 4.25-4.31 (m, 4H), 3.86 (s, 3H). MS (ESI) m/e [M+1]+ 300/302.

Step 4: 5'-(3,5-Dimethylisoxazol-4-yl)-7'-methoxyspiro[[1,3]dioxolane-2,3'-indolin]-2'-one

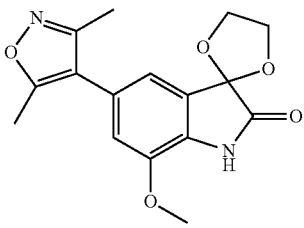 [SMILES: COc1cc(-c2c(C)noc2C)cc2c1NC(=O)C21OCCO1]

A mixture of 3,5-dimethylisoxazol-4-ylboronic acid (298 mg, 2.1 mmol), dichloro[1,1'-bis(di-tert-butylphosphino)ferrocene]palladium(II) (29 mg, 0.14 mmol), 5'-bromo-7'-methoxyspiro[[1,3]dioxolane-2,3'-indolin]-2'-one (210 mg, 0.7 mmol) and Na₂CO₃ (233 mg, 2.1 mmol) in dioxane (9 mL) and water (2 mL) was heated to 102° C. for 16 h. To the mixture was added EtOAc (50 mL), water (20 mL). The organic layer was separated and washed with water (20 mL), brine (10 mL), dried over Na₂SO₄, filtered and concentrated in vacuo. Purification by column chromatography, using a mixture of 33% EtOAc in dichloromethane as the eluent, to give the desired product as a light brown solid (57 mg, crude, 26%). ¹H NMR (400 MHz, DMSO-d₆): $\delta_H$ 10.62 (s, 1H), 7.02-7.03 (m, 1H), 6.92-6.93 (m, 1H), 4.26-4.34 (m, 4H), 3.86 (s, 3H), 2.38 (s, 3H), 2.10 (s, 3H). MS (ESI) m/e [M+1]+ 317.

Step 5: 5-(3,5-Dimethylisoxazol-4-yl)-7-methoxyindoline-2,3-dione

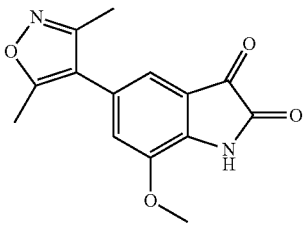 [SMILES: COc1cc(-c2c(C)noc2C)cc2c1NC(=O)C2=O]

A solution of compound 5'-(3,5-dimethylisoxazol-4-yl)-7'-methoxyspiro[[1,3]dioxolane-2,3'-indolin]-2'-one (57 mg, 0.18 mmol), acetic acid (1 mL), and hydrogen chloride solution (4 mL) was heated to 90° C. After 1.5 h, the mixture was cooled, EtOAc (20 mL) was added, washed with brine (15 mL×3), dried over Na₂SO₄, concentrated in vacuo to give the expected compound 5-(3,5-dimethylisoxazol-4-yl)-7-methoxyindoline-2,3-dione as a dark red solid (50 mg, crude, 102%). This material was used in the next step without further purification. MS (ESI) m/e [M+1]+ 273.

Step 6: 5-(3,5-Dimethylisoxazol-4-yl)-3-hydroxy-7-methoxy-3-phenylindolin-2-one

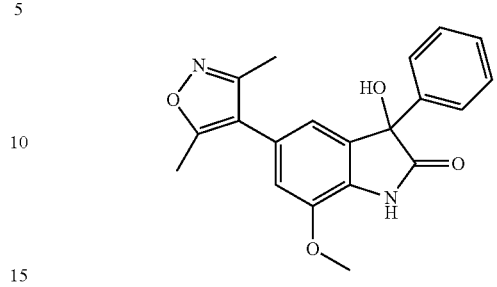

A suspension of 5-(3,5-dimethylisoxazol-4-yl)-7-methoxyindoline-2,3-dione (45 mg, 0.165 mmol) and anhydrous THF (1.5 mL) was added dropwise a solution of phenylmagnesium bromide in 2-methyltetrahydrofuran (2.9 M/L, 0.3 mL, 0.87 mmol). The reaction mixture was stirred for 3 hours at room temperature. The reaction mixture was diluted with EtOAc (30 mL), washed with saturated aqueous NH₄Cl (10 mL), brine (3×10 mL), dried over anhydrous Na₂SO₄, filtered, and concentrated in vacuo, purified by pre-TLC (CH₂Cl₂:EtOAc=3:2) to give the desired product as a light brown solid (28 mg, 48%). ¹H NMR (400 MHz, DMSO-d₆). $\delta_H$ 10.56 (s, 1H), 7.31-7.32 (m, 5H), 6.95-6.96 (m, 1H), 6.69-6.71 (m, 2H), 3.89 (s, 3H), 2.35 (s, 3H), 2.18 (s, 3H). MS (ESI) m/e [M+1]+ 351.

Example 6

Synthesis of Compound 6.0

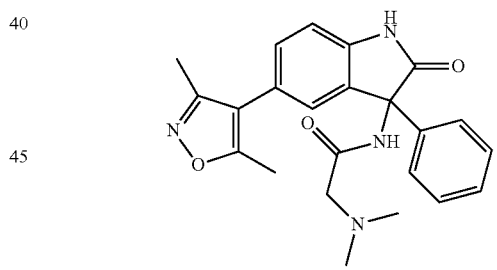

2-(Dimethylamino)-N-(5-(3,5-dimethylisoxazol-4-yl)-2-oxo-3-phenylindolin-3-yl)acetamide A mixture of 2-(dimethylamino)acetic acid hydrochloride (87 mg, 0.62 mmol), HATU (118 mg, 0.31 mmol), and Et₃N (94 mg, 0.93 mmol) in CH₂Cl₂ (10 mL) was stirred at RT for 0.5 hours, and then 3-amino-5-(3,5-dimethylisoxazol-4-yl)-3-phenylindolin-2-one (100 mg, 0.31 mmol) was added and the mixture was stirred for another 12 h. And water (10 mL) was added, the mixture was extracted with CH₂Cl₂ (2×20 mL), combined organic phase, washed with brine (20 mL), dried with Na₂SO₄, concerned in vacuo, the mixture was purified with column chromatography to give product (50 mg, 40%) as a solid. ¹H NMR (400 MHz, DMSO-d₆): $\delta_H$ 10.70 (s, 1H), 9.74 (s, 1H), 7.26-7.40 (m, 7H), 6.99 (d, J=8.0

Hz, 1H), 4.07 (d, J=16.0 Hz, 1H), 3.93 (d, J=16.0 Hz, 1H), 2.78 (s, 3H), 2.71 (s, 3H), 2.38 (s, 3H), 2.20 (s, 3H). MS (ESI) m/e [M+1]$^+$ 405.

BRD2, BRD3, BRD4 and BRDT Biochemical IC$_{50}$ Assay

Compounds disclosed herein were tested against BRD2, BRD3, BRD4 and BRDT in a time-resolved fluorescence resonance energy transfer (TR-FRET) methodology. Recombinant human BRD2(1-473), BRD3(1-435), BRD4(1-477) and BRDT(1-397) were expressed and purified from *E. coli* with an N-terminal His tag. The assay was carried out in binding mixtures of the bromodomain protein, 0-10 μM compounds and tetra-acetylated histone peptide (SGRG$_{AC}$-KG-G$_{AC}$-KGLG$_{AC}$-KGGA$_{AC}$-KRHGSGSK-biotin) in buffer containing 25 mM HEPES pH 7.5, 100 mM NaCl, 0.1% BSA, 0.05% CHAPS, and detection reagents. The detection reagents, including streptavidin-labeled Tb cryptate and XL665-labeled anti-6×His antibody, were added after binding equilibrium was achieved for protein, compound and peptide. Upon further incubation for 1 hr, the TR-FRET signals were recorded on a BMG PHERAstar FS instrument. The IC$_{50}$ for each compound was derived from fitting the % INH data to the four-parameter non-linear regression equation by Graphpad Prism software: Four-parameter equation: Y=Bottom+(Top−Bottom)/(1+10^((Log IC$_{50}$−X)*HillSlope)). Y is % inhibition at concentration X of the compound. X is Log of compound concentration. Bottom is the bottom of the curve effect. Top is the top of the curve effect. HillSlope is the hill slope factor.

Compounds 1.1-6.0 inhibited BRD2/BRD3/BRD4/BRDT with IC$_{50}$ values ranging from 0.1 nM to 10 μM.

TABLE A

IC$_{50}$s and EC$_{50}$s (nM)

| Compound No. | BRD2 IC50 | BRD3 IC50 | BRD4 IC50 | BRDT IC50 | MV4-11 (3 Days) EC50 |
|---|---|---|---|---|---|
| 1.1 | | | 51 | | 124 |
| 1.1a | | | 35 | | 58 |
| 1.1b | | | 7000 | | |
| 1.2 | | | 260 | | 364 |
| 1.3 | | | 380 | | 369 |
| 1.4 | | | 100 | | 181 |
| 1.5 | | | 180 | | 285 |
| 1.6 | | | 380 | | 594 |
| 1.7 | | | 570 | | 1498 |
| 1.8 | | | 200 | | 425 |
| 1.9 | | | 410 | | 536 |
| 1.10 | | | 1300 | | |
| 1.11 | | | 2500 | | |
| 1.12 | | | 2300 | | |
| 1.13 | | | 560 | | 746 |
| 1.14 | | | 98 | | |
| 1.15 | | | 77 | | 183 |
| 1.16 | 380 | 140 | 630 | 510 | |
| 1.17 | | | 270 | | 671 |
| 1.18 | | | 510 | | 1137 |
| 1.19 | | | 850 | | 1965 |
| 1.20 | | | 2300 | | |
| 1.21 | | | 1200 | | |
| 1.22 | | | 220 | | 478 |
| 1.23 | | | 2500 | | |
| 1.24 | | | 430 | | 934 |
| 1.25 | | | 540 | | 1535 |
| 1.26 | | | 3200 | | |
| 1.27 | | | 2800 | | |
| 1.28 | | | 3900 | | |
| 1.29 | | | 1600 | | |
| 1.30a | 52 | 25 | 70 | 58 | |
| 1.30b | | | 650 | | |
| 1.31 | | | 58 | | 152 |
| 1.32 | | | 79 | | 82 |

TABLE A-continued

IC$_{50}$s and EC$_{50}$s (nM)

| Compound No. | BRD2 IC50 | BRD3 IC50 | BRD4 IC50 | BRDT IC50 | MV4-11 (3 Days) EC50 |
|---|---|---|---|---|---|
| 1.33 | | | 82 | | 307 |
| 1.34 | | | 150 | | |
| 2.1 | | | 70 | | 78 |
| 2.2 | 55 | 35 | 150 | 95 | 283 |
| 2.2a | | | 24 | | 159 |
| 2.2b | | | 3600 | | >10000 |
| 2.3 | | | 84 | | 542 |
| 2.4 | | | 36 | | 76 |
| 2.5 | | | 110 | | 420 |
| 2.6 | | | 63 | | 179 |
| 2.7a | | | >10000 | | |
| 2.7b | | | 810 | | |
| 2.8a | | | 510 | | |
| 2.8b | | | 2200 | | |
| 2.9a | | | 860 | | |
| 2.9b | | | 25 | | |
| 2.10a | 24 | 23 | 57 | 69 | |
| 2.10b | | | 370 | | |
| 2.11a | | | 3600 | | |
| 2.11b | | | 150 | | 180 |
| 2.12a | | | 89 | | 144 |
| 2.12b | | | 3400 | | |
| 2.13a | | | 710 | | |
| 2.13b | | | 81 | | 140 |
| 2.14a | | | 78 | | 115 |
| 2.14b | | | 610 | | |
| 2.15 | | | 44 | | 95 |
| 2.16 | 9.6 | 9.9 | 19 | 23 | |
| 2.17 | | | 40 | | 363 |
| 2.17a | | | 27 | | |
| 2.17b | | | 26 | | |
| 2.18 | | | 85 | | 204 |
| 2.19a | | | >10000 | | |
| 2.19b | | | 170 | | 282 |
| 2.20a | | | 5100 | | |
| 2.20b | | | 350 | | 377 |
| 2.21 | | | 88 | | 270 |
| 2.22 | 32 | 23 | 81 | 42 | 116 |
| 2.23 | | | 160 | | 371 |
| 2.24 | | | 75 | | 349 |
| 2.25 | | | 3700 | | |
| 2.26 | | | 110 | | 204 |
| 2.27 | | | 85 | | 833 |
| 2.28 | | | 140 | | 539 |
| 2.29 | | | 94 | | 314 |
| 2.30 | | | 61 | | |
| 2.31 | | | 37 | | |
| 2.32 | | | 60 | | |
| 2.33 | | | 120 | | |
| 2.34 | | | 120 | | 438 |
| 2.35 | | | 130 | | 324 |
| 2.36 | | | 180 | | 596 |
| 2.37 | | | 93 | | |
| 2.37a | | | 54 | | |
| 2.37b | | | 1100 | | |
| 2.38 | | | 120 | | 504 |
| 2.39 | | | 76 | | 365 |
| 2.40 | | | 150 | | 555 |
| 2.41 | | | 440 | | |
| 2.42 | | | 27 | | |
| 2.43 | | | 510 | | |
| 2.44 | | | 1100 | | |
| 2.45 | | | 26 | | |
| 2.46 | 6.6 | 5.3 | 11 | 14 | |
| 2.47 | | | 54 | | |
| 2.48 | | | 80 | | |
| 2.49 | | | 84 | | |
| 2.50a | | | 460 | | 681 |
| 2.50b | | | 850 | | |
| 2.51a | | | 1400 | | |
| 2.51b | | | 67 | | |
| 2.52 | | | 190 | | |
| 2.53 | | | 90 | | |
| 2.54 | | | 220 | | |

TABLE A-continued
IC$_{50}$s and EC$_{50}$s (nM)
| Compound No. | BRD2 IC50 | BRD3 IC50 | BRD4 IC50 | BRDT IC50 | MV4-11 (3 Days) EC50 |
|---|---|---|---|---|---|
| 2.55 | | | 110 | | |
| 2.56 | | | 260 | | |
| 2.57 | | | 90 | | |
| 2.57a | | | 410 | | |
| 2.57b | | | 41 | | |
| 2.58 | | | 78 | | 258 |
| 2.59 | | | 97 | | |
| 2.59a | | | 4100 | | |
| 2.59b | | | 36 | | |
| 3.1 | | | 110 | | 382 |
| 3.2 | | | 52 | | 125 |
| 3.3 | | | 440 | | 787 |
| 3.4 | | | 6100 | | |
| 3.5 | | | 120 | | 140 |
| 3.6 | | | 100 | | 270 |
| 3.7 | | | 53 | | 116 |
| 3.8 | | | 51 | | 62 |
| 3.9 | | | 120 | | 377 |
| 3.10 | | | 140 | | 490 |
| 4.1 | | | 100 | | 140 |
| 4.1a | | | 4900 | | |
| 4.1b | 18 | 14 | 34 | 31 | 73 |
| 4.2 | | | 670 | | |
| 4.3 | | | 49 | | |
| 4.4 | | | 400 | | |
| 4.5 | | | 25 | | |
| 4.6a | | | 30 | | 102 |
| 4.6b | | | 24 | | 35 |
| 4.7a | | | 24 | | 35 |
| 4.7b | | | 8 | | 34 |
| 4.8 | | | 24 | | 42 |
| 4.9a | | | 25 | | 54 |
| 4.9b | | | 38 | | 39 |
| 4.10a | | | 26 | | 72 |
| 4.10b | | | 19 | | 56 |
| 4.11 | | | 120 | | |
| 5.1 | | | 450 | | |
| 6.0 | | | 320 | | 746 |
TABLE 1
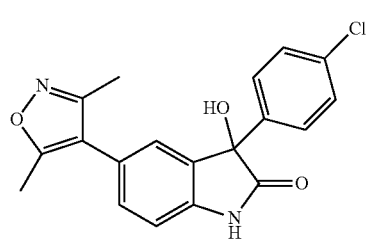 [SMILES: Cc1noc(C)c1-c1ccc2c(c1)C(O)(c1ccc(Cl)cc1)C(=O)N2]
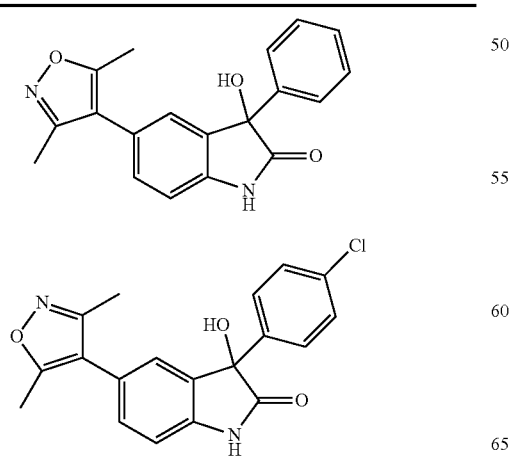
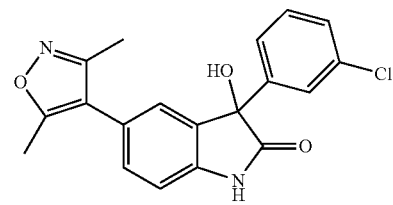 [SMILES: Cc1noc(C)c1-c1ccc2c(c1)C(O)(c1cccc(Cl)c1)C(=O)N2]
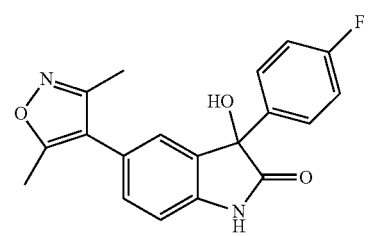 [SMILES: Cc1noc(C)c1-c1ccc2c(c1)C(O)(c1ccc(F)cc1)C(=O)N2]
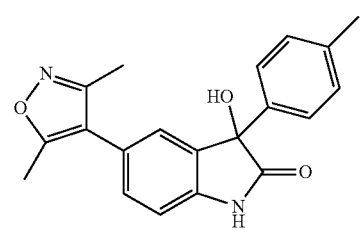 [SMILES: Cc1ccc(C2(O)C(=O)Nc3ccc(-c4c(C)noc4C)cc32)cc1]
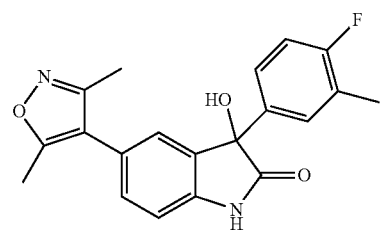 [SMILES: Cc1cc(C2(O)C(=O)Nc3ccc(-c4c(C)noc4C)cc32)ccc1F]
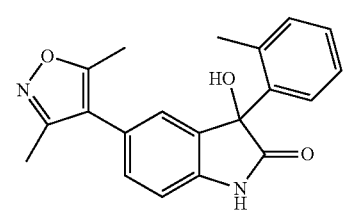 [SMILES: Cc1ccccc1C1(O)C(=O)Nc2ccc(-c3c(C)noc3C)cc21]
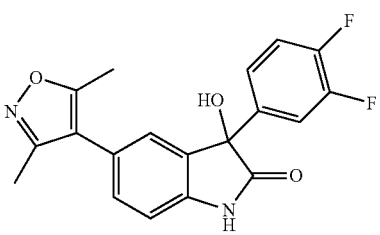 [SMILES: Cc1noc(C)c1-c1ccc2c(c1)C(O)(c1ccc(F)c(F)c1)C(=O)N2]
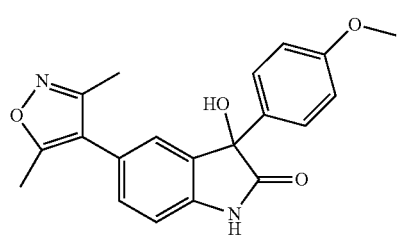 [SMILES: COc1ccc(C2(O)C(=O)Nc3ccc(-c4c(C)noc4C)cc32)cc1]

TABLE 1-continued
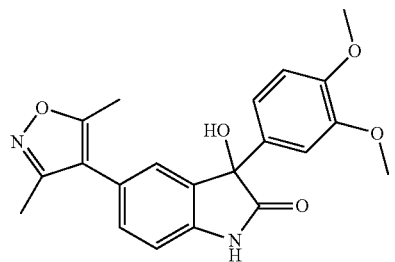 [SMILES: COc1ccc(C2(O)C(=O)Nc3ccc(-c4c(C)noc4C)cc32)cc1OC]
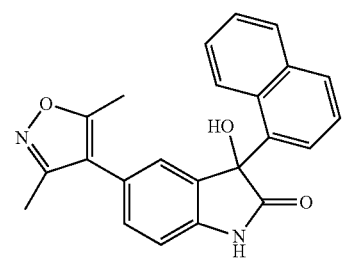 [SMILES: Cc1noc(C)c1-c1ccc2c(c1)C(O)(c1cccc3ccccc13)C(=O)N2]
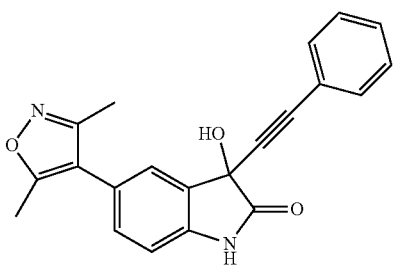 [SMILES: Cc1noc(C)c1-c1ccc2c(c1)C(O)(C#Cc1ccccc1)C(=O)N2]
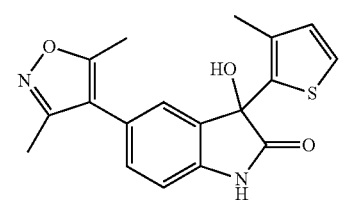 [SMILES: Cc1ccsc1C1(O)C(=O)Nc2ccc(-c3c(C)noc3C)cc21]
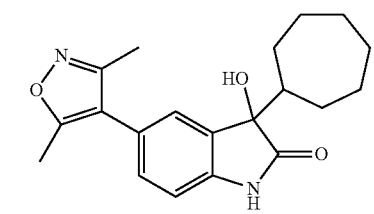
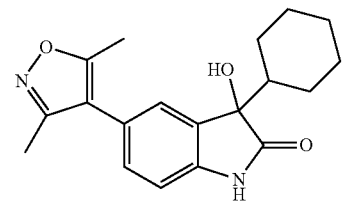 [SMILES: Cc1noc(C)c1-c1ccc2c(c1)C(O)(C1CCCCC1)C(=O)N2]
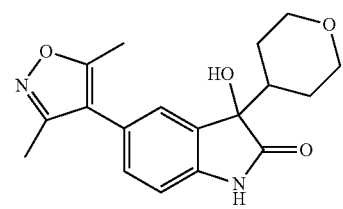 [SMILES: Cc1noc(C)c1-c1ccc2c(c1)C(O)(C1CCOCC1)C(=O)N2]
TABLE 1-continued
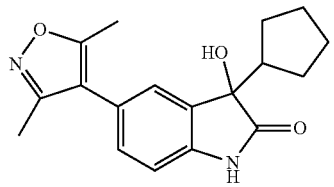 [SMILES: Cc1noc(C)c1-c1ccc2c(c1)C(O)(C1CCCC1)C(=O)N2]
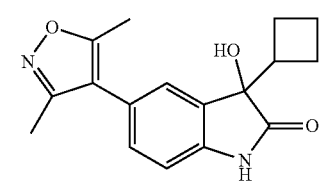 [SMILES: Cc1noc(C)c1-c1ccc2c(c1)C(O)(C1CCC1)C(=O)N2]
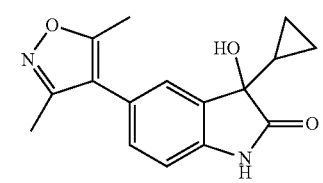 [SMILES: Cc1noc(C)c1-c1ccc2c(c1)C(O)(C1CC1)C(=O)N2]
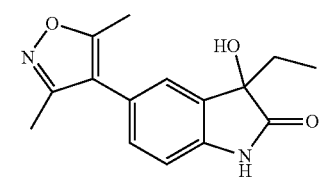 [SMILES: CCC1(O)C(=O)Nc2ccc(-c3c(C)noc3C)cc21]
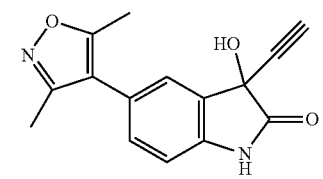 [SMILES: C#CC1(O)C(=O)Nc2ccc(-c3c(C)noc3C)cc21]
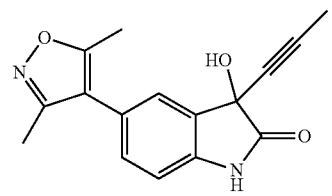 [SMILES: CC#CC1(O)C(=O)Nc2ccc(-c3c(C)noc3C)cc21]
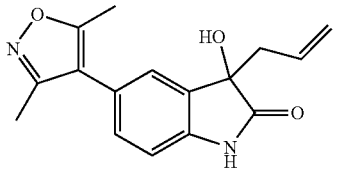 [SMILES: C=CCC1(O)C(=O)Nc2ccc(-c3c(C)noc3C)cc21]
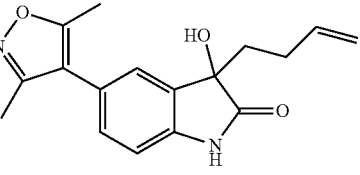

TABLE 1-continued
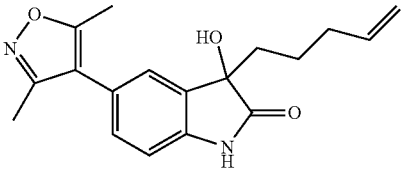 [SMILES: C=CCCCC1(O)C(=O)Nc2ccc(-c3c(C)noc3C)cc21]
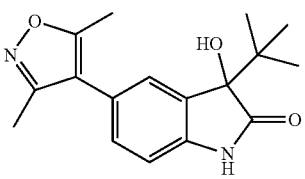 [SMILES: Cc1noc(C)c1-c1ccc2c(c1)C(O)(C(C)(C)C)C(=O)N2]
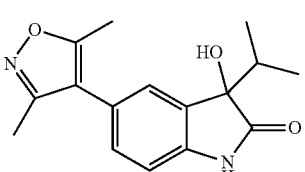
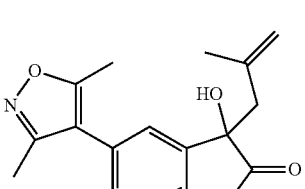
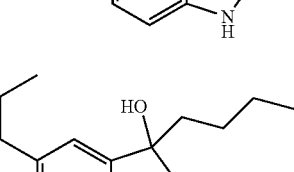
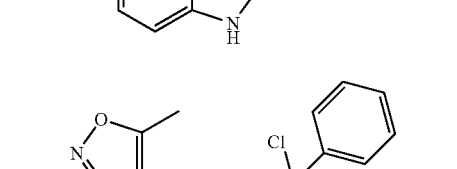
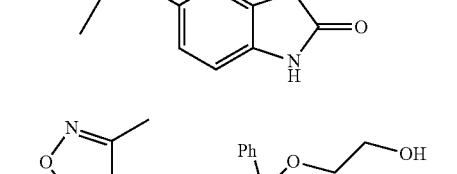
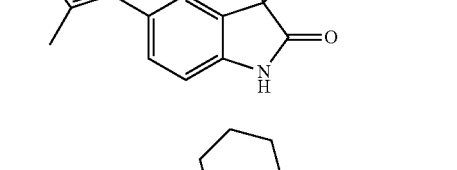
TABLE 1-continued
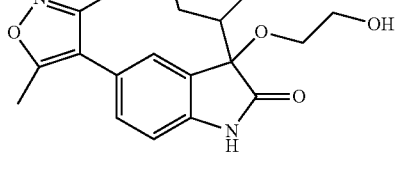
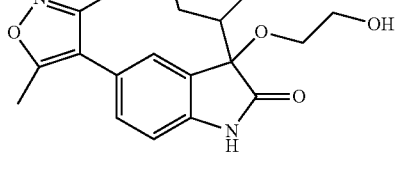
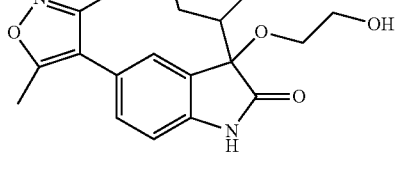
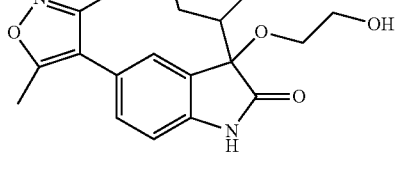
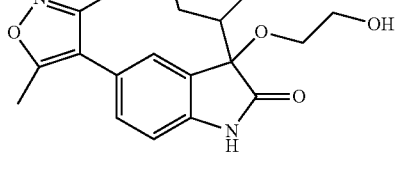
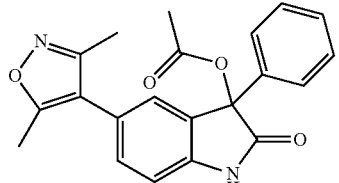
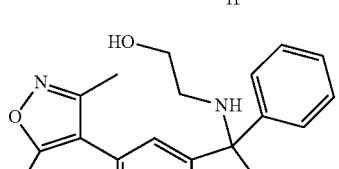
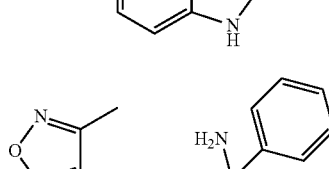

TABLE 1-continued
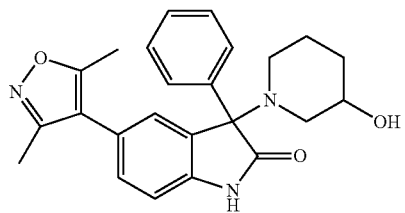 [SMILES: Cc1noc(C)c1-c1ccc2c(c1)C(c1ccccc1)(N1CCCC(O)C1)C(=O)N2]
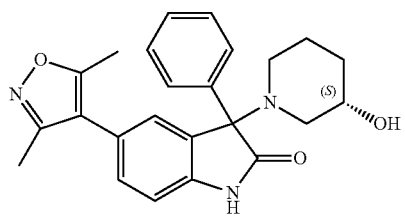
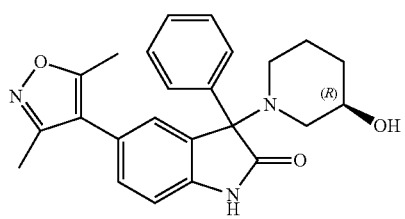
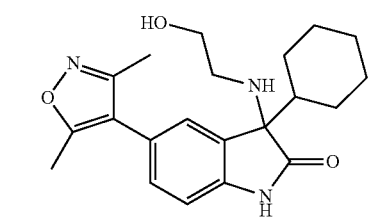 [SMILES: Cc1noc(C)c1-c1ccc2c(c1)C(NCCO)(C1CCCCC1)C(=O)N2]
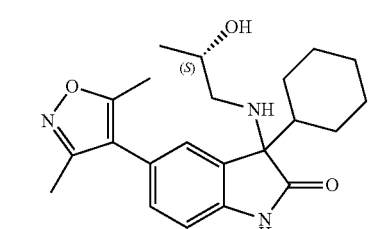
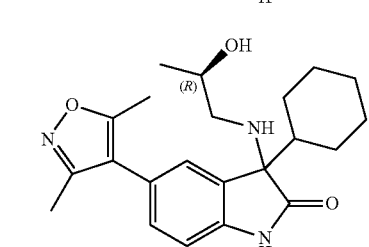
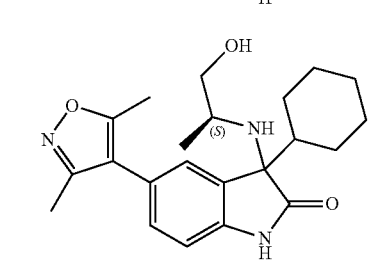
TABLE 1-continued
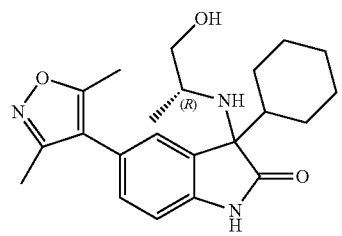
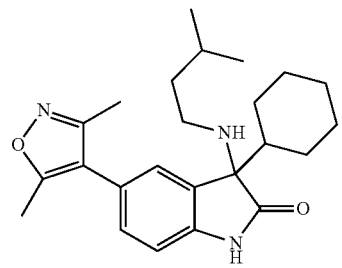 [SMILES: Cc1noc(C)c1-c1ccc2c(c1)C(NCCC(C)C)(C1CCCCC1)C(=O)N2]
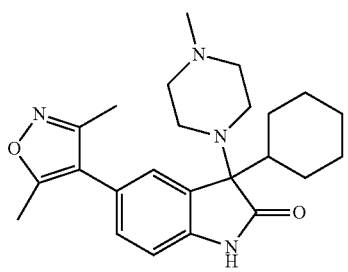 [SMILES: Cc1noc(C)c1-c1ccc2c(c1)C(C1CCCCC1)(N1CCN(C)CC1)C(=O)N2]
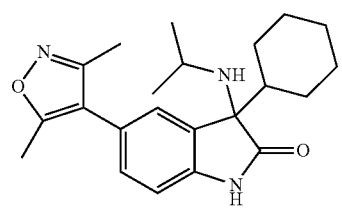 [SMILES: Cc1noc(C)c1-c1ccc2c(c1)C(NC(C)C)(C1CCCCC1)C(=O)N2]
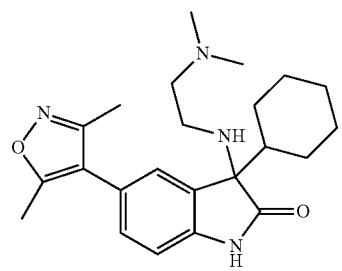 [SMILES: Cc1noc(C)c1-c1ccc2c(c1)C(NCCN(C)C)(C1CCCCC1)C(=O)N2]
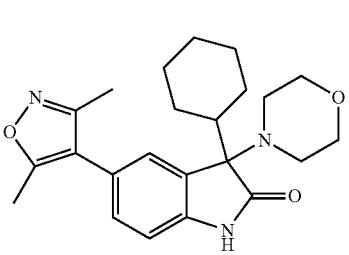 [SMILES: Cc1noc(C)c1-c1ccc2c(c1)C(C1CCCCC1)(N1CCOCC1)C(=O)N2]

TABLE 1-continued
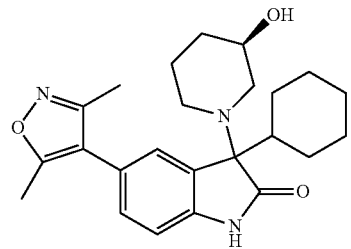 [SMILES: Cc1noc(C)c1-c1ccc2c(c1)C(C1CCCCC1)(N1CCC[C@@H](O)C1)C(=O)N2]
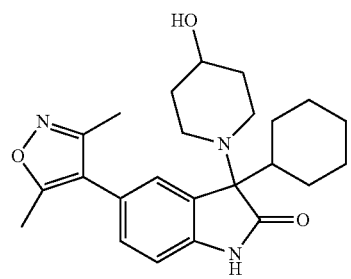 [SMILES: Cc1noc(C)c1-c1ccc2c(c1)C(C1CCCCC1)(N1CCC(O)CC1)C(=O)N2]
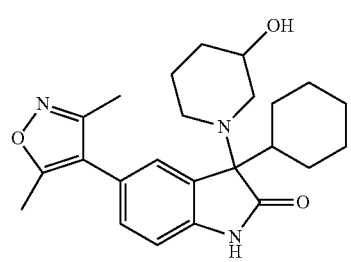 [SMILES: Cc1noc(C)c1-c1ccc2c(c1)C(C1CCCCC1)(N1CCCC(O)C1)C(=O)N2]
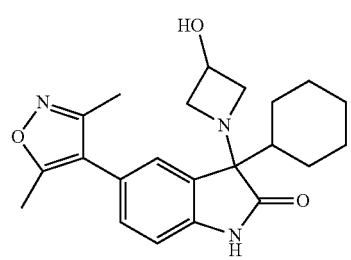 [SMILES: Cc1noc(C)c1-c1ccc2c(c1)C(C1CCCCC1)(N1CC(O)C1)C(=O)N2]
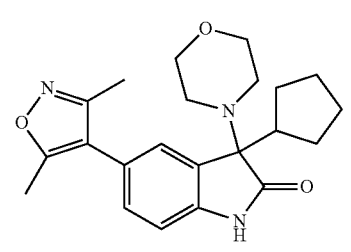 [SMILES: Cc1noc(C)c1-c1ccc2c(c1)C(C1CCCC1)(N1CCOCC1)C(=O)N2]
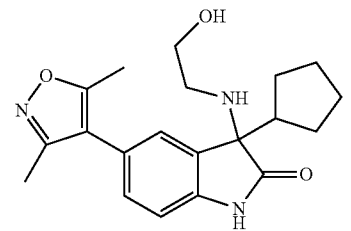 [SMILES: Cc1noc(C)c1-c1ccc2c(c1)C(NCCO)(C1CCCC1)C(=O)N2]
TABLE 1-continued
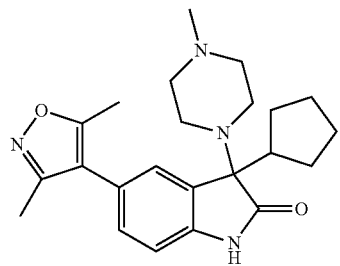 [SMILES: Cc1noc(C)c1-c1ccc2c(c1)C(C1CCCC1)(N1CCN(C)CC1)C(=O)N2]
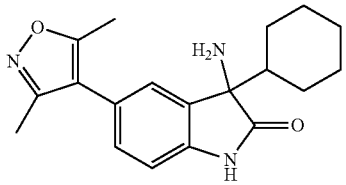
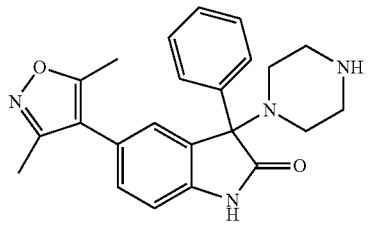 [SMILES: Cc1noc(C)c1-c1ccc2c(c1)C(c1ccccc1)(N1CCNCC1)C(=O)N2]
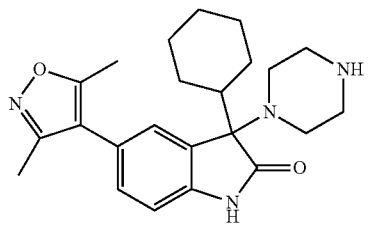 [SMILES: Cc1noc(C)c1-c1ccc2c(c1)C(C1CCCCC1)(N1CCNCC1)C(=O)N2]
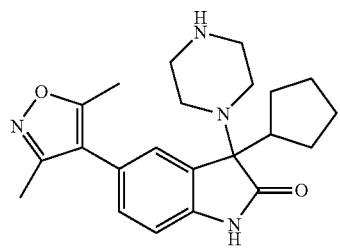
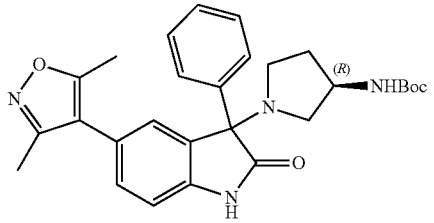
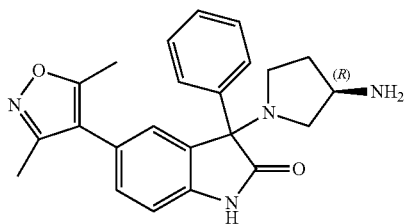

TABLE 1-continued
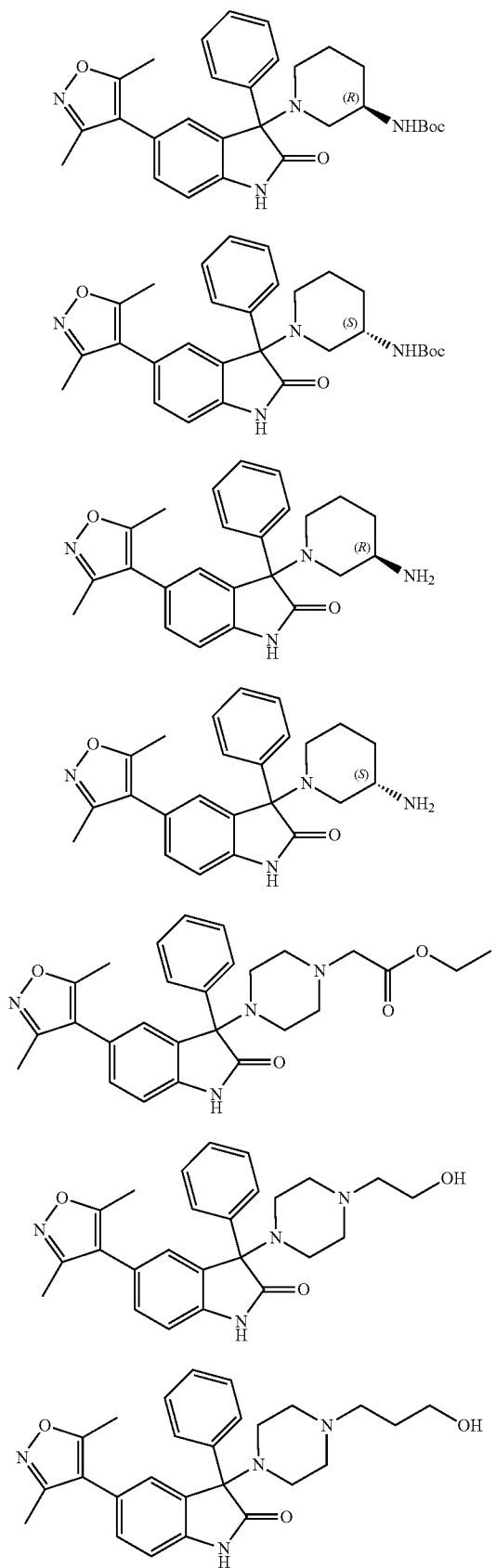
TABLE 1-continued
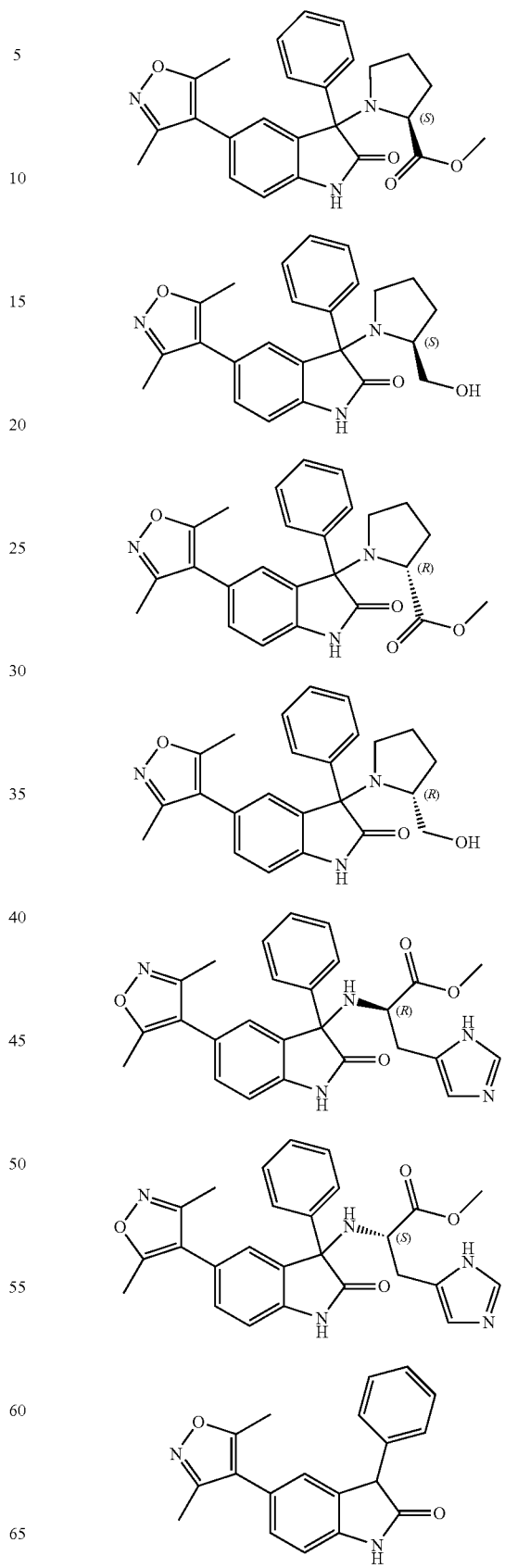

TABLE 1-continued
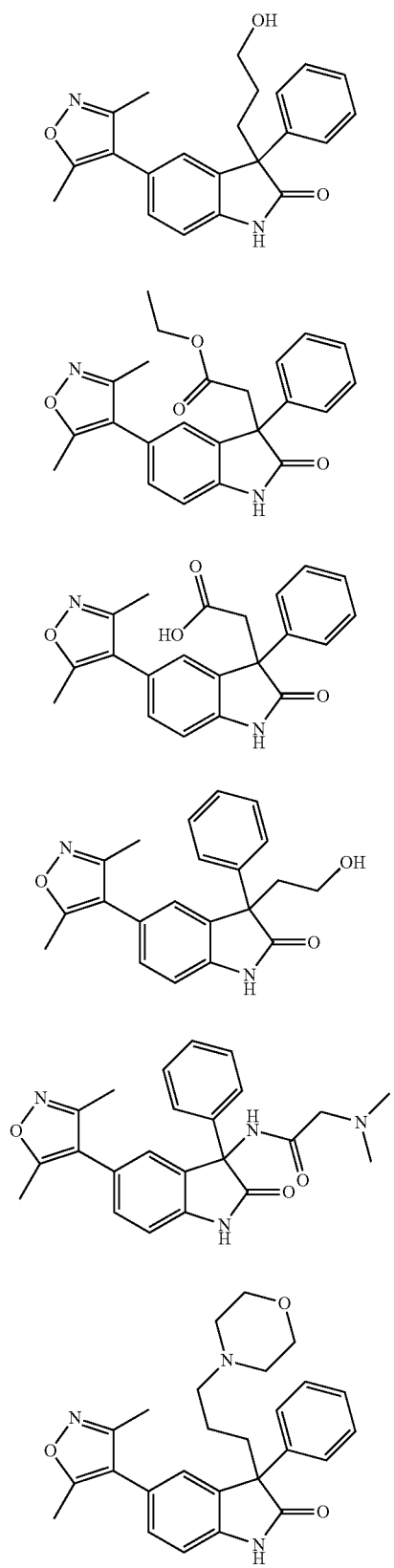
TABLE 1-continued
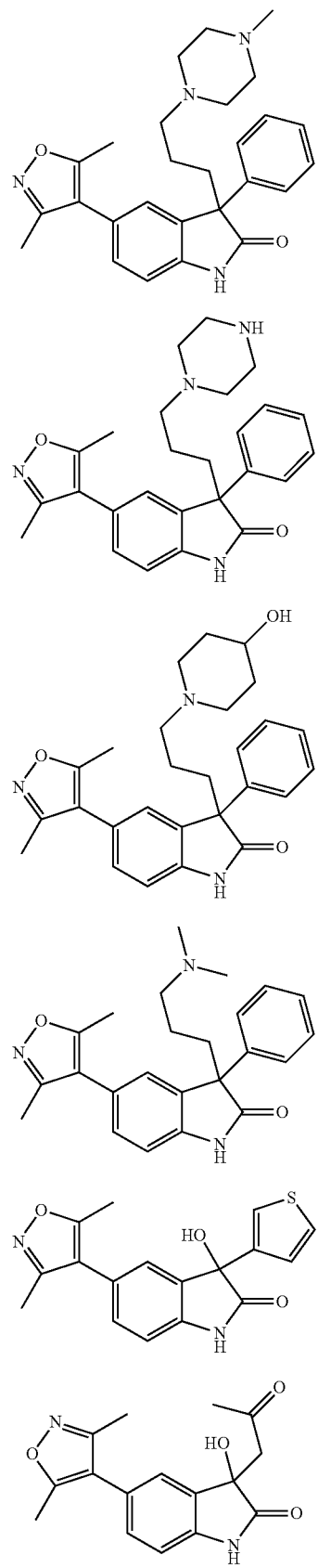

TABLE 1-continued
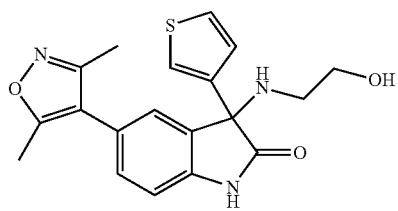 [SMILES: Cc1noc(C)c1-c1ccc2c(c1)C(NCCO)(c1ccsc1)C(=O)N2]
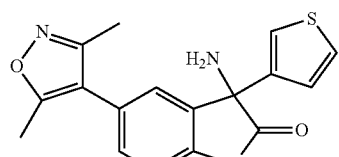
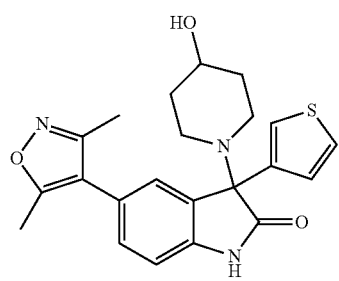 [SMILES: Cc1noc(C)c1-c1ccc2c(c1)C(c1ccsc1)(N1CCC(O)CC1)C(=O)N2]
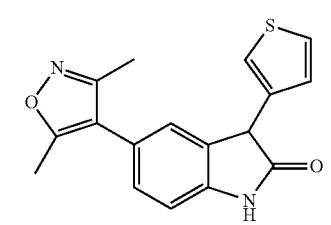 [SMILES: Cc1noc(C)c1-c1ccc2c(c1)C(c1ccsc1)C(=O)N2]
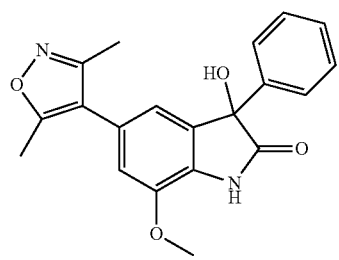 [SMILES: COc1cc(-c2c(C)noc2C)cc2c1NC(=O)C2(O)c1ccccc1]
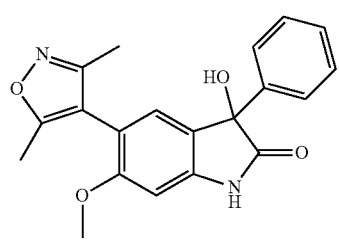 [SMILES: COc1cc2c(cc1-c1c(C)noc1C)C(O)(c1ccccc1)C(=O)N2]
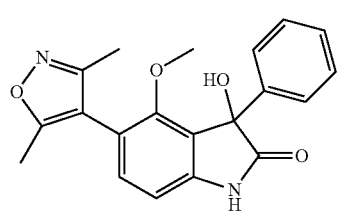 [SMILES: COc1c(-c2c(C)noc2C)ccc2c1C(O)(c1ccccc1)C(=O)N2]
TABLE 1-continued
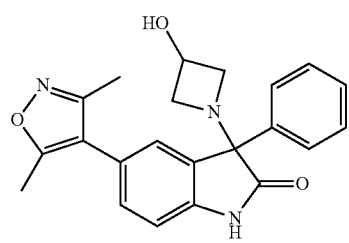 [SMILES: Cc1noc(C)c1-c1ccc2c(c1)C(c1ccccc1)(N1CC(O)C1)C(=O)N2]
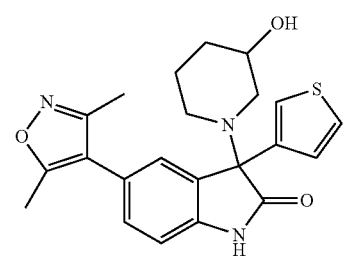 [SMILES: Cc1noc(C)c1-c1ccc2c(c1)C(c1ccsc1)(N1CCCC(O)C1)C(=O)N2]
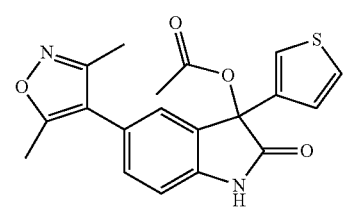 [SMILES: CC(=O)OC1(c2ccsc2)C(=O)Nc2ccc(-c3c(C)noc3C)cc21]
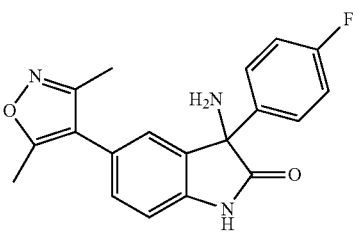 [SMILES: Cc1noc(C)c1-c1ccc2c(c1)C(N)(c1ccc(F)cc1)C(=O)N2]
TABLE 2
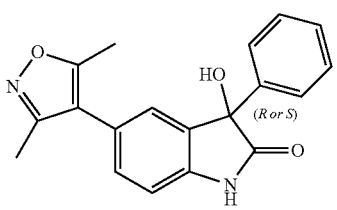
1.1a
Fast isomer in chiral AD HPLC
Eluting reagent: Hexane/EtOH = 4/1
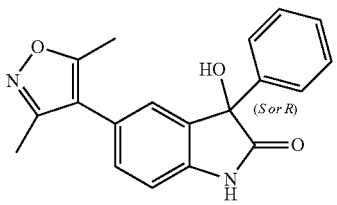
1.1b
Slow isomer in chiral AD HPLC
Eluting reagent: Hexane/EtOH = 4/1

TABLE 2-continued

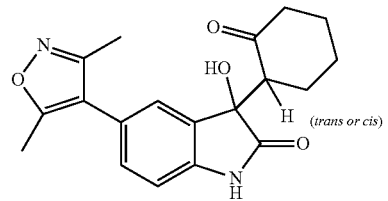

1.30a

Fast isomer in normal chromatography
Eluting reagent: PE/EtOAc = 1/1

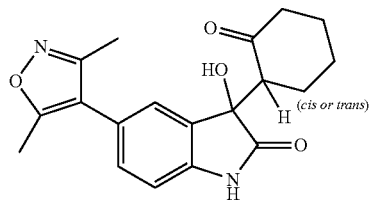

1.30b

Slow isomer in normal chromatography
Eluting reagent: PE/EtOAc = 1/1

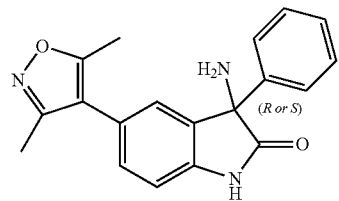

2.2a

Fast isomer in chiral ASH HPLC
Eluting reagent: $CO_2$/MeOH/DEA = 70/30/0.1

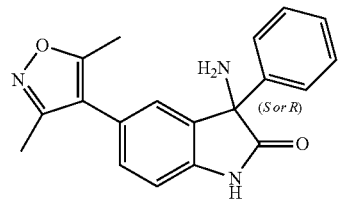

2.2b

Slow isomer in chiral ASH HPLC
Eluting reagent: $CO_2$/MeOH/DEA = 70/30/0.1

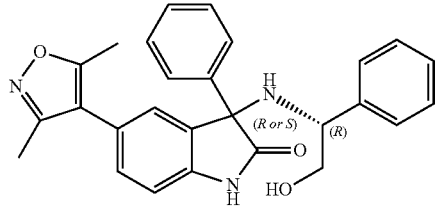

2.7a

Fast isomer in normal chromatography
Eluting reagent: DCM/MeOH = 100/1~20/1

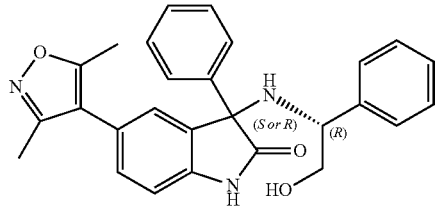

2.7b

Slow isomer in normal chromatography
Eluting reagent: DCM/MeOH = 100/1~20/1

TABLE 2-continued

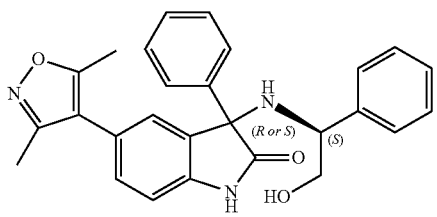

2.8a

Fast isomer in normal chromatography
Eluting reagent: DCM/MeOH = 100/1~20/1

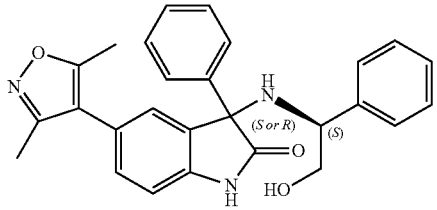

2.8b

Slow isomer in normal chromatography
Eluting reagent: DCM/MeOH = 100/1~20/1

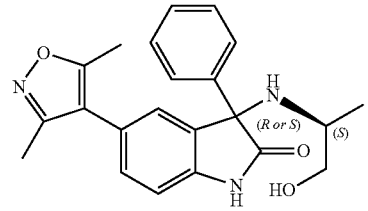

2.9a

Fast isomer in HPLC
Eluting Reagent: $CH_3CN$/$H_2O$/$CF_3COOH$ = 25/100/0.1

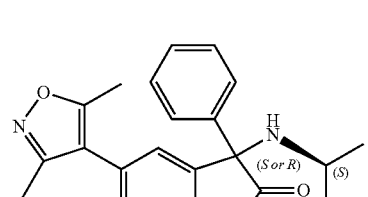

2.9b

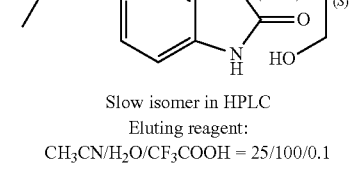

Slow isomer in HPLC
Eluting reagent: $CH_3CN$/$H_2O$/$CF_3COOH$ = 25/100/0.1

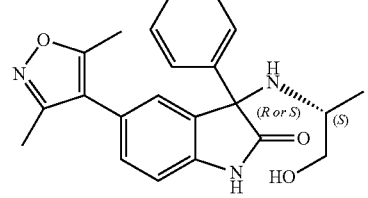

2.10a

Fast isomer in HPLC
Eluting Reagent: $CH_3CN$/$H_2O$/$CF_3COOH$ = 25/100/0.1

TABLE 2-continued

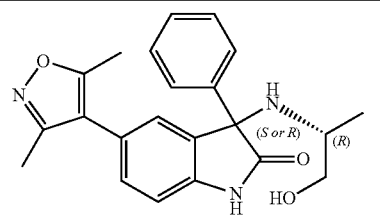

2.10b

Slow isomer in HPLC
Eluting reagent:
CH$_3$CN/H$_2$O/CF$_3$COOH = 25/100/0.1

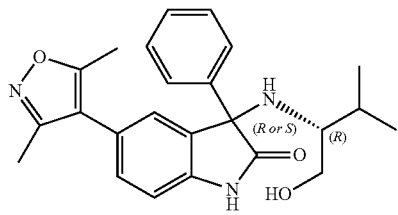

2.11a

Fast isomer in normal chromatography
Eluting reagent: DCM/MeOH = 100/1~20/1

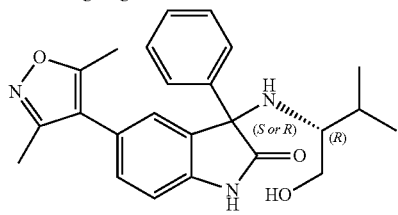

2.11b

Slow isomer in normal chromatography
Eluting reagent: DCM/MeOH = 100/1~20/1

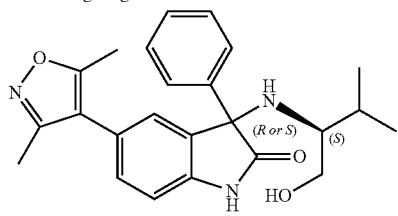

2.12a

Fast isomer in normal chromatography
Eluting reagent: DCM/MeOH = 100/1~20/1

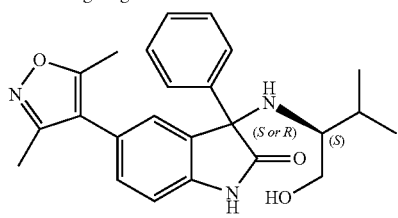

2.12b

Slow isomer in normal chromatography
Eluting reagent: DCM/MeOH = 100/1~20/1

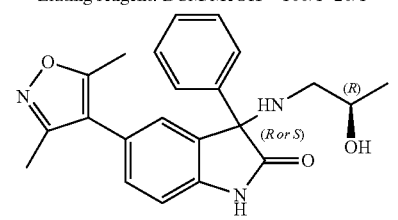

2.13a

Fast isomer in HPLC
Eluting reagent:
CH$_3$CN/H$_2$O/CF$_3$COOH = 25/100/0.1

TABLE 2-continued

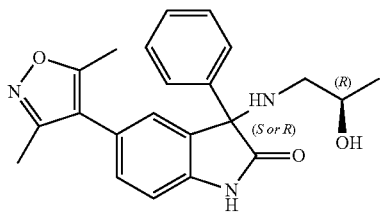

2.13b

Slow isomer in HPLC
Eluting reagent:
CH$_3$CN/H$_2$O/CF$_3$COOH = 25/100/0.1

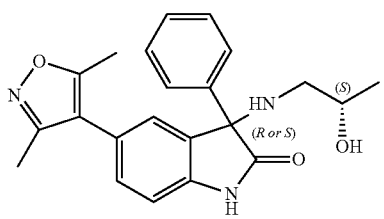

2.14a

Fast isomer in HPLC
Eluting reagent:
CH$_3$CN/H$_2$O/CF$_3$COOH = 25/100/0.1

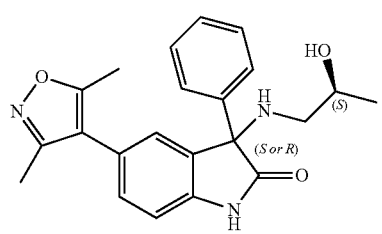

2.14b

Slow isomer in HPLC
Eluting reagent:
CH$_3$CN/H$_2$O/CF$_3$COOH = 25/100/0.1

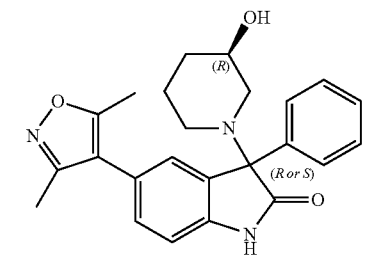

2.17a

Fast isomer in normal chromatography
Eluting reagent: DCM/MeOH = 40/1

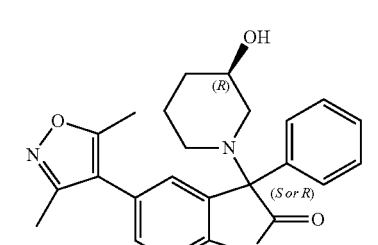

2.17b

Slow isomer in normal chromatography
Eluting reagent: DCM/MeOH = 40/1

TABLE 2-continued

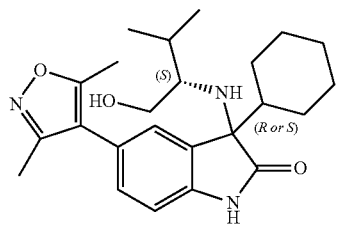

2.19a

Fast isomer in normal chromatography
Eluting reagent: DCM/MeOH = 50/1

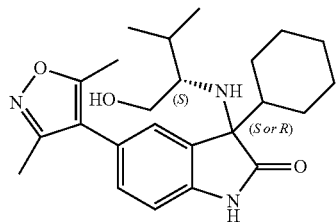

2.19b

Slow isomer in normal chromatography
Eluting reagent: DCM/MeOH = 50/1

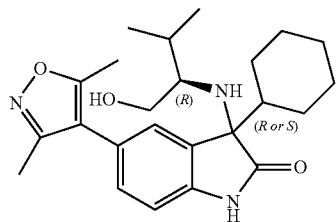

2.20a

Fast isomer in normal chromatography
Eluting reagent: DCM/MeOH = 50/1

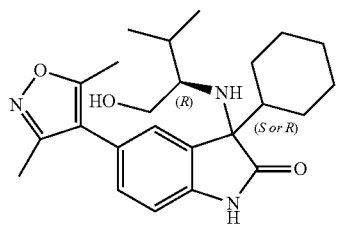

2.20b

Slow isomer in normal chromatography
Eluting reagent: DCM/MeOH = 50/1

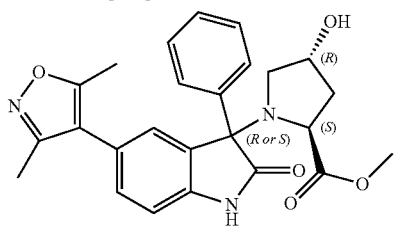

2.50a

Fast isomer in normal chromatography
Eluting reagent: DCM/MeOH = 20/1

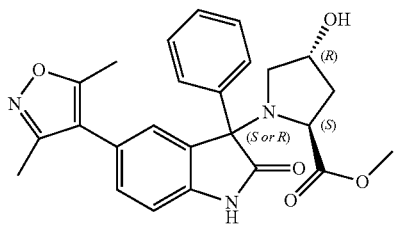

2.50b

Slow isomer in normal chromatography
Eluting reagent: DCM/MeOH = 20/1

TABLE 2-continued

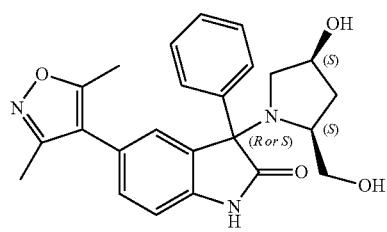

2.51a

Fast isomer in normal chromatography
Eluting reagent: DCM/MeOH = 10/1

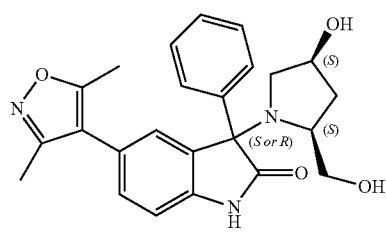

2.51b

Slow isomer in normal chromatography
Eluting reagent: DCM/MeOH = 10/1

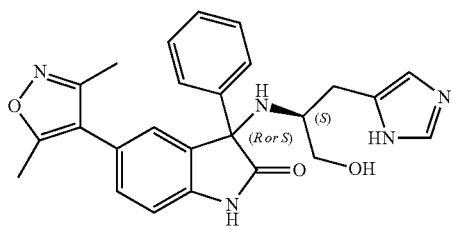

2.57a

Fast isomer in HPLC
Eluting reagent:
CH$_3$CN/H$_2$O = 15/1 to 20/1

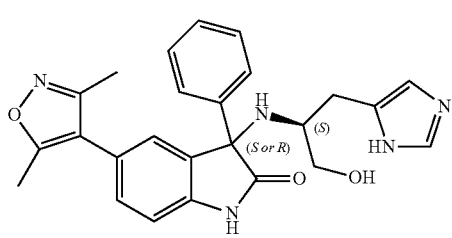

2.57b

Slow isomer in HPLC
Eluting reagent:
CH$_3$CN/H$_2$O = 15/1 to 20/1

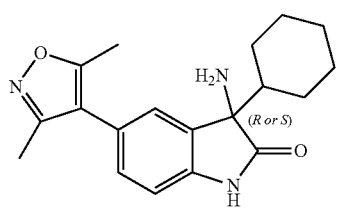

2.37a

Fast isomer in chiral AD HPLC
Eluting reagent: Hexane/EtOH = 7/3

TABLE 2-continued

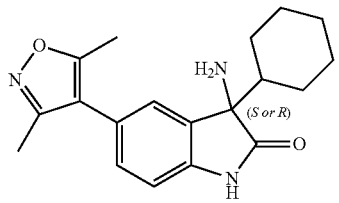

2.37b

Slow isomer in chiral AD HPLC
Eluting reagent: Hexane/EtOH = 7/3

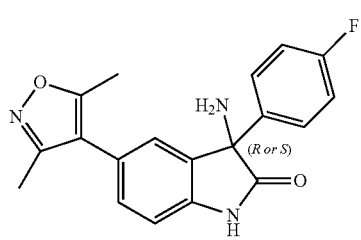

2.59a

Fast isomer in chiral OJH HPLC
Eluting reagent: $CO_2$/(MeOH70ACN30) = 70/30

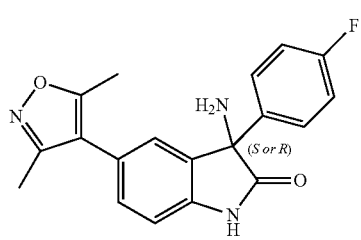

2.59b

Slow isomer in chiral OJH HPLC
Eluting reagent: $CO_2$/(MeOH70ACN30) = 70/30

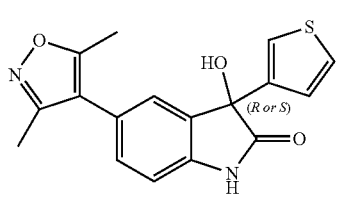

4.1a

Fast isomer in chiral SFC
Eluting reagent: $CO_2$/MeOH = 7/3

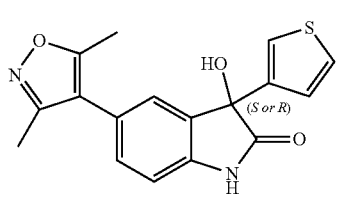

4.1b

Slow isomer in chiral SFC
Eluting reagent: $CO_2$/MeOH = 7/3

TABLE 2-continued

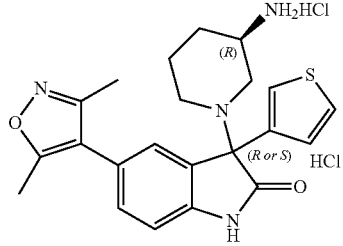

4.6a

Fast isomer in chiral AD HPLC
Eluting reagent:
Hexane/EtOH/Et$_3$N = 80/20/0.1

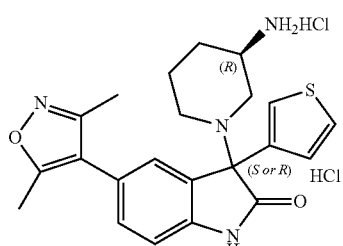

4.6b

Slow isomer in chiral AD HPLC
Eluting reagent:
Hexane/EtOH/Et$_3$N = 80/20/0.1

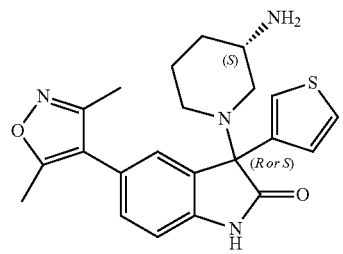

4.7a

Fast isomer in chiral AD HPLC
Eluting reagent:
Hexane/EtOH/Et$_3$N = 80/20/0.1

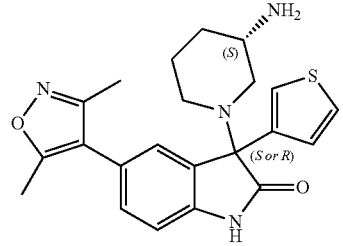

4.7b

Slow isomer in chiral AD HPLC
Eluting reagent:
Hexane/EtOH/Et$_3$N = 80/20/0.1

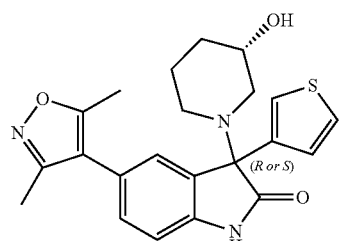

4.9a

Fast isomer in normal chromatography
Eluting reagent: DCM/MeOH = 15/1

TABLE 2-continued

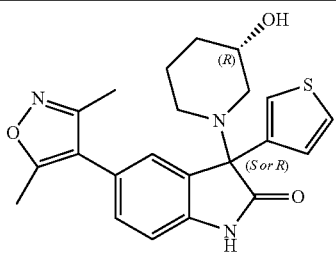

4.9b

Slow isomer in normal chromatography
Eluting reagent: DCM/MeOH = 15/1

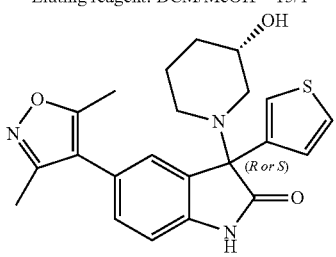

4.10a

Fast isomer in normal chromatography
Eluting reagent: DCM/MeOH = 15/1

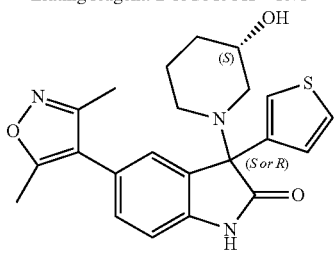

4.10b

Slow isomer in normal chromatography
Eluting reagent: DCM/MeOH = 15/1

What is claimed is:

1. A compound of Formula I:

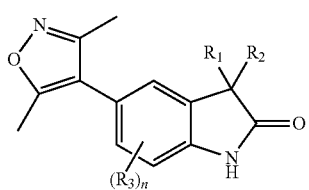

I or a stereoisomer or a pharmaceutically acceptable salt thereof, wherein:

$R^1$ is —$NR^5R^6$, wherein $R^5$ and $R^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms; or wherein $R^5$ and $R^6$ together with the atom(s) to which they are attached, each can form an optionally substituted, cyclohydrocarbon ring;

$R^2$ is a hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms;

$R^3$ is halogen, lower alkyl, hydroxyl, lower alkyloxy, or lower acyl and n is 0, 1, 2 or 3.

2. The compound according to claim 1 wherein:

$R^2$ is a hydrocarbon selected from C3-C8 cycloalkyl, C5-C8 cycloalkenyl, and C6-C14 aryl, wherein each hydrocarbon is optionally-substituted and optionally comprises 1-3 heteroatoms.

3. The compound according to claim 1 wherein:

$R^2$ is C6-C14 aryl, wherein aryl is optionally-substituted and optionally comprises 1-3 heteroatoms.

4. The compound according to claim 1 selected from the group consisting of:

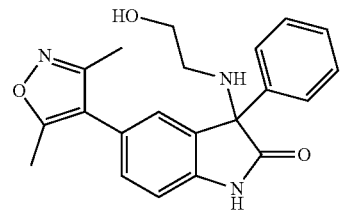

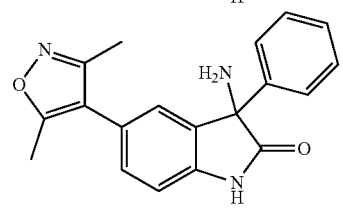

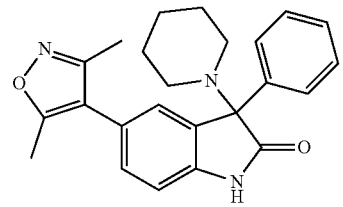

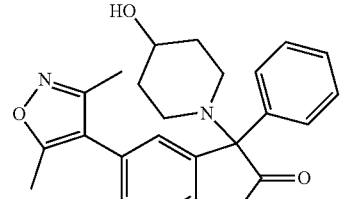

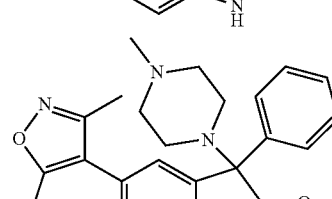

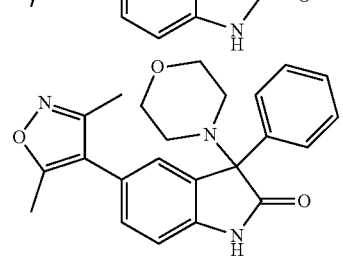

-continued
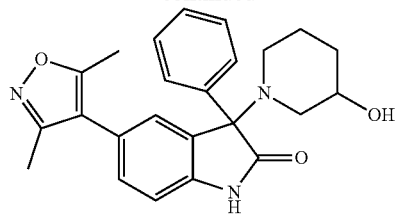
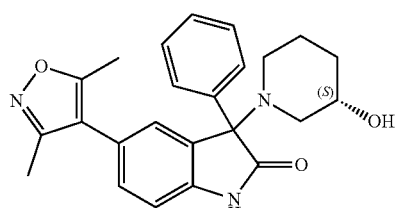
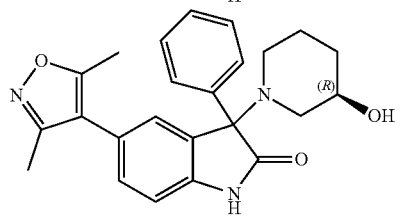
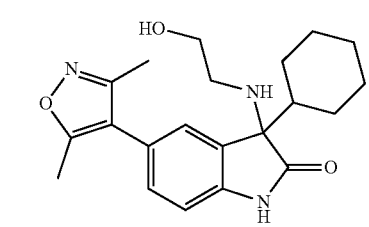
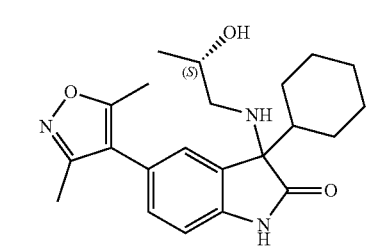
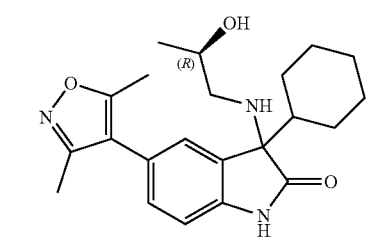
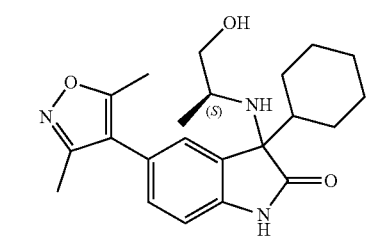
-continued
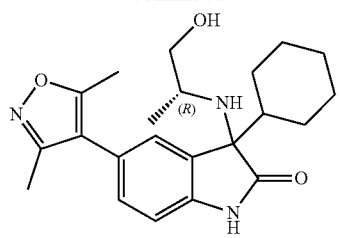
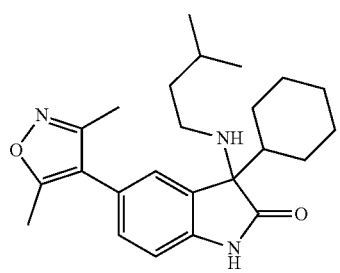
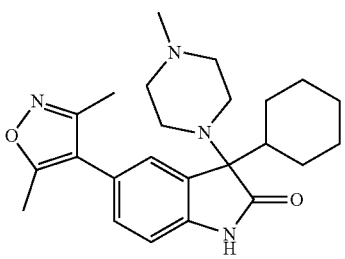
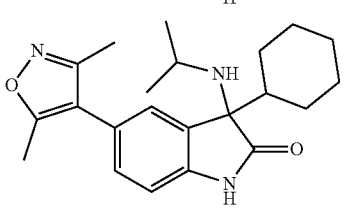
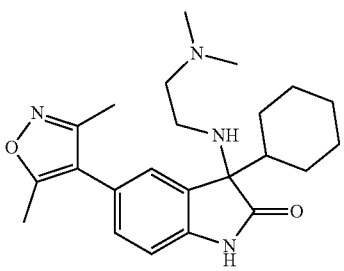
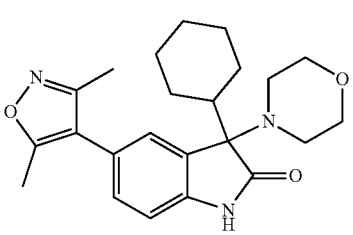
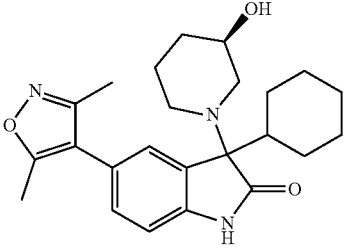

-continued
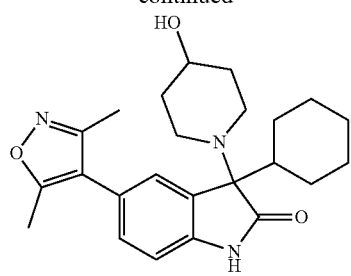
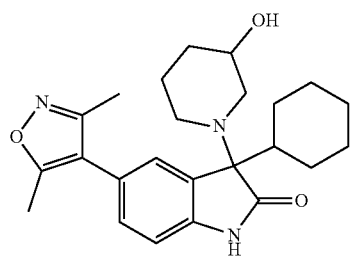
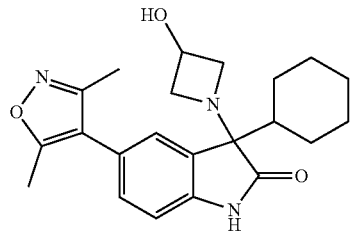
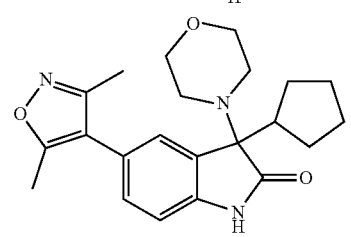
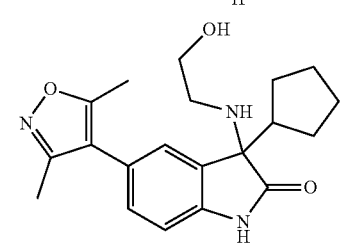
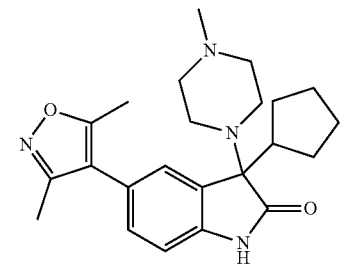
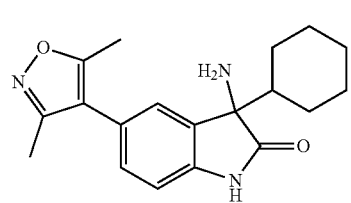
-continued
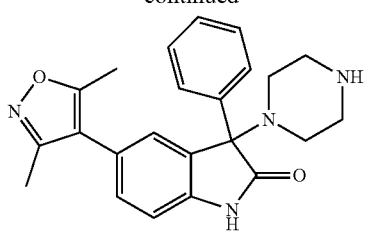
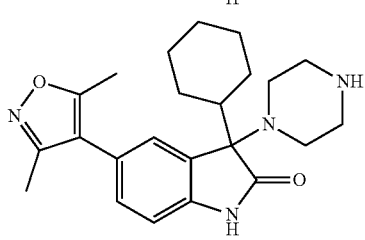
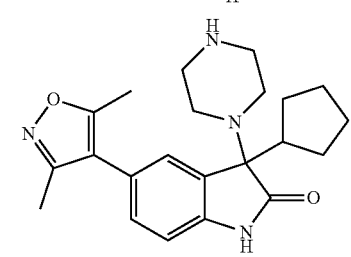
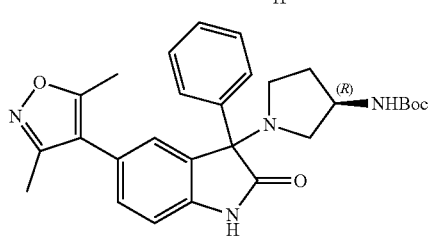
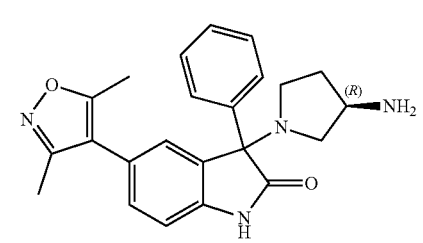
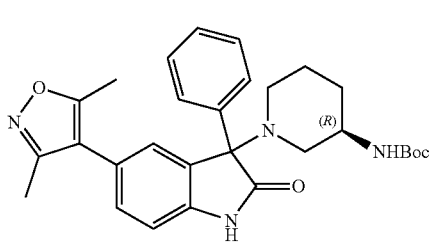
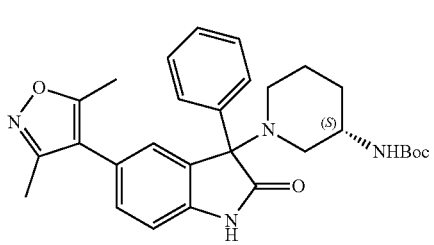

121
-continued
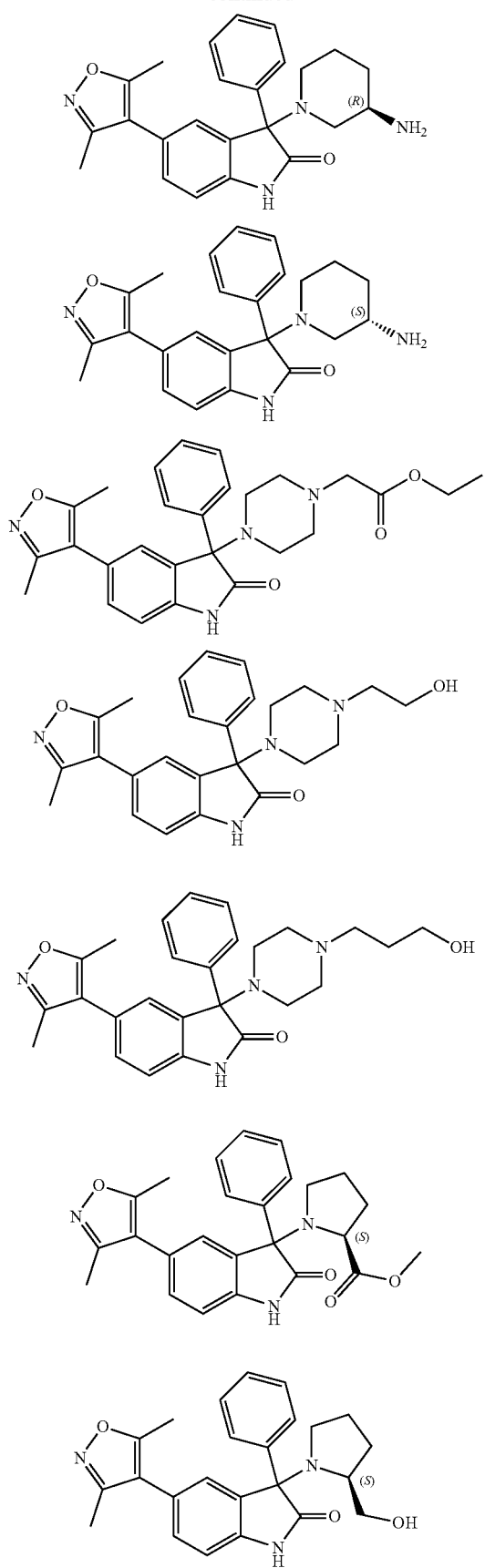
122
-continued
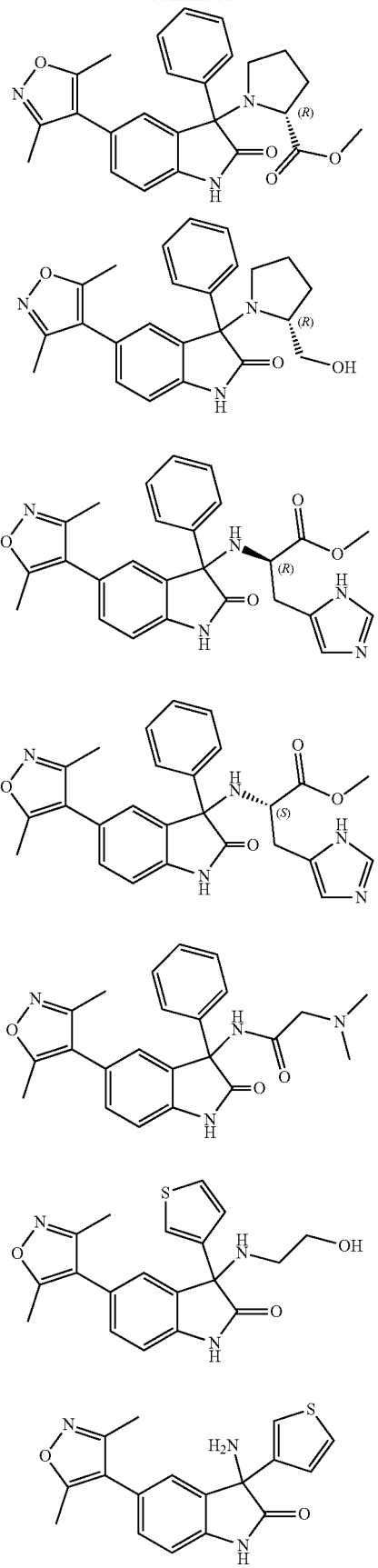

or a stereoisomer or a pharmaceutically acceptable salt thereof.

5. The compound according to claim 1 selected from the group consisting of the following compounds showing the following stereochemistry:

-continued 2.9a

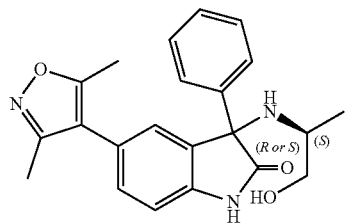

Fast isomer in HPLC
Eluting reagent:
CH$_3$CN/H$_2$O/CF$_3$COOH = 25/100/0.1

2.9b

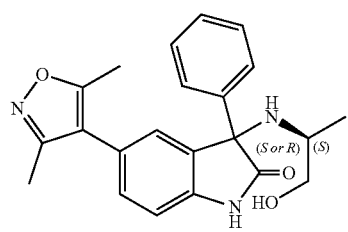

Slow isomer in HPLC
Eluting reagent:
CH$_3$CN/H$_2$O/CF$_3$COOH = 25/100/0.1

2.10a

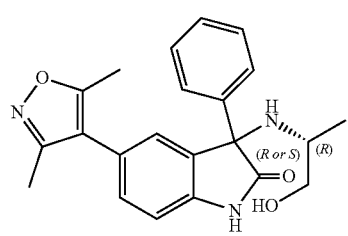

Fast isomer in HPLC
Eluting reagent:
CH$_3$CN/H$_2$O/CF$_3$COOH = 25/100/0.1

2.10b

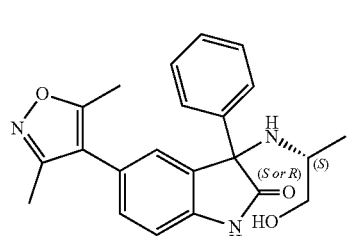

Slow isomer in HPLC
Eluting reagent:
CH$_3$CN/H$_2$O/CF$_3$COOH = 25/100/0.1

2.11a

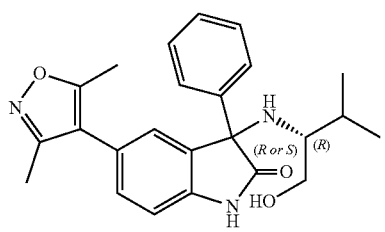

Fast isomer in normal chromatography
Eluting reagent: DCM/MeOH = 100/1~20/1

2.11b

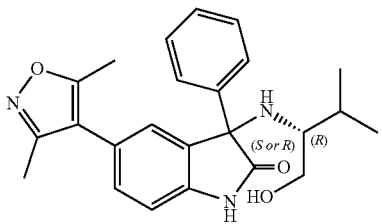

Slow isomer in normal chromatography
Eluting reagent: DCM/MeOH = 100/1~20/1

2.12a

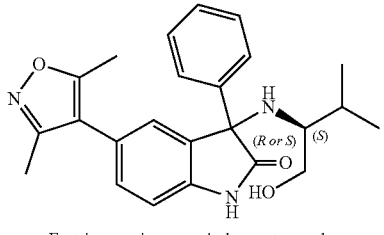

Fast isomer in normal chromatography
Eluting reagent: DCM/MeOH = 100/1~20/1

2.12b

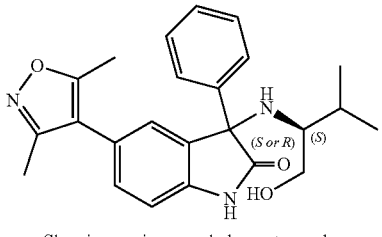

Slow isomer in normal chromatography
Eluting reagent: DCM/MeOH = 100/1~20/1

2.13a

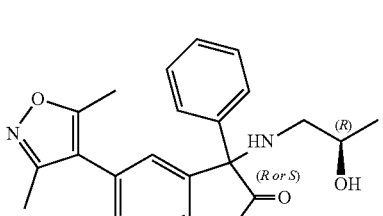

Fast isomer in HPLC
Eluting reagent:
CH$_3$CN/H$_2$O/CF$_3$COOH = 25/100/0.1

2.13b

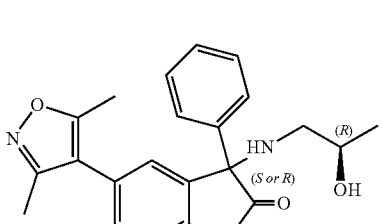

Slow isomer in HPLC
Eluting reagent:
CH$_3$CN/H$_2$O/CF$_3$COOH = 25/100/0.1

2.14a

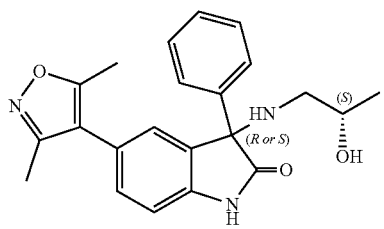

Fast isomer in HPLC
Eluting reagent:
CH$_3$CN/H$_2$O/CF$_3$COOH = 25/100/0.1

2.14b

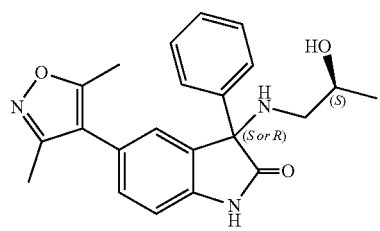

Slow isomer in HPLC
Eluting reagent:
CH$_3$CN/H$_2$O/CF$_3$COOH = 25/100/0.1

2.17a

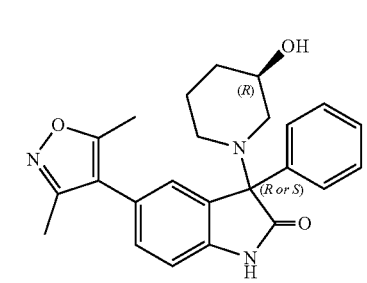

Fast isomer in normal chromatography
Eluting reagent: DCM/MeOH = 40/1

2.17b

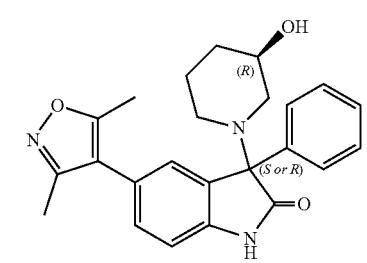

Slow isomer in normal chromatography
Eluting reagent: DCM/MeOH = 40/1

2.19a

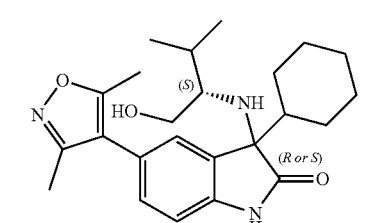

Fast isomer in normal chromatography
Eluting reagent: DCM/MeOH = 50/1

2.19b

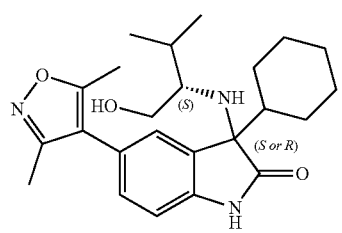

Slow isomer in normal chromatography
Eluting reagent: DCM/MeOH = 50/1

2.20a

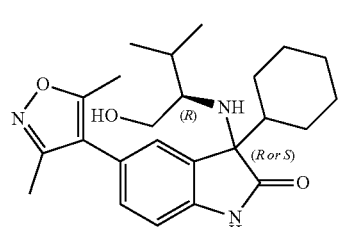

Fast isomer in normal chromatography
Eluting reagent: DCM/MeOH = 50/1

2.20b

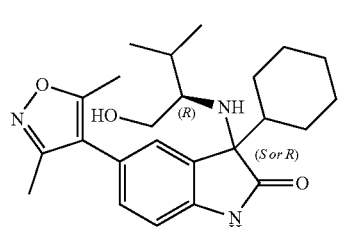

Slow isomer in normal chromatography
Eluting reagent: DCM/MeOH = 50/1

2.50a

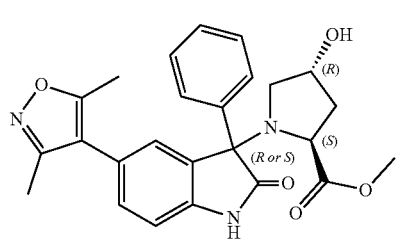

Fast isomer in normal chromatography
Eluting reagent: DCM/MeOH = 20/1

2.50b

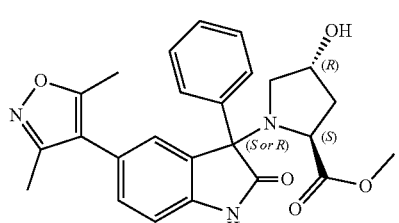

Fast isomer in normal chromatography
Eluting reagent: DCM/MeOH = 20/1

2.51a

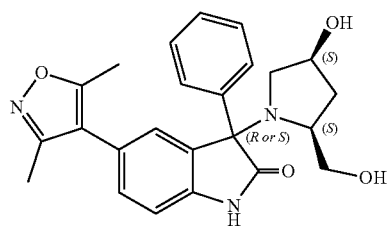

Fast isomer in normal chromatography
Eluting reagent: DCM/MeOH = 10/1

2.51b

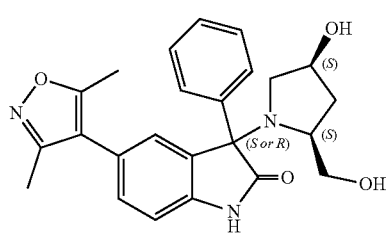

Slow isomer in normal chromatography
Eluting reagent: DCM/MeOH = 10/1

2.57a

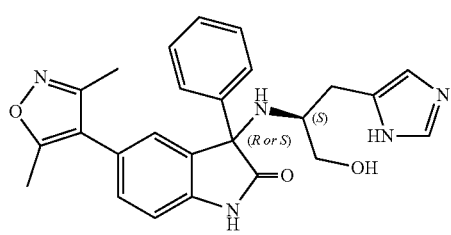

Fast isomer in HPLC
Eluting reagent:
$CH_3CN/H_2O$ = 15/1 to 20/1

2.57b

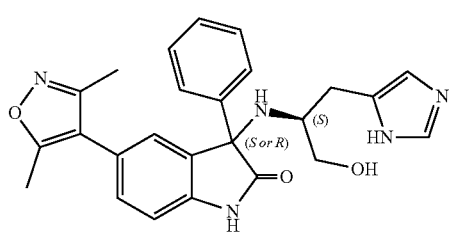

Slow isomer in HPLC
Eluting reagent:
$CH_3CN/H_2O$ = 15/1 to 20/1

2.37a

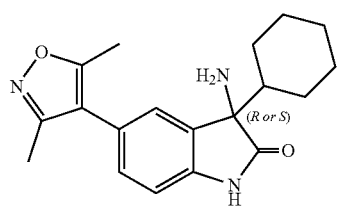

Fast isomer in chiral AD HPLC
Eluting reagent: Hexane/EtOH = 7/3

2.37b

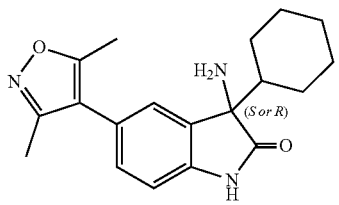

Slow isomer in chiral AD HPLC
Eluting reagent: Hexane/EtOH = 7/3

2.59a

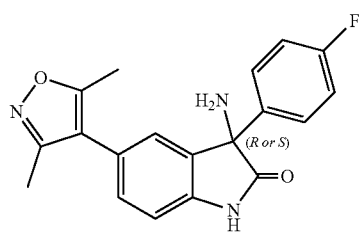

Fast isomer in chiral OJH HPLC
Eluting reagent: $CO_2$/(MeOH70ACN30) = 70/30

2.59b

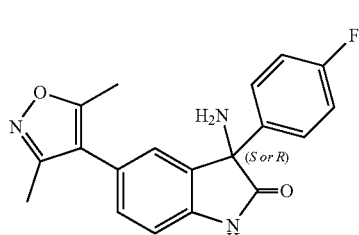

Slow isomer in chiral OJH HPLC
Eluting reagent: $CO_2$/(MeOH70ACN30) = 70/30

4.6a

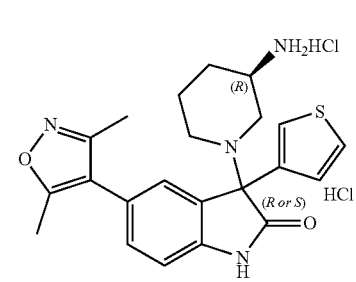

Fast isomer in chiral AD HPLC
Eluting reagent:
Hexane/EtOH/$Et_3N$ = 80/20/0.1

4.6b

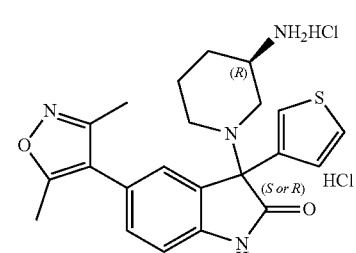

Slow isomer in chiral AD HPLC
Eluting reagent:
Hexane/EtOH/$Et_3N$ = 80/20/0.1

-continued

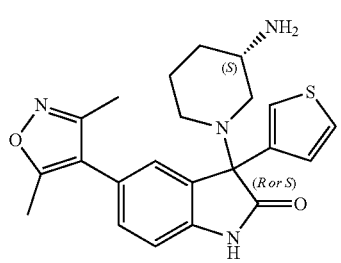

Fast isomer in chiral AD HPLC
Eluting reagent:
Hexane/EtOH/Et$_3$N = 80/20/0.1

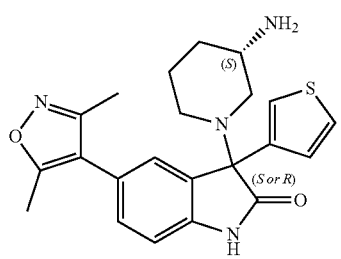

Slow isomer in chiral AD HPLC
Eluting reagent:
Hexane/EtOH/Et$_3$N = 80/20/0.1

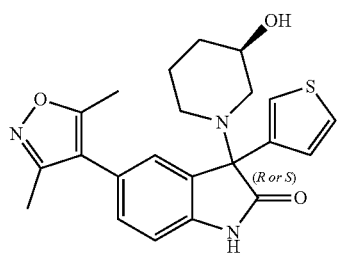

Fast isomer in normal chromatography
Eluting reagent: DCM/MeOH = 15/1

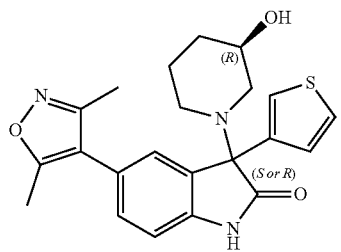

Slow isomer in normal chromatography
Eluting reagent: DCM/MeOH = 15/1

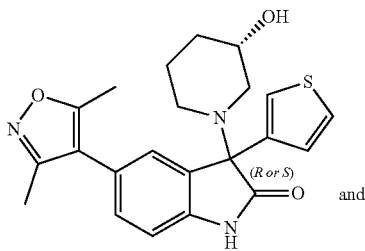

Fast isomer in normal chromatography
Eluting reagent: DCM/MeOH = 15/1

-continued

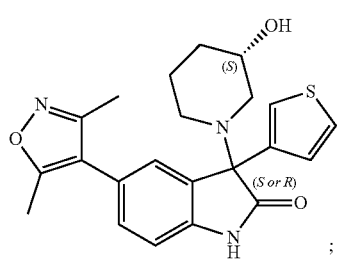

Slow isomer in normal chromatography
Eluting reagent: DCM/MeOH = 15/1 or a pharmaceutically acceptable salts thereof.

6. The compound according to claim 1 having a BRD$_4$-inhibiting activity corresponding to an IC50 of 10 μM or less in a BRD$_4$ time-resolved fluorescence resonance energy transfer (TR-FRET) enzyme assay using recombinant human BRD$_4$ (1-4777) bromodomain expressed and purified from *E. coli* with an N-terminal His tag, in binding mixtures of the bromodomain, the compound and a tetra-acetylated histone peptide.

7. A pharmaceutical composition comprising a therapeutically effective amount of a compound of claim 1 in a unit dosage form and one or more pharmaceutically acceptable carriers.

8. A combination comprising a therapeutically effective amount of a compound of claim 1 and a different agent therapeutically active against cancer.

9. A method of treating a disease associated with undesirable BRD$_4$ activity, which comprises administering to a person in need thereof an effective amount of a compound of claim 1, an N-oxide thereof or a prodrug thereof, wherein the disease is a cancer disease selected from lymphoma and neuroblastoma.

10. The compound according to claim 1, wherein R$^1$ is NH$_2$.

11. The compound according to claim 1, wherein R$^i$ is —NR$^5$R$^6$, and R$^5$ and R$^6$ are each independently H or hydrocarbon selected from C1-C8 alkyl, C2-C8 alkenyl, C2-C8 alkynyl, and C6-C14 aryl, wherein each alkyl, alkenyl and alkynyl is optionally cyclized, and each hydrocarbon is optionally-substituted and optionally comprises 1-3 heteroatoms.

12. The compound of claim 4, where the compound is,

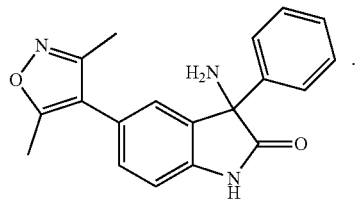 [SMILES: Cc1noc(C)c1-c1ccc2c(c1)C(N)(c1ccccc1)C(=O)N2]

\* \* \* \* \*